US011000506B2

(12) United States Patent
Lewin

(10) Patent No.: US 11,000,506 B2
(45) Date of Patent: May 11, 2021

(54) ENVENOMATION THERAPIES AND RELATED PHARMACEUTICAL COMPOSITIONS, SYSTEMS AND KITS

(71) Applicant: OPHIREX, INC, Corte Madera, CA (US)

(72) Inventor: Matthew R. Lewin, Corte Madera, CA (US)

(73) Assignee: OPHIREX, INC., Corte Madera, CA (US)

( * ) Notice: Subject to any disclaimer, the term of this patent is extended or adjusted under 35 U.S.C. 154(b) by 0 days.

(21) Appl. No.: 15/528,418

(22) PCT Filed: Nov. 20, 2015

(86) PCT No.: PCT/US2015/061834
§ 371 (c)(1),
(2) Date: May 19, 2017

(87) PCT Pub. No.: WO2016/081826
PCT Pub. Date: May 26, 2016

(65) Prior Publication Data
US 2017/0354642 A1    Dec. 14, 2017

Related U.S. Application Data

(60) Provisional application No. 62/082,895, filed on Nov. 21, 2014, provisional application No. 62/131,441, (Continued)

(51) Int. Cl.
| | | |
|---|---|---|
| A61K 31/404 | (2006.01) | |
| A61K 31/167 | (2006.01) | |
| A61K 31/445 | (2006.01) | |
| A61K 31/381 | (2006.01) | |
| A61K 31/541 | (2006.01) | |
| A61K 31/405 | (2006.01) | |
| A61K 31/24 | (2006.01) | |
| A61K 31/245 | (2006.01) | |
| A61K 31/16 | (2006.01) | |
| A61K 38/57 | (2006.01) | |
| A61K 9/00 | (2006.01) | |

(Continued)

(52) U.S. Cl.
CPC .......... *A61K 31/404* (2013.01); *A61K 9/0019* (2013.01); *A61K 9/0043* (2013.01); *A61K 31/16* (2013.01); *A61K 31/167* (2013.01); *A61K 31/24* (2013.01); *A61K 31/245* (2013.01); *A61K 31/381* (2013.01); *A61K 31/405* (2013.01); *A61K 31/445* (2013.01); *A61K 31/541* (2013.01); *A61K 38/57* (2013.01); *A61K 39/39533* (2013.01); *A61K 45/06* (2013.01); *C07K 16/18* (2013.01); *C07K 2317/55* (2013.01); *Y02A 50/30* (2018.01)

(58) Field of Classification Search
CPC .......... A23L 33/40; A23L 33/12; A23L 33/17; A23L 33/19; A23L 33/105; A23L 33/16; A23L 33/15; A23L 33/185; A23L 33/00; A23V 2002/00; A61K 31/404; A61K 9/0019; A61K 9/0043; A61K 31/16; A61K 31/167; A61K 31/24; A61K 31/245; A61K 31/381; A61K 31/405; A61K 31/445; A61K 31/541; A61K 38/57; A61K 39/39533; A61K 45/06; C07K 16/18; C07K 2317/55; Y02A 50/30
See application file for complete search history.

(56) References Cited

U.S. PATENT DOCUMENTS

2003/0225031 A1    12/2003    Quay
2005/0192243 A1     9/2005    Savarese
(Continued)

FOREIGN PATENT DOCUMENTS

WO    1999/29726 A1    6/1999
WO    2009/047762 A1   4/2009
(Continued)

OTHER PUBLICATIONS

Ticli et al (Year: 2005).*
Oslund et al (Year: 2008).*
Marchi-Salvador (Year: 2009).*
Vanzolini (Year: 2002).*
Teixeira (Year: 2009).*
Balsinde (Year: 1999).*
Oslund (Year: 2008).*
Goldberg (Year: 2000).*
Araújo (Year: 2007).*
Ticli (Year: 2005).*
Filho (Year: 2009).*

(Continued)

Primary Examiner — Jeffrey S Lundgren
Assistant Examiner — Ibrahim D Bori
(74) Attorney, Agent, or Firm — Henry D. Coleman; R. Neil Sudol

(57) ABSTRACT

The invention provides methods of treatment, pharmaceutical compositions, systems and kits appropriate for first line and/or adjunct therapy with antivenom using at least one active component, in some instances at least two active components and in other instances no more than two active components selected from the group consisting of a selective secretory PLA$_2$ inhibitor (sPLA2 or PLA$_2$ inhibitor), a metalloproteinase inhibitor, a serine protease inhibitor, antivenom, one or more acetylcholinesterase inhibitors or a nAChR agonist paired with a mAChR antagonist, a NMDA receptor antagonist and a spreading factor inhibitor to treat a subject who suffers from an envenomation, preferably at the time of envenomation and often within a period of less than about an hour after an envenomation or 6 hours after an envenomation and throughout the course of treatment at time with or without antivenom as an adjunct therapy after an envenomation by, for example, a snake or invertebrate.

23 Claims, 25 Drawing Sheets

Related U.S. Application Data filed on Mar. 11, 2015, provisional application No. 62/243,374, filed on Oct. 19, 2015.

(51) Int. Cl.
*A61K 45/06* (2006.01)
*A61K 39/395* (2006.01)
*C07K 16/18* (2006.01)

(56) References Cited

U.S. PATENT DOCUMENTS

| | | |
|---|---|---|
| 2007/0093518 A1 | 4/2007 | Wetherell et al. |
| 2009/0042939 A1 | 2/2009 | Ieni |
| 2009/0062369 A1* | 3/2009 | Trias .................. A61P 9/00 514/419 |
| 2013/0253060 A1* | 9/2013 | Mehendale .......... A61K 31/353 514/563 |
| 2014/0087003 A1 | 3/2014 | Cisneros |

FOREIGN PATENT DOCUMENTS

| | | | |
|---|---|---|---|
| WO | WO-2009047762 A1 * | 4/2009 | ............. A61K 38/08 |
| WO | 2014039920 A1 | 3/2014 | |

OTHER PUBLICATIONS

Lewin, Matthew R. et al. "Early Treatment With Intranasal Neostigmine Reduces Mortality in a Mouse Model of *Naja naja* (Indian Cobra) Envenomation", Journal of Tropical Medicine, vol. 128, No. 1, Jan. 2014, pp. 38-6.

Howes et al., "Neutralization of the Haemorrhagic Activities of Viperine Snake Venoms and Venom Metalloproteinases Using Synthetic Peptide Inhibitors and Chelators", vol. 49, No. 5, Mar. 2007, pp. 734-739, Tox, Elmsford, NY, US.

Bustillo, Soledad et al., "Synergism Between Baltergin Metalloproteinase and BA SPII RP4 Plafromvenom on Skeletal Muscle (C2C12) Cells" vol. 59, No. 2 pp. 338-343, Nov. 8, 2011, Toxicon, Elmsford, NY, US.

Rucavado, Alexandra et al, "Proteomics of Wound Exudate in Snake Venom-Induced Pathology: Search for Biomakers to Assess Tissue Damage and Therapeutic Success", Journal of Proteome Research, vol. 10, No. 4, pp. 1987-2005, Apr. 1, 2011.

Ramar Perumal Samy et al, "Therapeutic application of natural inhibitors against snake venom phospholipase A2", Bioinforamtion, vol. 8, No. 1, pp. 48-57, Jun. 2012.

Silvana Marcussi et al., "Snake Venon Phospholipase A2 Inhibitors: Medicinal Chemistry and Therapeutic Potential", Current Topics in Medicinal Chemistry, vol. 7, No. 8, Apr. 2007.

Pereanez Jaime Andres et al., "The biflavonoid morelloflavone inhibits the enzymatic and biological activities of a snake venom phospholipase A2", Chemico-Biological Interactions, Elsevier Science Irland, IR., vol. 220, Jul. 2014.

Kabburalli Sunitha et al., "Neutralization of Haemorrhagic Activity of Viper Venoms by . . . Anti-Haemorrhagic Activity of DFD", Basic & Clinical Pharmacology & Toxicology. vol. 109, No. 4, Jun. 2011.

A.K. Al-Asmari, "Pharmacological characherization of reat paw edema induced by Naja haje arabica venom", JOurnal of Venomous Animals and Toxins including Tropical Diseases. Mar. 2005.

Ticli F K et al, "Rosmarinic acid, a new snake venom phospholipase A2 inhibitor from Cordia verbenacea (Boraginaceae): antiserum actio potentiation and molecular interaction". Toxicon, Elmsford, NY, vol. 46, No. 3, Sep. 2005.

Jaime Andra S Pereaa Ez et al. "Inhibitory Effects of Bile Acids on Enzymatic and Pharmacological Activities of a Snake Venom Phospholipase Afrom Group IIa", Journal of Protein Chemistry, Kluwer Academic Publishers—Plenum Publishers, NE, vol. 30, No. Apr. 4, 2001.

B.M.A. Carvakho et al., "s Inhibitors Isolated from Brazlian Plants: Synthetic and Natural Molecules", Biomed Research International, vol. 2013, Jan. 2013.

Boilard Eric et al., "Secreted Phospholipase A2 Inhibitors are also Potent Blockers of Binding to the M-Type Receptor", Biochemistry, American Chemcial Society, vol. 45, No. 44.

Lewin Matthew R. et al, "Varespladid appears to be a very potent broad-spectrum, inhibitor of snake venom PLA2s from six continents" Toxicon, vol. 117, Jan. 2016.

Lewin Matthew R. et al, "Varespladid appears to be a very potent broad-spectrum, inhibitor of snake venom Phospholipase A2s and a Possible Pre-Referral Treatment for Envenomation" Toxins, vol. 8, No. 9 , Aug. 2016.

Yiding Wang et al., "Exploration of the Inhibitory Potential of Varespladib for Snakebite Envenomation" Molecules Online, vol. 23, No. 2, Feb. 2018.

Clark JD et al., Potential therapeutic uses of phospolipase A2 inhibitors. Expert Opinion on Therapeutic Patents, 2004; 14(7):937-950.

Rucavado A et al., Effect of the metalloproteinase inhibitor batimastat in the systemic toxicity induced by Bothrops asper snake venom: understanding the role of metalloproteinases in envenomation. Toxicon., Mar. 15, 2004; 43(4):417-424.

Trinh HH et al., Use of CROFAB antivenin in the management of a very young pediatric copperhead envenomation. The Journal of Emergency Medicine, 2005; 29(2):159-162.

Winkel, Dr. Kenneth et al. The Use of Anticholinesterase therapy// The University of Melbourne, Rfcd 1998 6 Digit Code Toxicology, chpt 12, pp. 12.1-12.4, Introduction, case report.

* cited by examiner

X-axis = Time (Minutes); Y-axis = absorbance

X-axis = Time (Minutes); Y-axis = Fluorescence

FIGURE 5A-F
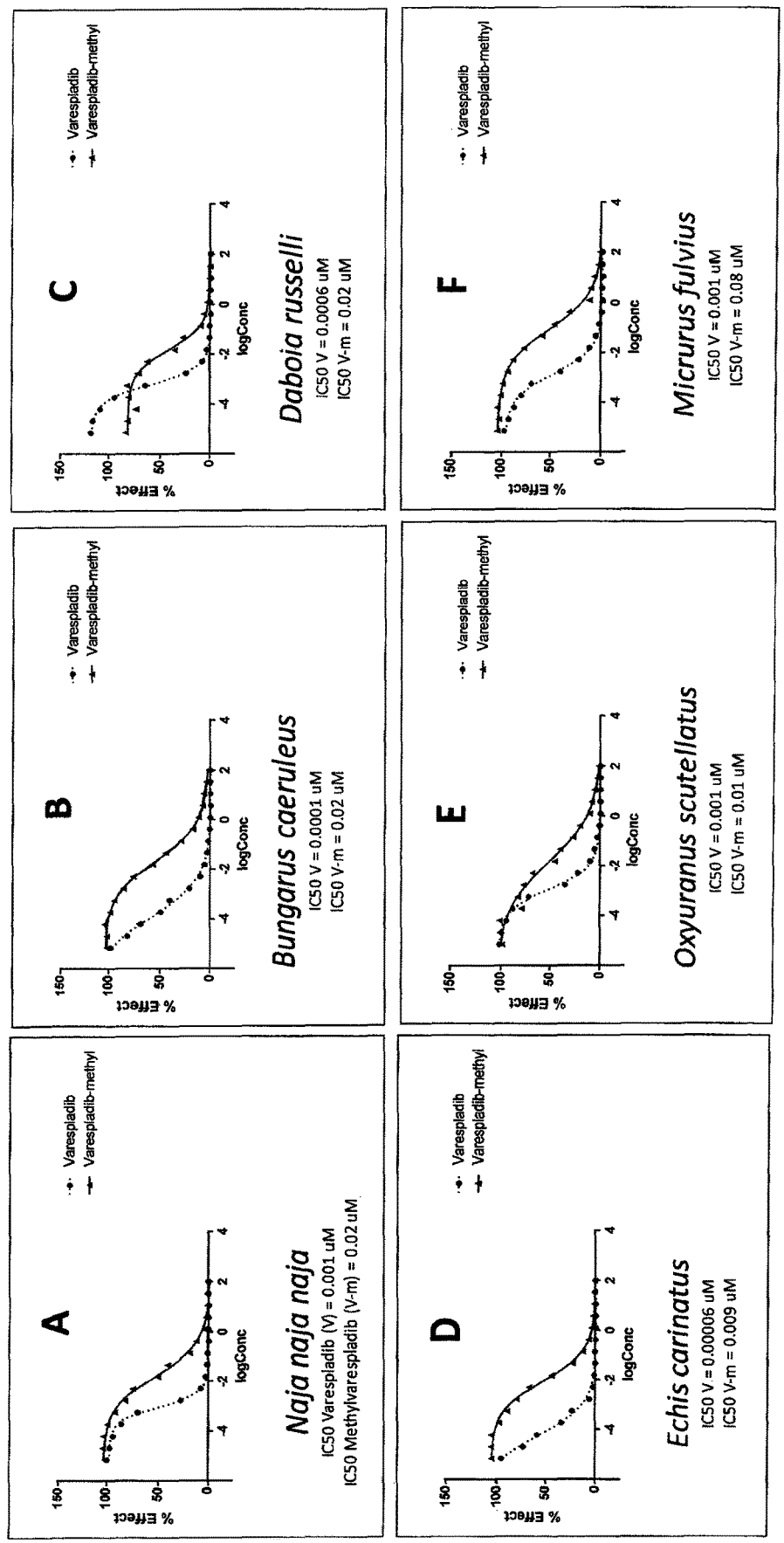

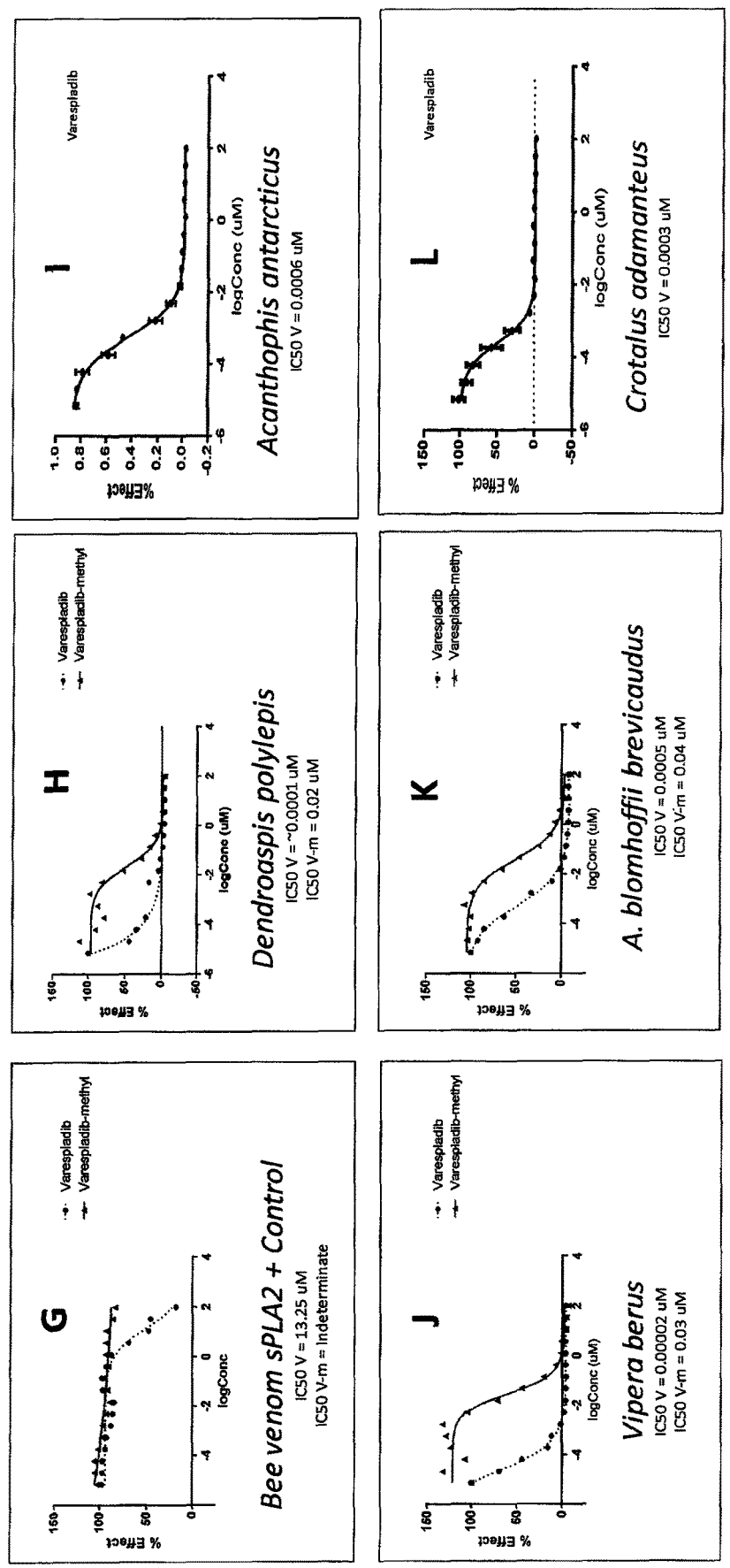
FIGURE 5G-L

FIGURE 5M-R
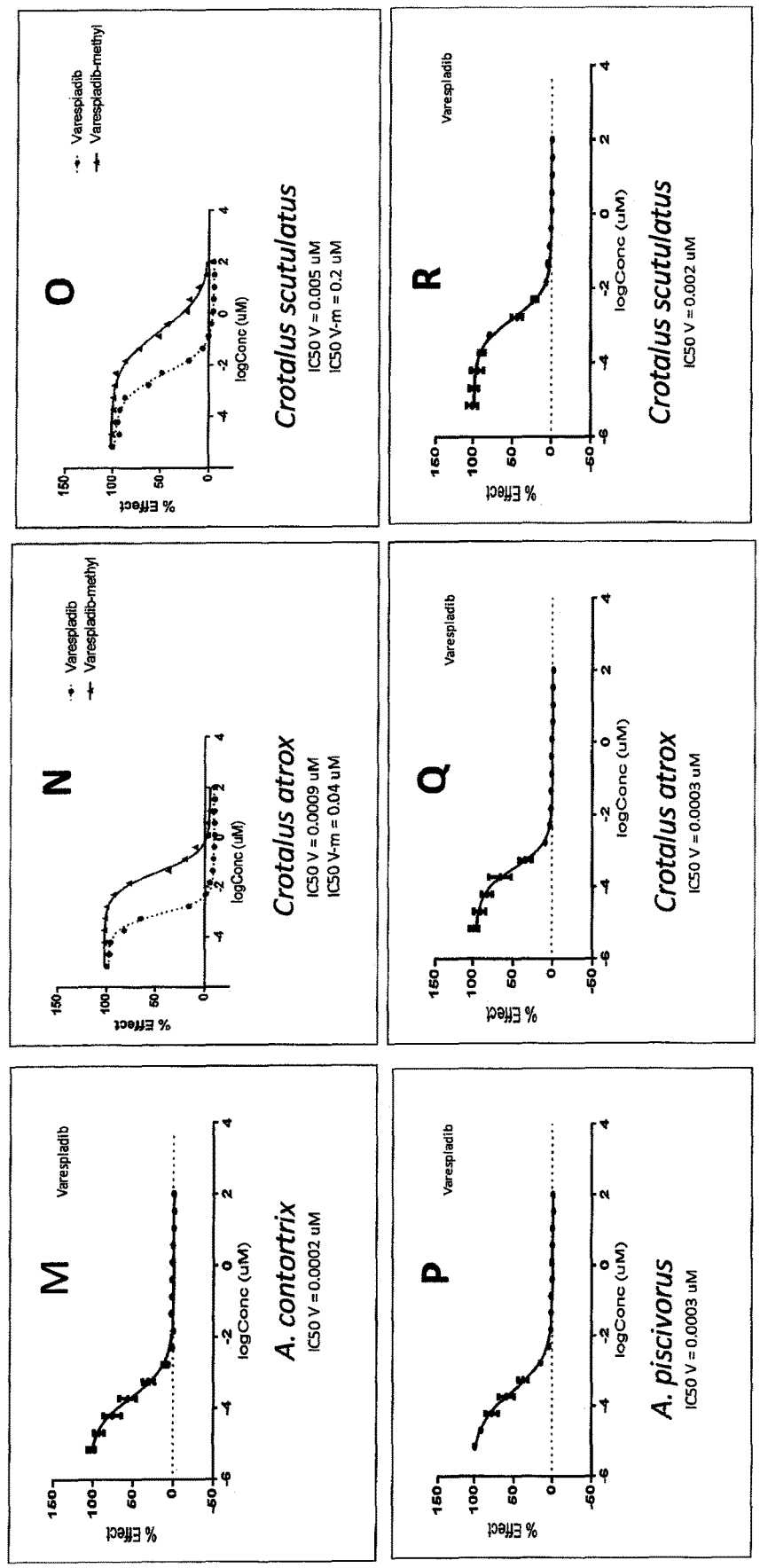

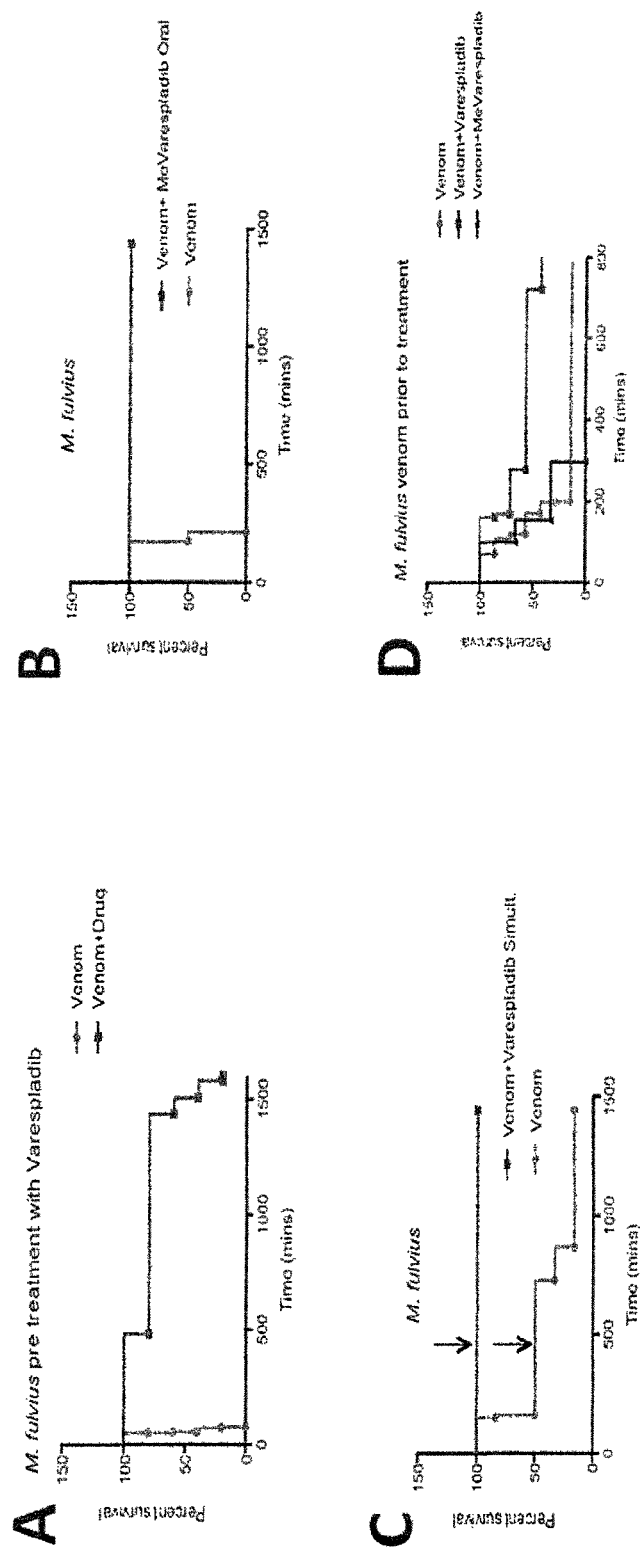
FIGURE 6A-D

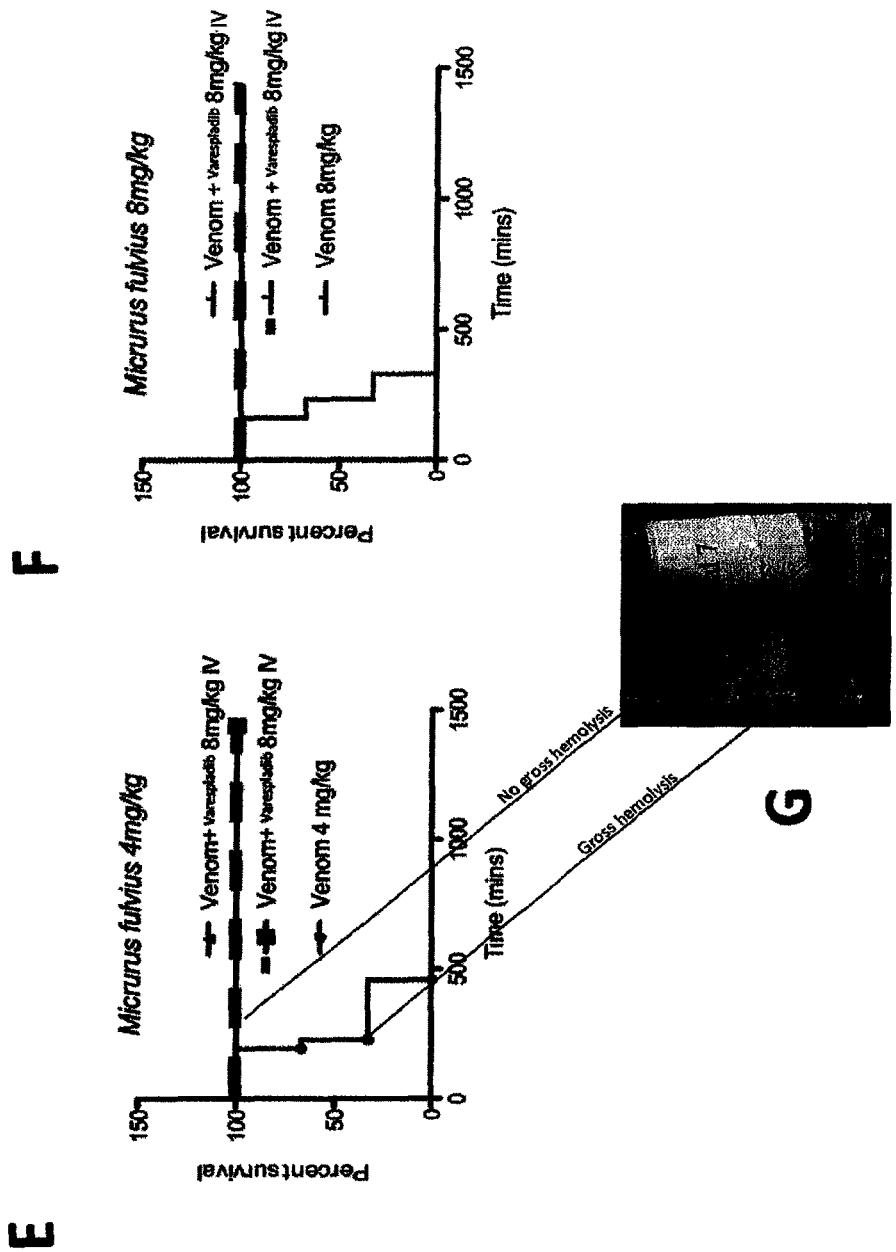
FIGURE 6E-G

FIGURE 6H

Prinomastat, batimastat and marimastat inhibition of elapid venoms *in vitro*

FIGURE 15 (TABLE 3)

Varespladib has unexpected breadth and potency against numerous medically important venoms, *in vitro*. $IC_{50}$ (uM) is based on assays for sPLA2 inhibition as detailed in Example 2.

| Venom | R-square | IC50uM |
|---|---|---|
| *Acanthophis antarcticus* | 0.994 | 0.0006 |
| *Agkistrodon blomhoffii brevicaudus* | 0.997 | 0.0005 |
| *Agkistrodon contortrix* | 0.985 | 0.0002 |
| *Agkistrodon piscivorus* | 0.991 | 0.0003 |
| *Bee Venom Control* | 0.948 | 13.25 |
| *Bitis gabonica* | 0.982 | 0.0003 |
| *Bothrops asper* | 0.990 | 0.0001 |
| *Bothrops jararaca* | 0.994 | 0.0002 |
| *Bungarus caeruleus* | 0.996 | 0.0001 |
| *Crotalus adamanteus* | 0.993 | 0.0002 |
| *Crotalus atrox* | 0.986 | 0.0003 |
| *Crotalus durissus terrificus* | 0.998 | 0.005 |
| *Crotalus scutulatus scutulatus* | 0.992 | 0.002 |
| *Dendroaspis polylepis* | 0.962 | ~0.0001 |
| *Echis carinatus* | 0.996 | 0.00006 |
| *Laticauda semifasciata* | 0.991 | 0.00006 |
| *Micrurus fulvius* | 0.998 | 0.001 |
| *Naja naja atra* | 0.975 | 0.0008 |
| *Naja naja kaouthia* | 0.995 | 0.00005 |
| *Naja naja naja* | 0.999 | 0.001 |
| *Notechis scutatus scutatus* | 0.959 | 0.00006 |
| *Ophiophagus hannah* | 0.999 | 0.003 |
| *Oxyuranus scutellatus* | 0.997 | 0.001 |
| *Pseudechis australis* | 0.997 | 0.003 |
| *Vipera berus* | 0.997 | 0.00002 |
| *Vipera russelli* | 0.999 | 0.0006 |

FIGURE 16 (TABLE 4)

Methylvarespladib (an orally available prodrug of varespladib) has unexpected potency against multiple snake venoms *in vitro*. $IC_{50}$ (uM) is based on assays for sPLA2 inhibition as detailed in Example 2 and suggests an unexpected strategy for treating snakebites immediately after a bite.

| Venom | R-square | IC50uM |
|---|---|---|
| *Agkistrodon blomhoffii brevicaudus* | 0.996 | 0.04 |
| *Bee venom* | indeterminate | indeterminate |
| *Bungarus caeruleus* | 0.999 | 0.02 |
| *Bungarus fasciatus* | 0.985 | 0.02 |
| *Crotalus adamanteus* | 0.997 | 0.02 |
| *Crotalus atrox* | 0.996 | 0.04 |
| *Crotalus durissus terrificus* | 0.994 | 0.26 |
| *Crotalus scutulatus scutulatus* | 0.994 | 0.21 |
| *Dendroaspis polylepis* | 0.973 | 0.02 |
| *Echis carinatus* | 0.998 | 0.01 |
| *Laticauda semifasciata* | 0.950 | 0.02 |
| *Micrurus fulvius* | 0.998 | 0.08 |
| *Naja naja atra* | 0.970 | 0.01 |
| *Naja naja kaouthia* | 0.988 | 0.02 |
| *Naja naja naja* | 0.997 | 0.02 |
| *Notechis scutatus scutatus* | 0.964 | 0.03 |
| *Ophiophagus hannah* | 0.996 | 0.01 |
| *Oxyuranus scutellatus* | 0.989 | 0.01 |
| *Pseudechis australis* | 0.987 | 0.09 |
| *Vipera berus* | 0.975 | 0.03 |
| *Vipera russelli* (Daboia) | 0.993 | 0.02 |

FIGURE 17 (TABLE 5)

Prinomastat has broader spectrum activity against snake venom metalloproteinases than previously reported. $IC_{50}$ (uM) is based on assays for MMP inhibition as detailed in Example 2. It is envisioned that prinomastat could be strategically paired with varespladib for parenteral administration or methylvarespladib for oral adminstation and an effective strategy for needle-free, time-of-bite, treatment.

| Venom | R-square | IC50uM |
|---|---|---|
| *Agkistrodon blomhoffii brevicaudus* | 0.997 | 0.02 |
| *Agkistrodon contortrix* | 0.983 | 0.06 |
| *Agkistrodon piscivorus* | 0.986 | 0.02 |
| *Bitis gabonica* | 0.997 | 0.03 |
| *Bothrops asper* | 0.998 | 0.06 |
| *Bothrops jararaca* | 0.998 | 0.05 |
| *Crotalus adamanteus* | 0.995 | 0.12 |
| *Crotalus atrox* | 0.98 | 0.02 |
| *Crotalus durissus terrificus* | 0.994 | 0.01 |
| *Crotalus scutulatus scutulatus* | 0.921 | 0.002 |
| *Echis carinatus* | 0.953 | 0.02 |
| *Gloydius brevicaudus* | 0.987 | 0.03 |
| *Micrurus fulvius* | 0.982 | 0.12 |
| *Naja naja naja* | 0.999 | 0.1 |
| *Pseudechis australis* | 0.999 | 1.3 |
| *Trimeresurus elegans* | 0.998 | 0.16 |
| *Vipera berus* | 0.999 | 0.22 |
| *Vipera russelli* | 0.98 | 0.16 |

Figure 18 (Table 6)

Marimastat has broader spectrum activity against snake venom metalloproteinases than previously reported. $IC_{50}$ (uM) is based on assays for MMP inhibition as detailed in Example 2. It is envisioned that marimastat administration could be strategically paired with varespladib for parenteral administration or methylvarespladib for oral adminstation and an effective strategy for needle-free, time-of-bite, treatment.

| Venom | R-square | IC50uM |
|---|---|---|
| *Agkistrodon blomhoffii brevicaudus* | 0.997 | 0.04 |
| *A. calloselasma rhodostoma* | 0.992 | 0.04 |
| *Agkistrodon contortrix* | 0.968 | 0.06 |
| *Agkistrodon piscivorus* | 0.959 | 0.04 |
| *Bitis gabonica* | 0.993 | 0.03 |
| *Bothrops asper* | 0.994 | 0.14 |
| *Bothrops jararaca* | 0.994 | 0.06 |
| *Crotalus adamanteus* | 0.985 | 0.16 |
| *Crotalus atrox* | 0.997 | 0.03 |
| *Crotalus durissus terrificus* | 0.996 | 0.01 |
| *Echis carinatus* | 0.92 | 0.04 |
| *Naja naja naja* | 0.995 | 0.13 |
| *Trimeresurus elegans* | 0.993 | 0.22 |
| *Vipera berus* | 0.991 | 0.22 |
| *Vipera russelli* | 0.989 | 0.23 |

FIGURE 19 (Table 7)

Batimastat has broader spectrum activity against snake venom metalloproteinases than previously reported. $IC_{50}$ (uM) is based on assays for MMP inhibition as detailed in Example 2. It is envisioned that batimastat administration could be strategically paired with varespladib for parenteral administration as an effective strategy for the treatment of snakebite.

| Venom | R-square | IC50uM |
|---|---|---|
| *Acanthophis antarcticus* | 0.999 | 1.21 |
| *Agkistrodon blomhoffii brevicaudus* | 0.999 | 0.03 |
| *Agkistrodon piscivorus* | 0.974 | 0.056 |
| *Bitis gabonica* | 0.998 | 0.084 |
| *Crotalus adamanteus* | 0.995 | 0.460 |
| *Crotalus atrox* | 0.961 | 0.031 |
| *Crotalus durissus terrificus* | 0.977 | 0.023 |
| *Crotalus scutulatus scutulatus* | 0.958 | 0.004 |
| *Echis carinatus* | 0.959 | 0.075 |
| *Micrurus fulvius* | 0.979 | 0.056 |
| *Trimeresurus elegans* | 0.998 | 0.49 |
| *Vipera berus* | 0.996 | 0.45 |

FIGURE 20, Table 8

Vorinostat, Ilomastat (fmr.fig.2C) Gabexate, Nafamostat have broader spectrum activity against snake venom metalloproteinases than previously reported. Surprisingly, SPIs gabexate and nafamostat have a significant effect on some snake venom metalloproteinase activity. $IC_{50}$ (uM) is based on assays for MMP inhibition as detailed in Example 2. It is envisioned that these drugs are administered parenterally or orally alone or in combination with varespladib-based therapies for the effective treatment of snakebite.

| Vorinostat | | |
|---|---|---|
| Venom | R-square | IC50uM |
| *Agkistrodon blomhoffii brevicaudus* | 0.971 | 20.0 |
| *Agkistrodon contortrix* | 0.89 | 22.2 |
| *Agkistrodon piscivorus* | 0.942 | 27.0 |
| *Bitis gabonica* | 0.986 | 10.9 |
| *Bothrops asper* | 0.992 | 4.5 |
| *Crotalus adamanteus* | 0.798 | 25.6 |
| *Crotalus atrox* | 0.991 | 15.8 |
| *Crotalus durissus terrificus* | 0.98 | 24.89 |
| *Echis carinatus* | 0.885 | 21.5 |
| *Gloydius brevicaudus* | 0.947 | 25.3 |
| *Trimeresurus elegans* | 0.984 | 38.0 |
| *Vipera berus* | 0.991 | 22.3 |
| Gabexate | | |
| *Agkistrodon blomhoffii brevicaudus* | 0.996 | 6.6 |
| *Agkistrodon contortrix* | 0.932 | 11.95 |
| *Agkistrodon piscivorus* | 0.952 | 1.4 |
| *Bothrops jararaca* | 0.996 | 18.5 |
| *Crotalus adamanteus* | 0.995 | 1.6 |
| *Crotalus durissus terrificus* | 0.96 | 0.25 |
| *Echis carinatus* | 0.995 | 3.2 |
| *Gloydius brevicaudus* | 0.999 | 2.63 |
| *Gloydius brevicauds(2)* | 0.993 | 1.21 |
| *Oxyuranus scutellatus* | 0.993 | 10.4 |
| Nafamostat | | |
| *Agkistrodon blomhoffi brevicaudis* | 0.992 | 2.28 |
| *Agkistrodon piscivorus* | 0.978 | 114.8 |
| *Bothrops jararaca* | 0.995 | 4.33 |
| *Crotalus adamanteus* | 0.995 | 2.69 |
| *Crotalus atrox* | 0.896 | 37.2 |
| *Crotalus durissus terrificus* | 0.96 | 3.4 |
| *Echis carinatus* | 0.999 | 5.7 |
| *Gloydius brevicaudus* | 0.979 | 1.05 |
| *Oxyuranus scutellatus* | 0.953 | 0.030 |

ENVENOMATION THERAPIES AND RELATED PHARMACEUTICAL COMPOSITIONS, SYSTEMS AND KITS

CROSS-REFERENCE TO RELATED APPLICATIONS

This application is a United States national phase patent application based upon international patent application no. PCT/US2015/061834 filed Nov. 20, 2015, which claims priority to provisional application No. 61/743,705, filed Sep. 10, 2012; provisional application No. 61/771,750, filed Mar. 1, 2013; provisional application No. 61/824,087, filed May 16, 2013; and provisional application No. 61/857,032, filed Jul. 22, 2013. The entire content of each of the aforementioned applications is incorporated herein by reference.

FIELD OF THE INVENTION

The invention relates to methods and compositions for treatment of envenomation such as snakebite evenomation, and finds application in the fields of medicine, public health and veterinary medicine.

BACKGROUND OF THE INVENTION

Venoms are a subset of poisons with simple or complex compositions that are generally injected by fang, stinger, spine or projectile containing toxins to immobilize and kill prey or as a means of defense against predators or rivals. Venom is generally delivered to a victim by bite or insertion of a sharp body feature. Although many venoms cause only discomfort, some venoms are highly poisonous and can result in a victim's death, amputation of a limb or permanent disfigurment. Examples of venomous animals include invertebrates (e.g., black widow spiders, box jellyfish, and cone snails), fish (e.g., stonefish and other members of the family Scorpaenidae) and reptiles (e.g., snakes and beaded lizards). Notably, venomous snakebites are a major public health problem in many countries and occur on all continents except Antarctica.

There may be more than five million instances of snakebite per year worldwide, of which as many or more than 400,000 result in severe sequelae. As many as 125,000 deaths and many more permanent disabilities may result from snakebite. It is estimated that over 40,000 snakebite victims (mostly young) die each year in India. In the U.S., about 8,000 venomous snakebites occur each year, and more than 1,500 snakebites per year in Australia are from highly neuro- and hemotoxic snake envenomations despite the absence of vipers from the continent. See Alirol et al., 2010, "Snakebite in South Asia: A Review" *PLoS Negl Trop Dis.* 4(1): e603; and Kasturiratne et al., 2008, "The global burden of snakebite: a literature analysis and modeling based on regional estimates of envenoming and deaths," *PLoS Med.* 5:e218.

Variation in venom composition is a ubiquitous phenomenon in snakes and occurs both interspecifically and intraspecifically, limiting cross-reactivity of antivenoms with the venoms of snake for which their use is intended and even more so the more removed the snake is phylogenetically from the antivenom of origin. Venom variation can have severe outcomes for snakebite victims by rendering the specific antibodies found in antivenoms ineffective against heterologous toxins found in different venoms. Casewell, et al., "Medically important differences in snake venom composition are dictated by distinct postgenomic mechanisms", *Proceedings of the National Academy of Sciences* 111.25 (2014): 9205-9210. The high variability of the composition and external structural features of snake venoms even within the same species of snake—or even the same individual snake—renders the development of broadly effective antivenoms infeasible.

Many venoms include components that interrupt acetylcholine transmission between nerve and muscle paralyzing skeletal muscles by interfering with transmission or destroying the nerve endings, themselves rendering all treatments except advanced life-support ineffective. Many venoms destroy muscle, connective tissues and skin while others cause severe and often fatal disturbances of bleeding and clotting—or combinations of all these effects (e.g. Many elapid venoms such as those of coral snakes, taipan and cobras and those of vipers such as Russell's viper, European viper and rattlesnake are commonly simultaneously hemo/cytotoxic and neurotoxic). Venoms are often complex mixtures of enzymatic and non-enzymatic toxins with different activities combining, for example, neurotoxicity with hemo- or myo-toxicity.

Although antivenoms are sometimes available, their value in treating victims can be limiting for a variety of reasons. First, venoms even within the same species of snake can vary dramatically in composition and action even within the same, individual snake based on its diet and geographical location. Snakes of the same species separated only by geography can have vastly different venom composition such that a snake species in one part of India (e.g. *Daboia russelli*) kills primarily by causing bleeding disturbances but in another part of India is more neurotoxic. Similarly, the venom of the European viper (e.g. *Vipera berus*) can vary such that in some cases the venom is more neurotoxic and in other cases cyto-hemotoxic. In North America, the rates of recurrence of signs and symptoms following initial antivenom treatment requires a higher incidence of re-treatment varying by region. In many instances, if polyvalent antivenom is not available, the snake's identity becomes important so the appropriate anti-venom can be used, but even the correct identification of the animal does not guarantee that an antivenom has been developed. In this instance, the closest matching or "paraspecific" antivenom is used as the best approximation but is frequently ineffective while incurring complications and severe financial burden.

Second, in some cases, such as for North American coral snakes (monospecific) or African snakes (polyvalent), antivenom have been taken off the market. In sub-Saharan Africa, these important commercial preparations have become scarce because manufacturers have decided to discontinue them. In 2015, *Médecins Sans Frontières* (*MSF, Doctors Without Borders*) put increased availability of snakebite treatments on its global "Wishlist" (Facebook) and worldwide news reported that much of the continent of Africa would run out of effective antivenom therapies in 2016 and stating (e.g. MSF press releases 4 and 8 Sep. 2015) "*Tens of thousands of people will continue to die of snakebite unnecessarily unless the global health community takes action to ensure treatment and antivenom is made available.*"

Third, and perhaps most importantly, even if the venom's source has been identified and a corresponding antivenom exists, the likelihood that the victim has ready access to the anti-venom is exceedingly low or is economically unaffordable such that victims would rather risk dying than seeking expensive medical care. It has been estimated that more than 75% of deaths by snakebite occur outside the hospital setting, often in the field. Most antivenoms are readily perishable and not generally available outside of a hospital setting because of the cold chain requirements and the high rates of severe adverse reactions requiring either prophylactic or acute care management (e.g. anaphylaxis). Moreover, because venomous bites often occur in remote locations far from population centers, the victim is not likely to be able to reach a hospital in time to receive the needed treatment after symptoms have set in. Thirdly, antivenom cannot effectively penetrate through tissues already damaged by venom because the physical properties of blood clots and necrotic tissue do not allow this and antivenom can only neutralize circulating venom or that with which it comes in direct contact by other means. Antivenom is generally considered ineffective in the setting of neurotoxin-induced pathology because of its inability to penetrate peripheral and central nervous system tissues. Rather, life-support measures such as mechanical ventilation save these patients in most cases. The invention can reduce ICU costs and decrease the overall cost of care to individuals and society by reducing the need for these interventions and can be used as first-line therapy for snakebite by any route of administration alone, co-adminstered or co-formulated with other known interventions such as antivenom.

In addition to antivenom, complementary approaches have been tried to manage snakebite. The acetylcholinesterase inhibitor edrophonium has been administered intravenously for management of snakebite (Warrell et al., 1983, "Severe neurotoxic envenoming by the Malayan krait *Bungarus candidus* (Linnaeus): response to antivenom and anticholinesterase," *Br Med J (Clin Res Ed)* 286(6366):678-80; Watt et al., 1986, "Positive response to edrophonium in patients with neurotoxic envenoming by cobras (*Naja naja philippinensis*). A placebo-controlled study" *N Engl J Med.* 315(23):1444-8; and Currie et al., 1988, "Resolution of neurotoxicity with anticholinesterase therapy in death-adder envenomation. *Med. J. Aust.* 148:522-525). Matrix metalloproteinase inhibitors (MPIs) and phospholipase A2 inhibitors (PLAI2) have been proposed as potential therapies, but effective, broad-spectrum examples have not been identified Villalta-Romero et al. *ACS Med Chem Lett* 2012, 3, 540-543 and Marcusi et al. *Snake venom phospholipase A2 inhibitors. Current Topics in Medicinal Chemistry,* 2007.

Versatile antivenom snakebite therapies have proven elusive since the outer structures of venomous molecules are highly variable and are known to present a difficult and inefficient target for antivenom. Even more elusive has been the development of pharmacological snakebite therapies with either specific or broad-spectrum efficacy for snakebite envenomation. Thus, there is a clear, unmet need for effective and economical snakebite therapies that can be given in timely fashion. The high cost of antivenom and treatment of snakebite, generally, meets the World Health Organization's definition of a "catastrophic healthcare expense" and because of the limited efficacy of current snakebite treatments- and anticipated financial ruin. Thus the decision to be treated or not to be treated for snakebite poses a dilemma whatever the victim decides to do resulting in often deadly or disabling indecision. Further, many governments are unable or are reluctant to subsidize the production of therapies that are perceived as ineffective and outdated or seek low cost, ineffective antivenoms causing pharmaceutical companies to withdraw from marketing more effective but expensive antivenoms. Traditional serum derived antivenom cannot be safely administered outside of the hospital. An affordable, broad-spectrum, first line antidote to snakebite would have an immediate positive impact on the health of millions of people who are at risk of suffering life and limb-threatening snakebites.

SUMMARY OF THE INVENTION

The inventor has identified versatile therapeutic regimens and related pharmaceutical compositions, systems and kits that rapidly and effectively treat envenomation-damaged tissue and a broad spectrum of associated sequelae, most significantly, immediate life-threat from neurotoxin mediated death and hematological catastrophe. Methods and pharmaceutical compositions of the invention are effective against every snake venom PLA2 enzyme irrespective of snake species and in other instances, the effects of other venom elements directly and indirectly—as well as host systems reducing the likelihood of catastrophic coagulopathies, tissue damage and kidney failure, among other venom-induced pathologies. This renders both enzymatic and non-enzymatic venom components less harmful while blunting the victim's own pathological responses of venom effects. This surprising finding leads to the development of the first ever field-treatment for snakebite that could be administered by a person with limited skill, outside of a hospital setting and, similarly, the first ever opportunity since the invention of antivenom to establish clinical equipoise in the use and testing of antivenoms when these compositions are used as first line therapy in the field or hospital setting, enabling traditional antivenoms to be improved in a systematic and scientifically sound manner. Furthermore, that some of these antidote compositions could be administered orally to produce therapeutically effective concentrations of drug in the blood even before arriving at the hospital is a monumental advance for survivability and complication reduction, especially when combined with an effective MP, SP or multifunctional inhibitor of snake and host enzymes that have complex interplay in snakebite pathology.

Significantly, pharmaceutical compositions of the present invention, unlike antivenom, will more readily penetrate through venom-damaged tissue and nerve terminals, including neuromuscular junctions, effecting far more rapid and favorable results than antivenom. The physical properties of antivenom itself, blood clots, necrotic tissue and nerve tissue restrict such penetration by antivenom, with the result that antivenom typically only neutralizes circulating venom or venom with which it comes in direct contact by other means. The present invention addresses those limitations and in certain embodiments, when combined with antivenom therapy as first-line therapy or coformulation, renders antivenom far more effective than when used alone.

Thus, in one embodiment, the present invention relates to a method for the use of at least one PLA2 inhibitor (usually an sPLA2 inhibitor) compound, preferably a 1H-indole-3-glyoxylamide (More generically a 3-glyoxamide, less generically and more specifically a 1H-indole-3-glyoxamide defined in the art as 1H-indole-3-glyoxamides; U.S. Pat. No. 5,654,326) such as varespladib and/or methylvarespladib for the treatment of envenomation (e.g., a venomous animal bite or sting such as from a snake, lizard, amphibian, scorpion, spider, or other invertebrate bite or sting as otherwise defined herein) involving administration of an effective amount of sPLA2 inhibitor compound within a specific time interval, preferably immediately or as soon as possible after the envenomation to about 6 hours or more (at least within about 24 hour period, and often within about a 12 hour period) after envenomation. In one aspect, the present invention is directed to a method of treating or reducing the likelihood of death, long-term injury and reducing the need for antivenom therapies and hospital resources in a patient having suffered envenomation by administering at least one sPLA2 inhibitor, alone or in combination with one or more additional bioactive agents, by one or more routes of delivery immediately or as soon as is possible after envenomation (often no more than 24 hours, even more often no more than 12 hours, preferably no more than about 6 hours, even more preferably no more than about 1 hour, even more often immediately after the realization that the patient has been subjected to envenomation) and for a period of time as long as it takes to have the patient taken to a hospital or other point of care facility for further diagnosis and/or treatment. Optionally, therapy is provided for a day to several weeks afterwards by one or more routes of delivery and formulation depending upon the setting and condition of the patient.

In an alternative embodiment, the present invention is also directed to a method for using a PLA2 inhibitor compound, preferably varespladib and/or methylvarespladib alone or in combination with other compounds which inhibit PLA2 (most commonly sPLA2) or other venom components such as metalloproteinases (MPs) and/or serine proteases (SPs) for the treatment of envenomation wherein an effective amount of the active agent is administered immediately (at about 0 hours or as soon thereafter as is possible after envenomation and continued as needed for about 1 to 7 days or until a medically determined stopping point is reached. In one approach the method comprises administering an effective an amount of a composition as described herein until harmful sPLA2 or MP activity levels are reduced, blood counts and coagulation factors normalize and the victim exhibits sustained improvement in signs or symptoms of envenomation followed by treatment or retreatment with alternative compositions, especially including traditional anti-venom compositions.

The present invention relates to a method for the use of individual or combinations of venom inhibitor compounds to inhibit PLA2 or other venom components such as metalloproteinases (MPs) and/or acetyicholinsterases by injection or other route of administration (i.e., not by injection), together or separately for the treatment of envenomation wherein the active ingredients are administered immediately (at about 0 hour) or as soon as is possible to about 6 hours after bite or sting and continued for about 1 to 7 days or until a medically determined stopping point based upon objective or clinical measures is reached, often related to confirmation or suspicion of envenomation. That stopping point may be at the time a patient is diagnosed and/or treated at a hospital or other point of care facility or it may be for a substantially extended period of several weeks (e.g., about 1-3 weeks or more) in order to allow the patient to fully recover from the envenomation.

The present invention provides PLA2 inhibitors, combinations of PLA2 inhibitors, optionally with one or more inhibitors of metalloproteinases (MPs), acetylcholinesterase and/or other venom components to a patient to mitigate the effects of envenomation causing the injurious conditions associated with venom injection. In some embodiments, the compound is an inhibitor of more than one component of snake venom. In some embodiments, the sPLA2 inhibitors, especially those which are based on 1-H-indole-3-glyoxylamide chemical structures and which include varespladib and methylvarespladib are used alone or in combination with each other and/or other agents as otherwise described herein.

The present invention also is directed to a method for the treatment or prevention of death, long-term injury and reduction in the need for (or augmentation of) antivenom therapies, blood and clotting replacement therapies, dialysis and hospital resources in a patient having suffered envenomation by administering a composition as otherwise described herein within 0 (i.e., immediately or as soon as possible) to 24 hours after a bite or sting or prior to a rise in sPLA2 levels, other correspondingly abnormal laboratory values which evidence that envenomation has occurred and/or clinical signs or symptoms suggestive of venom toxicity.

The present invention also is directed to a method of reducing the likelihood of death or injury from envenomation in a mammal including a human, the method comprising initiating administration to a patient suspected of having or known to have suffered envenomation, the method comprising administering an effective amount of a multifunctional inhibitor compound (e.g., varespladib or methylvarespladib) or a combination of compounds (which may include varespladibe and/or methylvarespladib) administered together or separately after envenomenation, but prior to the occurrence of injury, especially substantial injury, caused by local, regional or systemic envenomation.

The present invention further relates to a method of treating envenomation wherein treatment of a patient with a therapeutically effective amount of a composition according to the present invention, comprising administering at least one PLA2 inhibitor (e.g., sPLA2 inhibitor) compound to the patient within a time interval initiating from suspected or confirmed envenomation, objective or clinical suspicion of elevated sPLA2 levels or other indicators of envenomation by field, pre-hospital, laboratory, bedside or clinical testing, in preferred embodiments to mitigate or reduce the need for traditional antivenom and/or to reduce the cost and requirement for hospital, especially, clinically intensive resources such as intensive care (ICU time).

In one embodiment, the invention provides a method of treating a subject who suffers from an envenomation (as otherwise described herein, resulting, e.g., from a bite by a snake, other reptile, amphibian, arthropod, mollusk, cnidarian or coelenterate, among others), the method comprising administering (preferably, orally or by injection to the subject) a therapeutically effective amount of at least two, and in certain embodiments, no more than two active ingredients selected from the group consisting of a $PLA_2$ inhibitor as otherwise described herein, a metalloproteinase inhibitor, a serine protease inhibitor, an acetylcholinesterase inhibitor (AChEI or direct nicotinic receptor agonist such as nicotine paired with an anticholinergic agent), a spreading factor inhibitor (to reduce the likelihood that the active agent will distribute beyond the impacted tissue in the patient and including, unexpectedly, varespladib and methylvarespladib in this group) and a NMDA receptor antagonist (e.g. dizocilpine (MK-801)), wherein the active ingredient(s) may be administered together in mixtures or separately (individually), simultaneously, concurrently or sequentially.

Preferably, the aforementioned active ingredient(s) is/are administered (at least initially) by injection via needle or propulsion without a needle (e.g. jet injector or by aerosol administration) or orally, with further dosages of active ingredients being provided by any number of routes of administration in order to maintain effective concentrations of active in the patient until such time as therapeutic intervention is halted for whatever reason, including the decision to place the patient on more traditional antivenom compositions, because the level of the activity is increasing in the patient to the upper levels of its therapeutic index or because the patient condition has resolved or at least equilibrated making further administration unnecessary.

Preferred additional therapeutic agents include antivenoms, injectable or topically applied acetylcholinesterase inhibitors with mAChR antagonists, antinausea agent or antibiotics (often, a cephalosporin, tetracycline or demeclocycline, among others), among others. Many of these additional therapeutic agents are inhibitors of major enzymatic and non-enzymatic (e.g. rattlesnake myotoxin) components present in snake and other venom.

In another embodiment, the invention provides a method of treating a subject who suffers from a snakebite or other envenomation, the method consisting essentially of the step of administering (preferably by injection or orally at least initially) to the subject a therapeutically effective amount of:

(1) at least one $PLA_2$ inhibitor as described herein, preferably at least one of varespladib, methylvarespladib, indoxam, methylindoxam or a pharmaceutically acceptable salt thereof and optionally, at least one additional therapeutic agent selected from the group consisting of a metalloproteinase inhibitor, a serine protease inhibitor, an acetylcholinesterase inhibitor (administered preferably by injection), a muscarinic acetylcholine receptor (mAChR) antagonist, a spreading factor inhibitor, a NMDA receptor antagonist, an L-aminooxidase inhibitor, a hyaluronidase inhibitor, an antivenom and an antibiotic; or (2) at least one $PLA_2$ inhibitor, preferably at least one of varespladib, methylvarespladib, indoxam, methylindoxam or a pharmaceutically acceptable salt thereof and at least one metalloproteinase inhibitor, and optionally one or more additional therapeutic agents selected from the group consisting of a serine protease inhibitor, an acetylcholinesterase inhibitor (e.g., sometimes administered or orally), a muscarinic acetylcholine receptor (mAChR) antagonist, a spreading factor inhibitor, a NMDA receptor antagonist, an L-aminooxidase inhibitor, a hyaluronidase inhibitor, an antivenom and an antibiotic; or (3) at least one $PLA_2$ inhibitor, preferably at least one of varespladib, methylvarespladib, indoxam, methylindoxam or a pharmaceutically acceptable salt thereof and at least one serine protease inhibitor and, optionally, one or more additional therapeutic agents selected from the group consisting of a metalloproteinase inhibitor, an acetylcholinesterase inhibitor (sometimes administered by injection or topically by nasal or ocular administration), a muscarinic acetylcholine receptor (mAChR) antagonist, a spreading factor inhibitor, a NMDA receptor antagonist, an L-aminooxidase inhibitor, a hyaluronidase inhibitor, an antivenom and an antibiotic; or (4) at least one $PLA_2$ inhibitor, preferably at least one of varespladib, methylvarespladib, indoxam, methylindoxam or a pharmaceutically acceptable salt thereof and at least one metalloproteinase inhibitor and at least one serine protease inhibitor and, optionally, one or more additional therapeutic agents selected from the group consisting of an acetylcholinesterase inhibitor, a muscarinic acetylcholine receptor (mAChR) antagonist, a spreading factor inhibitor, a NMDA receptor antagonist, an L-aminooxidase inhibitor, a hyaluronidase inhibitor, an antivenom and an antibiotic; or (5) at least one $PLA_2$ inhibitor, preferably at least one of varespladib, methylvarespladib, indoxam, methylindoxam or a pharmaceutically acceptable salt thereof and at least one acetylcholinesterase inhibitor (often administered by injection with a muscarinic acetylcholine receptor (mAChR) antagonist such as atropine or glycopyrrolate, and optionally, one or more additional therapeutic agents selected from the group consisting of at least one metalloproteinase inhibitor, at least one serine protease inhibitor, a NMDA receptor antagonist, a spreading factor inhibitor, an L-aminooxidase inhibitor, a hyaluronidase inhibitor, antivenom, and an antibiotic or (6) at least one $PLA_2$ inhibitor, preferably at least one of varespladib, methylvarespladib, indoxam, methylindoxam or a pharmaceutically acceptable salt thereof and one or more spreading factor inhibitors and, optionally, one or more additional therapeutic agents selected from the group consisting of at least one metalloproteinase inhibitor, at least one serine protease inhibitor, an acetylcholinesterase inhibitor, a muscarinic acetylcholine receptor (mAChR) antagonist, a NMDA receptor antagonist, an L-aminooxidase inhibitor, a hyaluronidase inhibitor, an antivenom and an antibiotic; or (7) at least one $PLA_2$ inhibitor, preferably at least one of varespladib, methylvarespladib, indoxam, methylindoxam or a pharmaceutically acceptable salt thereof, a NMDA receptor antagonist and, optionally, one or more additional therapeutic agents selected from the group consisting of at least one metalloproteinase inhibitor, at least one serine protease inhibitor, an acetylcholinesterase inhibitor, a muscarinic acetylcholine receptor (mAChR) antagonist, a spreading factor inhibitor, a NMDA receptor antagonist, an L-aminooxidase inhibitor, a hyaluronidase inhibitor, an antivenom and an antibiotic or (8) prinomastat, vorinostat, marimastat, nafamostat, ilomastat, doxycycline, a cephalosporin, tanomastat, batimastat or varespladib or methyl varespladib alone or in combination for the bites of snakes where varespladib or methyl varespladib are effective MP inhibitors (e.g. Russell's viper venom).

In certain preferred embodiments, the invention provides a method of treating a subject who suffers from an envenomation as otherwise described herein, often a snakebite, the method consisting essentially of the step of administering (preferably by injection) to the subject a therapeutically effective amount of:

(a) at least one $PLA_2$ inhibitor, preferably at least one of varespladib, methylvarespladib, indoxam, methylindoxam or a pharmaceutically acceptable salt thereof, and at least one further agent selected from the group consisting of N,N-dimethylcarbamoylmethyl,4-4-guanidinobenzoyloxy-phenylacetate (Camostat, camostate), ethyl-p[6-guanidino-hexanoyloxy]-benzoate methansulfonate (gabexate), DEDA and a metalloproteinase inhibitor (e.g. prinomastat, vorinostat, marimastat or batimastat) and an acetylcholinesterase inhibitor (AChEI) (e.g. neostigmine with atropine or glycopyrrolate); or (b) at least one PLA2 inhibitor, preferably at least one of varespladib, methylvarespladib, indoxam, methylindoxam or a pharmaceutically acceptable salt thereof, and at least one further agent selected from the group consisting of N,N-dimethylcarbamoylmethyl,4-4-guanidinobenzoyloxy-phenylacetate (Camostat, camostate), ethyl-p[6-guanidino-hexanoyloxy]-benzoate methansulfonate (gabexate), prinomastat, vorinostat, marimastat, batimastat, neostgmine and atropine; and (c) optionally, one or more additional therapeutic agents selected from the group consisting of a muscarinic acetylcholine receptor (mAChR) antagonist, a NMDA receptor antagonist, a spreading factor inhibitor, an antivenom, and an antibiotic.

In preferred embodiments of the methods, pharmaceutical compositions, systems and kits of the invention, the metalloproteinase inhibitor is prinomastat, vorinostat, and/or marimastat and the $PLA_2$ inhibitor is preferably at least one of varespladib, methylvarespladib, indoxam, methylindoxam or a pharmaceutically acceptable salt thereof.

In one embodiment, a subject who suffers from a snake bite envenomation is co-administered a PLA$_2$ inhibitor such as preferably at least one of varespladib, methylvarespladib, indoxam, methylindoxam or a pharmaceutically acceptable salt thereof or an analogue, derivative or a pharmaceutically acceptable salt, enantiomer, diastereomer, solvate or polymorph thereof, N,N-dimethylcarbamoylmethyl,4-4-guanidinobenzoyloxy-phenylacetate (Camostat, camostate), ethyl-p[6-guanidinohexanoyloxy]-benzoate methansulfonate (gabexate), or a pharmaceutically acceptable salt, enantiomer, diastereomer, solvate or polymorph thereof, and a metalloproteinase inhibitor such as prinomastat, vorinostat, batimastat and/or marimastat, or an analog derivative, pharmaceutically acceptable salt, enantiomer, diastereomer, solvate or polymorph thereof, and, optionally, one or more additional therapeutic agents selected from the group consisting of an acetylcholinesterase inhibitor (e.g. neostgmine or atropine administered preferably by injection), a muscarinic acetylcholine receptor (mAChR) antagonist, an antivenom and an antibiotic, optionally in further combination with at least one spreading factor inhibitor.

In one embodiment, a subject who suffers from a snake bite envenomation is co-administered a PLA$_2$ inhibitor such as varespladib and/or methylvarespladib or an analog derivative, pharmaceutically acceptable salt, enantiomer, diastereomer, solvate or polymorph thereof, N,N-dimethylcarbamoylmethyl,4-4-guanidinobenzoyloxy-phenylacetate (Camostat, camostate), ethyl-p[6-guanidinohexanoyloxy]-benzoate methansulfonate (gabexate) and a serine protease inhibitor such as 4-(2-Aminoethyl) benzenesulfonyl fluoride, nafamostat or an analog derivative, pharmaceutically acceptable salt, enantiomer, diastereomer, solvate or polymorph thereof and, optionally, one or more additional therapeutic agents selected from the group consisting of an antivenom, an acetylcholinesterase inhibitor (e.g. neostgmine or pyridostigmine administered preferably by injection), a muscarinic acetylcholine receptor (mAChR) antagonist and an antibiotic optionally in combination with at least one spreading factor inhibitor.

In one embodiment, the present invention is directed to a method treating envenomation by administering to a subject in need of treatment an effective dose of a PLA2 inhibitor (preferably at least one of varespladib, methylvarespladib, indoxam, methylindoxam or a pharmaceutically acceptable salt thereof), optionally in combination with at least one additional agent, as described elsewhere herein. Surprisingly, administration of the therapeutic agent(s) prevents or rapidly reverses symptoms and signs of evenomation. As noted elsewhere herein, sequelae of evenomation include weakness, shortness of breath, bleeding, tingling, anxiety, respiratory paralysis, and death. Surprisingly, administration of the agents according to the invention within 6, usually with 2 hours after evenomation is nearly completely effective in preventing death even for otherwise fatal doses of the venom. Surprisingly, significant reversal or reduction of signs and symptoms of envenomation in said patient or subject is evident within few hours (e.g., about 2 hours) of administration. Surprisingly, effects of reversal may occur within 60 minutes or even within 30 minutes of administration. For example, nerve conduction, studies might return to at least 80% of normal within 8 hours. As another example, cessation or reduction of hemolysis may be observed within 2 hours—early administration may prevent these signs and symptoms of envenomation from occurring altogether.

Pharmaceutical compositions and methods according to the present invention may advantageously further include lidocaine and/or bupivacaine as agents to assist in the local distribution of the active(s) for further therapeutic benefit and analgesia while slowing the spread of venom by relaxation of lymphatic smooth muscle.

Methods, pharmaceutical compositions, systems and kits of the present invention treat, or reduce the likelihood of, one or more of neurotoxin-induced respiratory failure, cardiotoxicity, tissue and muscle destruction and/or venom-induced disseminated vascular coagulopathy, resulting in the patient having a substantially reduced likelihood of death and/or debilitating injury from an envenomation. Administration of the methods and pharmaceutical compositions described herein prevents the onset of a variety of life-threatening symptoms, including hemotoxin, cytotoxin, cardiotoxin or myotoxin-induced tissue damage, bleeding and clotting disorders, neurotoxin-induced respiratory failure, limb injury, kidney failure, multiple organ failure and/or cardiovascular collapse. In the case where one of the inhibitors is also an antibiotic and/or anti-inflammatory agent such as varespladib, the risk of infection is also reduced as are allergic and other acute complications resulting from anti-venom administration.

Certain embodiments of the invention treat or reduce the likelihood of neurotoxin-induced respiratory failure and tissue damage following envenomation by other venomous animals such as stonefish, lionfish, scorpions (e.g. *Centuroides* spp), spiders (e.g. *Loxosceles*) cone snails and tropical jellyfish by administering to a subject in need thereof:

(a) at least one PLA$_2$ inhibitor (preferably at least one of varespladib, methylvarespladib, indoxam, methylindoxam or a pharmaceutically acceptable salt thereof) and optionally (preferably) an SP or MP inhibitor; and (b) further optionally, one or more additional therapeutic agents selected from the group consisting of an acetylcholinesterase inhibitor (e.g. neostgmine or pyridostigmine administered preferably by injection), a muscarinic acetylcholine receptor (mAChR) antagonist, an antivenom, an antibiotic and spreading factor inhibitor.

A preferred pharmaceutical formulation of the invention comprises a therapeutically effective amount of:

(a) varespladib and/or methylvarespladib, preferably, varespladib, N,N-dimethylcarbamoylmethyl,4-4-guanidino-benzoyloxy-phenylacetate (Camostat, camostate), ethyl-p [6-guanidinohexanoyloxy]-benzoate methansulfonate (gabexate), or an analog derivative, pharmaceutically acceptable salt, enantiomer, diastereomer, solvate or polymorph thereof;

(b) either (1) prinomastat, vorinostat, batimastat and/or marimastat, or an analog derivative, pharmaceutically acceptable salt, enantiomer, diastereomer, solvate or polymorph thereof, and/or (2) 4-(2-Aminoethyl) benzenesulfonyl fluoride or an analog derivative, pharmaceutically acceptable salt, enantiomer, diastereomer, solvate or polymorph thereof; and (c) optionally, one or more pharmaceutically acceptable excipients.

Exemplary, non-limiting pharmaceutical compositions can be in the form of injectable solutions (which is preferred for initial treatment in combination with an auto or pen-injecting device), powders, liposomes, ointment, and aerosols and may include active ingredient(s) conjugated to another compound for specific targeting (e.g. nanoparticles). The pharmaceutical compositions described herein can be administered by a variety of techniques (e.g. through use of a manual or auto-injecting device that may be needle-based and that may optionally include a jet-injector, an intranasal drug delivery device, a nebulizer, a metered dose inhaler or a spray device or an oral formulation such as pills, tables or elixirs. Kits of the invention can include such compositions and devices, along with appropriate instructions and additional components (e.g. a mask). Compositions may also be in the form of lyophilized powders, which can be used to create injectable solutions for initial (and subsequent) treatment of an envenomated patient.

In one embodiment, the invention provides a pharmaceutical composition, preferably as a storage-stable, injectable, aerosolizable or dispersible pharmaceutical composition comprising a pharmaceutically acceptable diluent and a therapeutically effective amount of either:

(1) at least one $PLA_2$ inhibitor as described herein, preferably at least one of varespladib, methylvarespladib, indoxam, methylindoxam or a pharmaceutically acceptable salt thereof and optionally, at least one additional therapeutic agent selected from the group consisting of a metalloproteinase inhibitor, a serine protease inhibitor, an acetylcholinesterase inhibitor (all administered preferably by injection or orally or separately in either oral, topical or parenteral forms with or without antivenom), a muscarinic acetylcholine receptor (mAChR) antagonist, a spreading factor inhibitor, a NMDA receptor antagonist, an antivenom and an antibiotic; or (2) at least one $PLA_2$ inhibitor, preferably at least one of varespladib, methylvarespladib, indoxam, methylindoxam or a pharmaceutically acceptable salt thereof and at least one metalloproteinase inhibitor, and optionally one or more additional therapeutic agents selected from the group consisting of a serine proteinase inhibitor, an acetylcholinesterase inhibitor (administered preferably by injection), a muscarinic acetylcholine receptor (mAChR) antagonist, a spreading factor inhibitor, a NMDA receptor antagonist, an antivenom and an antibiotic; or (3) at least one $PLA_2$ inhibitor, preferably at least one of varespladib, methylvarespladib, indoxam, methylindoxam or a pharmaceutically acceptable salt thereof and at least one serine protease inhibitor and, optionally, one or more additional therapeutic agents selected from the group consisting of a metalloproteinase inhibitor, an acetylcholinesterase inhibitor (administered preferably by injection), a muscarinic acetylcholine receptor (mAChR) antagonist, a spreading factor inhibitor, a NMDA receptor antagonist, an antivenom and an antibiotic; or (4) at least one $PLA_2$ inhibitor, preferably at least one of varespladib, methylvarespladib, indoxam, methylindoxam or a pharmaceutically acceptable salt thereof and at least one metalloproteinase inhibitor and at least one serine protease inhibitor and, optionally, one or more additional therapeutic agents selected from the group consisting of an acetylcholinesterase inhibitor, a muscarinic acetylcholine receptor (mAChR) antagonist, a spreading factor inhibitor, a NMDA receptor antagonist, an antivenom and an antibiotic; or (5) at least one $PLA_2$ inhibitor, preferably at least one of varespladib, methylvarespladib, indoxam, methylindoxam or a pharmaceutically acceptable salt thereof and at least one acetylcholinesterase inhibitor (often administered injection) and/or muscarinic acetylcholine receptor (mAChR) antagonist, and optionally, one or more additional therapeutic agents selected from the group consisting of at least one metalloproteinase inhibitor, at least one serine protease inhibitor, a NMDA receptor antagonist, a spreading factor inhibitor, antivenom, and an antibiotic or (6) at least one $PLA_2$ inhibitor, preferably at least one of varespladib, methylvarespladib, indoxam, methylindoxam or a pharmaceutically acceptable salt thereof and one or more spreading factor inhibitors and, optionally, one or more additional therapeutic agents selected from the group consisting of at least one metalloproteinase inhibitor, at least one serine protease inhibitor, an acetylcholinesterase inhibitor, a muscarinic acetylcholine receptor (mAChR) antagonist, a NMDA receptor antagonist, an antivenom and an antibiotic; or (7) at least one $PLA_2$ inhibitor, preferably at least one of varespladib, methylvarespladib, indoxam, methylindoxam or a pharmaceutically acceptable salt thereof, a NMDA receptor antagonist and, optionally, one or more additional therapeutic agents selected from the group consisting of at least one metalloproteinase inhibitor, at least one serine protease inhibitor, an acetylcholinesterase inhibitor, a muscarinic acetylcholine receptor (mAChR) antagonist, a spreading factor inhibitor, a NMDA receptor antagonist, an antivenom and an antibiotic.

In another embodiment, the invention provides a reconstitutable pharmaceutical formulation comprising a lyophilized or freeze-dried mixture of one or more pharmaceutically acceptable excipients and a therapeutically effective amount of either:

(1) at least one $PLA_2$ inhibitor as described herein, preferably at least one of varespladib, methylvarespladib, indoxam, methylindoxam or a pharmaceutically acceptable salt thereof and optionally, at least one additional therapeutic agent selected from the group consisting of a metalloproteinase inhibitor, a serine protease inhibitor, an acetylcholinesterase inhibitor (administered preferably by injection), a muscarinic acetylcholine receptor (mAChR) antagonist, a spreading factor inhibitor, a NMDA receptor antagonist, an antivenom and an antibiotic; or (2) at least one $PLA_2$ inhibitor, preferably at least one of varespladib, methylvarespladib, indoxam, methylindoxam or a pharmaceutically acceptable salt thereof and at least one metalloproteinase inhibitor, and optionally one or more additional therapeutic agents selected from the group consisting of a serine proteinase inhibitor, an acetylcholinesterase inhibitor (administered preferably by injection), a muscarinic acetylcholine receptor (mAChR) antagonist, a spreading factor inhibitor, a NMDA receptor antagonist, an antivenom and an antibiotic; or (3) at least one $PLA_2$ inhibitor, preferably at least one of varespladib, methylvarespladib, indoxam, methylindoxam or a pharmaceutically acceptable salt thereof and at least one serine protease inhibitor and, optionally, one or more additional therapeutic agents selected from the group consisting of a metalloproteinase inhibitor, an acetylcholinesterase inhibitor (administered preferably by injection), a muscarinic acetylcholine receptor (mAChR) antagonist, a spreading factor inhibitor, a NMDA receptor antagonist, an antivenom and an antibiotic; or (4) at least one $PLA_2$ inhibitor, preferably at least one of varespladib, methylvarespladib, indoxam, methylindoxam or a pharmaceutically acceptable salt thereof and at least one metalloproteinase inhibitor and at least one serine protease inhibitor and, optionally, one or more additional therapeutic agents selected from the group consisting of an acetylcholinesterase inhibitor, a muscarinic acetylcholine receptor (mAChR) antagonist, a spreading factor inhibitor, a NMDA receptor antagonist, an antivenom and an antibiotic; or (5) at least one $PLA_2$ inhibitor, preferably at least one of varespladib, methylvarespladib, indoxam, methylindoxam or a pharmaceutically acceptable salt thereof and at least one acetylcholinesterase inhibitor (often administered injection) and/or muscarinic acetylcholine receptor (mAChR) antagonist, and optionally, one or more additional therapeutic agents selected from the group consisting of at least one metalloproteinase inhibitor, at least one serine protease inhibitor, a NMDA receptor antagonist, a spreading factor inhibitor, antivenom, and an antibiotic or (6) at least one PLA$_2$ inhibitor, preferably at least one of varespladib, methylvarespladib, indoxam, methylindoxam or a pharmaceutically acceptable salt thereof and one or more spreading factor inhibitors and, optionally, one or more additional therapeutic agents selected from the group consisting of at least one metalloproteinase inhibitor, at least one serine protease inhibitor, an acetylcholinesterase inhibitor, a muscarinic acetylcholine receptor (mAChR) antagonist, a NMDA receptor antagonist, an antivenom and an antibiotic; or (7) at least one PLA$_2$ inhibitor, preferably at least one of varespladib, methylvarespladib, indoxam, methylindoxam or a pharmaceutically acceptable salt thereof, a NMDA receptor antagonist and, optionally, one or more additional therapeutic agents selected from the group consisting of at least one metalloproteinase inhibitor, at least one serine protease inhibitor, an acetylcholinesterase inhibitor, a muscarinic acetylcholine receptor (mAChR) antagonist, a spreading factor inhibitor, a NMDA receptor antagonist, an antivenom and an antibiotic.

In one embodiment, the above-described compositions are reconstituted for administration to a patient or subject.

In one embodiment, the present invention is directed to the treatment of envenomation using a combination of an antivenom compound or composition ("an antivenom") as otherwise disclosed herein with a PLA2 inhibitor and/or a Metalloproteinase inhibitor and/or a Serine proteinase inhibitor. In one embodiment, the antivenom is combined with at least one compound selected from the group consisting of varespladib, methylvarespladib, prinomastat, marimostat, batimostat, vorinostat, camostat, gabexate and nafomostat or pharmaceutically acceptable salts thereof. In a preferred embodiment, the antivenom is combined with varespladib, methylvarespladib or a pharmaceutically acceptable salt thereof. In another embodiment, the antivenom is combined with at least one of varespladib, methylvarespladib or a pharmaceutically acceptable salt thereof and at least one of prinomastat, marimostat, batismastat or a pharmaceutically acceptable salt thereof. In another embodiment, the antivenom is Crofab®. The above combinations may be coadministered to a patient or subject in need at the same time, concurrently or sequentially.

In one embodiment, the present invention is directed to a pharmaceutical composition comprising at least one antivenom compound or composition in combination with at least one PLA2 inhibitor, Metalloproteinase inhibitor and/or Serine Proteinase inhibitor. The composition may be formulated and administered in one or more parts or in a single composition. In one embodiment, the antivenom is combined with at least one compound selected from the group consisting of varespladib, methylvarespladib, prinomastat, marimostat, batimostat, vorinostat, camostat, gabexate and nafomostat or pharmaceutically acceptable salts thereof. In a preferred embodiment, the antivenom is combined in a pharmaceutical composition with varespladib, methylvarespladib or a pharmaceutically acceptable salt thereof. In another embodiment, the antivenom is combined with at least one of varespladib, methylvarespladib or a pharmaceutically acceptable salt thereof and at least one of prinomastat, marimostat, batismastat or a pharmaceutically acceptable salt thereof. In another embodiment, the antivenom is Crofab™.

Notably, therapies of the invention provide varying combinations of snake specific, regionally specific and universally broad combinations that can be administered in multiple forms in sequence or individually before, during and after a bite, with or without accompanying hospitalization or antivenom treatment. This satisfies an unmet, long-felt need of extreme urgency. There is no existing effective field treatment or prophylaxis against envenomation—especially snakebite and it is estimated that more than 75% of deaths from envenomation, especially snakebite, occur outside the hospital. Traditional serum derived antivenom cannot be safely administered outside of the hospital. Hence, the invention provides the only existing plausible solution to this problem and meets a long-felt need in the art.

Furthermore, depending on the medical severity of the bite, treatments of the invention can be completely effective after a single emergency application of the drug or drug combinations in the field by the victim, a bystander or a minimally trained medical first responder, among others. Treatment regimens of the invention shorten hospital times, decrease the amount and cost of traditional serum derived antivenom needed for hospital- or emergency clinic-treated bites and can be given as first aid followed by maintenance therapy in oral, nasal or injection form for days or weeks after a bite in order to avoid the need for antivenom in many cases. These regimens lower morbidity, mortality and overall cost of envenomation, especially snakebite treatment.

In one example, a victim is bitten, self-injects, drinks an elixir or other orally bioavailable form, nasally sprays and/or administered by inhalation dosage form a composition of the invention, and thereafter proceeds to a hospital or other patient care facility for treatment with antivenom or observation (diagnosis and/or further treatment with a composition according to the present invention. Where symptoms are mild, compositions of the invention may be administered as a pill, liquid or spray form periodically (e.g. every 1, 2, 3, 4, 5, 6, 7, 8, 9, 10, 11, or 12 hours or even once daily in a sustained and/or controlled release form) until the body clears the venom (which may be from 1-10 or more days-up to about three weeks).

As there are no existing out-of-hospital pharmaceutical therapies for envenomation and no definitive treatments other than traditional antivenom, the invention satisfies a critical unmet clinical need. Further, treatment regimens of the invention are cost-effective, safe and can be transitioned from emergency therapy to outpatient or simplified hospital treatment.

Thus, the invention provides an affordable, widely-applicable antidote to snakebite and other venom-related injuries which will benefit millions of people who are at risk of suffering a life or limb-threatening envenomation. Notably, varespladib and methylvarespladib, the prodrug of varespladib are effective and have high potency against a broad range of venoms. Both show evidence of effect in some snake venom MP/SP enzymes and demonstrates utility in the immediate treatment of any snakebite as first-line therapy. Varespladib and methylvarespladib can be administered alone, coadministered or mixed with antivenom, MP inhibitors, SP inhibitors and other inhibitors or useful drugs as well as antivenom—in any order, formulation, or dosage form. There are multiple useful modes of delivery for both the drug and prodrug and combinations thereof with other pharmaceutically useful compositions.

BRIEF DESCRIPTION OF THE FIGURES

FIG. 5A-R Varespladib and methyl varespladib showed a high degree of potency against snake venom sPLA2 activity. Neither varespladib nor methylvarespladib has the same degree potency against bee venom sPLA2 (Example 6).

Figure 6H:
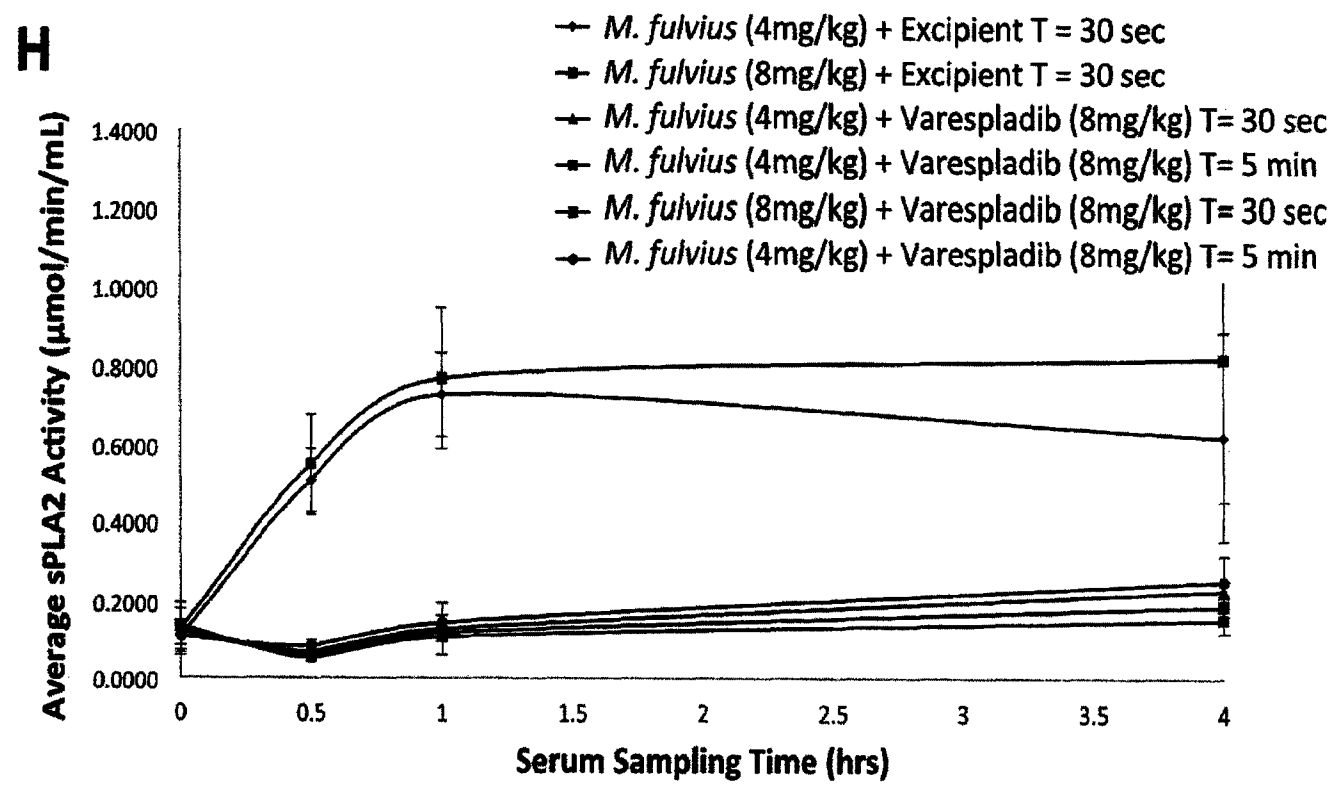

FIGS. 6A-H Varespladib is protective and therapeutically effective against lethal doses of *Micrurus fulvius* (coral snake) venom in mice and rats. Examples of in vivo testing of the present invention in mice and rats is shown. Administration of varespladib-based therapy before, simultaneously or after subcutaneous injection of high doses of *M. fulvius* venom showed survival advantage attributable to varespladib based therapy in mice and rats. Gross hemolysis was prevented by IV varespladib treatment and PLA2 levels were correspondingly suppressed by vaerspladib therapy in the same animals. 100% of rats given intravenous varespladib following subcutaneous administration of *M. fulvius* venom survived (Example 7).

FIG. 15, Table 3 shows IC50s for Varespladib sPLA2 inhibition (Example 12). Varespladib shows unexpected potency against multiple snake venoms (Example 12).

FIG. 16, Table 4 shows IC50s for Methylvarespladib sPLA2 inhibition. Methylvarespladib shows unexpected potency against multiple snake venoms (Example 12).

FIG. 17, Table 5 shows IC50s for Prinomastat-induced MP inhibition in vitro (Example 2). Prinomastat has broader spectrum activity against snake venom metalloproteinases than previously reported.

FIG. 18, Table 6 shows IC50s for Marimastat-induced MP inhibition in vitro.

FIG. 19, Table 7 shows IC50s for Batimastat-induced MP inhibition in vitro.

FIG. 20, Table 8 shows IC50s for Vorinostat, Ilomastat, Gabexate and Nafamostat-induced MP inhibition in vitro.

DETAILED DESCRIPTION OF THE INVENTION

I. Definitions

Figure 1:
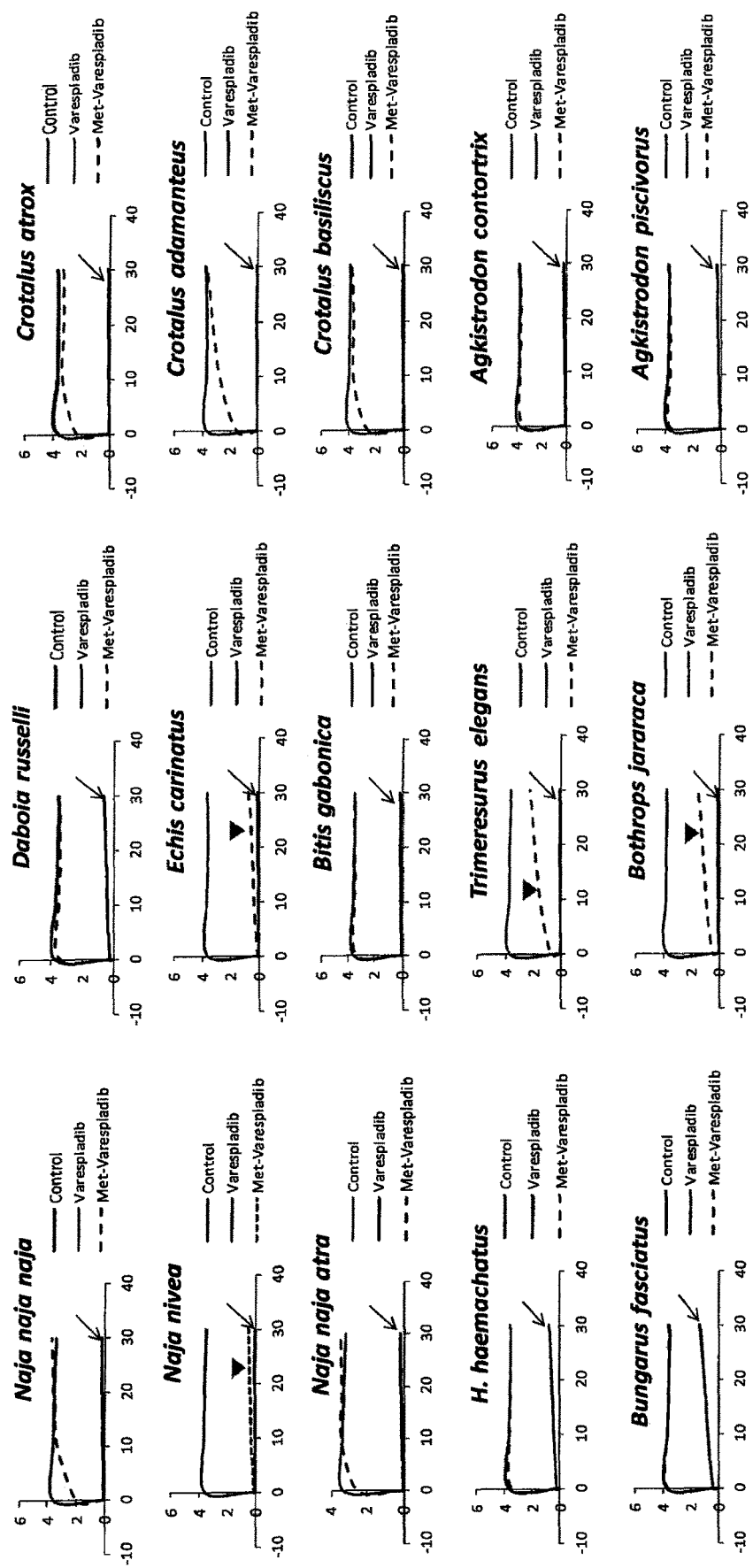
FIG. 1 Shows a time course of PLA2 activity when an excess of venom was combined with varespladib, methylvarespladib or venom alone (control). Both varespladib and methyl varespladib showed sustained inhibition of snake venom sPLA2 activity despite the extreme activity of excess venom (Example 3).

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As used herein, "AChE" is an abbreviation for acetylcholine; "AChEI" is an abbreviation for acetylcholinesterase inhibitor; "mAChR" is an abbreviation for muscarinic acetylcholine receptor; "nAChR" is an abbreviation for nicotinic acetylcholine receptor; Inhibitors of AChE that may also inhibit butyryl cholinesterases (BChE), pseudocholinesterases and others is implied. "MP" is an abbreviation for metalloproteinase (e.g., mammalian matrix metalloproteinase, MMPs, and snake venom metaloprotease, SVMPs; "SP" is an abbreviation for serine proteases; "MPI is an abbreviation for metalloproteinase inhibitor. Venoms (e.g., snake venoms) are secreted, and in the context of venoms "PLA2" and "sPLA2" are used interchangeably; PLA2-I is an abbreviation for phospholipase inhibitor; and "SPI" is an abbreviation for serine protease inhibitor.

Furthermore, the following terms shall have the definitions set out below.

The term "patient" or "subject" is used throughout the specification within context to describe an animal, generally a mammal, especially including a domesticated animal (e.g., dog, cat, cow, horse, sheep, goat, etc.) and preferably a human, to whom treatment, including prophylactic treatment (prophylaxis), with the compounds or compositions according to the present invention is provided. For treatment of those conditions or disease states that are specific for a specific animal such as a human patient, the term patient refers to that specific animal. In most instances, the patient or subject of the present invention is a human patient of either or both genders. Subjects contemplated for treatment according to the method of the invention include humans, companion animals, laboratory animals, livestock, horses and the like.

The term "effective" is used herein, unless otherwise indicated, to describe an amount of a compound or component which, when used within the context of its use, produces or effects an intended result, whether that result relates to the prophylaxis and/or therapy of an envenomation and/or disease state or conditions/symptom as otherwise described herein. The term effective subsumes all other effective amount or effective concentration terms (including the term "therapeutically effective") that are otherwise described or used in the present application. The term effective also includes periods of administration whether such administration represents a single administration, often orally or by injection or a single administration followed by hours, days or weeks of supplemental administration to a point where the administration is stopped because of clearance of the venom from the patient or the decision to institute alternative therapy, including the administration of a traditional serum-derived antivenom composition. It is noted that, in one aspect, the present invention is directed to administering an effective amount of a composition as described herein until harmful sPLA2 or MP activity levels are reduced, blood counts and coagulation factors normalize and the victim exhibits sustained improvement in signs or symptoms of envenomation. The administration may be followed by treatment or retreatment with alternative compositions, especially including traditional anti-venom compositions.

The term "compound" is used herein to describe any specific compound or bioactive agent disclosed herein, including any and all stereoisomers (including diasteromers), individual optical isomers (enantiomers) or racemic mixtures, pharmaceutically acceptable salts including alternative pharmaceutically acceptable salts, prodrug forms and deuterated or other isotopic substitutions. The term compound herein refers to stable compounds. Within its use in context, the term compound may refer to a single compound or a mixture of compounds as otherwise described herein. Compounds for use in the present invention may also include hydrates, solvates and/or polymorphs of the individual compounds. When a bioactive agent is disclosed for use in the present invention, it is understood that such term within the context of its use includes its pharmaceutically acceptable salts and/or alternative pharmaceutically acceptable salts unless specifically stated otherwise.

"Snakebite" includes "dry" snakebites as well as bites that result in envenomation or bite by non-venomous or unidentified snake. There are a number of ways to determine that a subject is a victim of a snake's bite. These include: the subject or another person witnessed the bite; physical evidence of snakebite (e.g., puncture wounds or lacerations, localized pain, local redness or swelling) is observed; the subject exhibits signs or symptoms consistent with snakebite envenomation (e.g., pain, redness, bleeding, or other evidence of envenomation such as weakness or paralysis); the subject exhibits signs or symptoms consistent with neurotoxic envenomation and has not been previously diagnosed with a condition other than neurotoxic envenomation that accounts for the signs or symptoms; venom or venom-activity has been detected (e.g., at the bite site, in urine or blood, using a snakebite venom/venom activity detection kit) or by assaying for elevated PLA2 activity. Visual identification of the snake may indicate that the subject has been bitten by a neurotoxic venomous snake even in the absence of fang or tooth marks (e.g. as with *Bungarus* bites).

"Signs" and "symptoms" of neurotoxic envenomation include paresthesia, drowsiness, dysconjugate gaze, small muscle paralysis which may result in ptosis (lid lag), weakness of neck muscles, dysphagia, mydriasis, fasiciculation, increased salivation, increased sweating, loss of muscle coordination, abdominal pain, difficulty speaking, nausea, difficulty swallowing and other bulbar palsies, and vomiting, hypotension, respiratory distress and respiratory muscle paralyses. In some cases the subject displays early signs of including early signs of neurotoxic envenomation, such as small muscle paralysis in the form of lid lag, dysconjugate gaze, difficulty swallowing and other bulbar palsies. Clinical assessments of muscle function of a subject who has suffered envenomation or who is suspected to have suffered envenomation include: visual acuity, ease of swallowing, ability to protrude the tongue, diction, and ability to raise the head completely off the bed for more than five seconds (neck flexion) and reduced peak respiratory flow "Venom" has its normal meaning and is a poisonous secretion of an animal, such as a snake, other reptile, amphibian, spider, scorpion, tick, cone snail, coelenterate (jelly fish), etc. transmitted by a bite or sting.

"Antivenom", "antivenin" or "antivenene" is a biological product used in the treatment of venomous bites or stings. Antivenom is generally created by milking venom from a venomous vertebrate such as a snake, lizard or fish or extracting it from an invertebrate such as a spider, tick, insect, coelenterate or mollusk. The venom is then diluted and injected into a horse, sheep, rabbit or goat or chicken eggs. The subject animal or egg will undergo an immune reaction to the venom, producing antibodies against the venom's antigenic molecules which can then be harvested from the animal's blood, refined and used to treat envenomation. Internationally, antivenoms must conform to the standards of the pharmacopoeia and the World Health Organization. "Paraspecific" antivenoms are those with actions or properties in addition to the specific one considered medically useful (e.g. to determine the paraspecific actions of an antivenom).

"Envenomation," refers to injection of venom into a victim as a result of a bite by a reptile, amphibian, arthropod, mollusk, cnidarian, insect, coelenterate or other venomous vertebrate or invertebrate animal and includes neurotoxic, non-neurotoxic envenomation, and envenomations of undetermined character, as well Cobra-spit ophthalmia. Examples of non-neurotoxic envenomation include hemotoxic, vasculotoxic, cardiotoxic, and myotoxic envenomation and are generically referred to in the descriptions below as "hemotoxic" or "cytotoxic" envenomation.

"Neurotoxic envenomation," refers to envenomation with a neurotoxic venom. Neurotoxic venoms include, for example and not limitation, venoms produced by venomous snakes.

"Venomous snake" refers to a snake having venom with any proportion of neurotoxic, hemotoxic, vasculotoxc, myotoxic, cytotoxic and/or other toxic properties. For example and without limitation venomous snakes include Cobra, Krait, Russell's Viper, Mambas, Coastal Taipan, New Guinea Death Adder, Boomslang (a Colubrid), Rattlesnakes, Coral snakes, Sea snakes (Hydrophiinae) among many other. All vipers including rattlesnakes, Russell's viper, saw-scaled viper, lance-head vipers, European vipers and habu snakes and mamushi among many others are venomous. All told, there are approximately 600 venomous snake species identified with more than 200 being considered of medical and veterinary significance worldwide. It will be appreciated that venoms comprise complex mixtures of proteins and other substances with toxic properties. Thus venom of a neurotoxic venomous snake may comprise agents with hemotoxic, vasculotoxic, cardiotoxic, myotoxic and/or other toxic properties, including neurotoxins.

The terms "treat", "treating", and "treatment", are used synonymously to refer to any action providing a benefit to a patient at risk for or suffering from an envenomation, including improvement in the condition through lessening, inhibition, suppression or elimination of at least one symptom, delay in progression of or damage from the envenomation or related disease, prevention, delay in or inhibition of the likelihood of the onset of envenomation symptoms, etc. Treatment, as used herein, may encompass both prophylactic and therapeutic treatment in context, principally of envenomation, but also of other envenomation-related disorders described herein or otherwise known to those of ordinary skill in the art.

"Storage-stable" means that a formulation is stable for a period of between about at least three to about six months or more at a temperature of between about 20° C. to 35° C. to about 40° C.

The term "pharmaceutically acceptable" as used herein means that the compound or composition is suitable for administration to a subject, including a human patient, to achieve the treatments described herein, without unduly deleterious side effects in light of the severity of the disease and necessity of the treatment.

The term "small molecule" as used herein, refers to a molecule with a molecular weight of less than about 2500, or less than about 1000, or less than about 750, or less than about 500.

II. Overview

In certain embodiments, the invention provides a method for treating or reducing the likelihood of neurotoxin-induced respiratory failure in a human subject (or other mammal) by determining that the subject is a victim of a snakebite or other envenomation and administering a $PLA_2$ inhibitor(s). In some embodiments the $PLA_2$ inhibitor is a 1H-Indole-3-glyoxylamide. In some embodiments the $PLA_2$ inhibitor(s) is varespladib and/or methylvarespladib.

The inventor has discovered that varespladib, methylvarespladib, other 1H-Indole-3-glyoxylamide PLA2 inhibitors, are effective in preventing death and other adverse effects of envenomentation by a large number of venomous animals, including snakes, including both vipers and elapids.

In certain embodiments, the invention provides a method for treating or reducing the likelihood of neurotoxin-induced respiratory failure in a human subject by determining that the subject is a victim of a snakebite or other envenomation and administering (or co-administering) a pharmaceutically effective dose of one or more compositions selected from the group consisting of a $PLA_2$ inhibitor, metalloproteinase inhibitor, and a serine protease inhibitor and, optionally, an adjuvant co-therapy as described herein (e.g. co-administration of an antibiotic, spreading factor inhibitor, acetylcholinesterase inhibitor with or without a mAChR antagonist).

In one aspect, the invention provides a method for treating or reducing the likelihood of tissue damage, bleeding and clotting disorders, cardiovascular collapse or neurotoxin-induced respiratory failure in a human or animal, comprising determining or clinically suspecting that the subject is a victim of a snakebite and administering pharmaceutically effective doses of inhibitors to the subject, wherein the inhibitor is or is not administered by injection or a combination of injection and non-injection methods.

Preferred compositions according to the present invention comprise at least one $PLA_2$ inhibitor, preferably varespladib and/or methylvarespladib, alone or in combination with one or more agents/compositions presented above.

In some embodiments, the PLA2 inhibitor is varespladib, methylvarespladib, or a combination.

In some embodiments the inhibitor is used to treat envenomentation by (i) an elapid; ii) a viperid; or (iii) a colubrid.

In some embodiments the inhibitor is used to treat envenomation by Cobra (*Naja*), such as *Naja naja, Naja nivea, Naja naja atra, Naja naja kaouthia, Naja melanoleuca Ophiophagus hannah, Hemachatus haemachatus* and other medically important elapids in Asia, Africa, Australia In some embodiments the inhibitor is used to treat envenomation by Krait (*Bungarus*), such as *Bungarus fasciatus, Bungarus caeruleus* and other elapids in Asia, Southeast Asia, Pacific Islands, Africa, Australia and occasionally, the Americas and Europe.

In some embodiments the inhibitor is used to treat envenomation by Coastal taipan (*Oxyuranus*), such as *Oxyuranus scutellatus*, by *Acanthophis* (death adder) such as *Acanthophis antarcticus* as well as *Pseudechis* (King Brown and Mulga snakes), Tiger snakes (*Notechis*) and other elapids of Australia, Papua New Guinea surrounding regions.

In some embodiments the inhibitor is used to treat envenomation by Eastern Coral snake (*Micrurus*), such as *M. fulvius* and other coral snakes of the Americas and Southeast Asia.

In some embodiments the inhibitor is used to treat envenomation by sea snakes (e.g. *Laticauda semifasciata*) and other sea snakes in the larger group of Hydrophiinae.

In some embodiments the inhibitor is used to treat envenomation by *Dendroaspis* (Black Mamba) such as *Dendroaspis polylepis*.

In some embodiments the inhibitor is used to treat evenomentation by a viperid such as vipers, rattlesnakes, copperheads/cottonmouths, and bushmasters including but not limited to *Crotalus* spp such as *C. adamanteus, C. atrox, C. scutulatus scutulatus* and others such as *Vipera berus, Bothrops asper, Bothrops jararaca, Bitis gabonica, Gloydius brevicaudis* and *Trimeresurus elegans* and other vipers from around the world.

In some embodiments the inhibitor is used to treat envenomation by Russell's viper (*Daboia* spp), *Daboia russelli* (also known as *D. russeli, Vipera russelli*), preventing immediate life-threat, kidney damage and pituitary infarct.

In some embodiments the inhibitor is used to treat envenomation by Saw-scaled Viper (*Echis*), such as *Echis carinatus* and other medically important *Echis* species.

In some embodiments the inhibitor is used to treat envenomation by *Crotalus* (pit viper, rattlesnake) such as *Crotalus scutulatus scutulatus, Crotalus atrox, Crotalus adamanteus, Crotalus basiliscus* and other rattlesnakes.

In some embodiments the inhibitor is used to treat envenomation by *Agkistrodon* (moccasin) such as *Agkistrodon piscivorus, Agkistrodon contortrix, Agkistrodon callose-lasma rhodostoma, Agkistrodon blomhoffii brevicaudus*.

In some embodiments the inhibitor is used to treat envenomation by African vipers such as *Bitis gabonica* and *Bitis caudalis*.

In some embodiments the inhibitor is used to treat evenomentation by a colubrid such as boomslangs, tree snakes, vine snakes, and mangrove snakes.

In some approaches, the PLA2 inhibitor may be used as a single agent. In preferred aspects the invention utilizes an effective amount of PLA2 inhibitor (preferably, the 1H-Indole-3-glyoxylamides, especially varespladib, methylvarespladib or indoxam, methylindoxam or a pharmaceutically acceptable salt or mixtures thereof) as the sole agent or agents to treat the subject suffering from an envenomation.

In some approaches varespladib and/or methylvarespladib is administered to an evenomated subject without administration of an antivenom, other small molecule MP inhibitor, or other small molecule SP inhibitor. In some approaches varespladib and/or methylvarespladib is administered to an evenomated subject and no administration of antivenom, other small molecule MP inhibitor or other small molecule SP inhibitor occurs for a period after administration of the PLA2 inhibitor. That period of time may be at least about 1 hour, at least about 2 hours, at least about 3 hours at least about 4 hours at least about 5 hours at least about 10 hours at least about 12 hours or at least about 24 hours. In other embodiments the varespladib and/or methylvarespladib may be co-administered or coformulated with a specific or polyvalent antivenom mixture.

It is noted that in certain preferred embodiments according to the present invention, the use of varespladib and/or methyl varespladib may be used in the absence of a separate serine- or metallo-protease inhibitor.

In some embodiments, the PLA2 inhibitor is not specific for venom PLA2 but has inhibitory activity against both mammalian (e.g., human, mouse or rat) PLA2 and venom PLA2. Without intending to be bound by a specific mechanism, the efficacy of the PLA2 inhibitor (e.g., varespladib and methylvarespladib) may result from the dual inhibition of host (mammalian or human) PLA2 activity, reducing the host's production of C-reactive protein and reducing an inflammatory response, as well as venom PLA2 activity thereby reducing the propensity to develop pathological cascades associated with tissue damage, consumption coagulopathy and other toxic cascades induced the by the introduction of venom into the victims body or eyes.

In one approach the sPLA2 inhibitor has a lower IC50 for human PLA2 compared to the IC50 for snake venom PLA2. In some embodiments, the IC50 for venom PLA2 is equivalent to, 10-fold, 100-fold, 1000-fold or lower than known for human PLA2.

Further, as described in Example 11, we have found that varespladib and methylvarespladib, in addition to exhibiting PLA2 inhibitory activity against a broad spectrum of snake venoms, also inhibit MP and SP activity of venom from a number of snakes. Surprisingly, in some instances varespladib and methylvarespladib were more potent MP and SP inhibitors than some commonly tested for use against medically important snake venoms. See, e.g., FIGS. 2A, B and FIG. 3. Without intending to be bound by a specific mechanism, the efficacy of the PLA2 inhibitor as a monotherapy may be augmented by the combination of PLA2 inhibitory activity and SP and/or MP inhibitory activity.

In some approaches, the PLA2 inhibitor may be used as a combination therapy. In some embodiments, the $PLA_2$ inhibitor is administered in combination with one or more agents selected from the group consisting of antivenom (or antivenin), a small molecule metalloproteinase inhibitor(s), and a small molecule serine protease inhibitor(s).

In various embodiments combination therapy may comprise administration of 2 or more active agents that are coformulated (e.g., mixed together or combined in a single unit dosage form) or co-administered (both administered as part of a course of therapy to treat envenomation). The co-administered agents can be administered simultaneously (e.g., as two or more separate unit dose forms, as simultaneous oral and IV administration, and the like) or can be administered at about the same time (concurrently) or sequentially (e.g., within about a minute or two of each other, about 10 min of each other, within about 30 min of each other, or within about 60 min of each other, or within 90 to 120 minutes of each other, or within 180 minutes of each other). Agents also may be administered at different times as part of the same course of therapy. For example, a patient may be administered one agent daily and a second agent weekly, as part of the same course of therapy. Similarly, a patient may receive an initial treatment (e.g., of varespladib and/or methylvarespladib) to initiate acute treatment of suspected or confirmed envenomation and a second treatment (e.g., antivenom) subsequently (e.g., within 12 hours, within 24 hours, or within 36 hours, for example) as part of the same course of therapy.

The term "co-administration" is used to describe the administration of two or more active compounds in effective amounts. Although the term co-administration preferably includes the administration of two or more active compounds to the patient at about the same time (simultaneous, concurrently or even sequentially), it is not necessary that the compounds actually be administered at exactly the same time (simultaneous) or even close in time (concurrent/sequential), only that amounts of compound will be administered to a patient or subject such that effective concentrations are found in the blood, serum or plasma, or in the pulmonary tissue at the same time to produce an intended result.

The term "co-formulation" refers to more than one active compound being formulated into a single dosage form for administration to the patient in that single dosage form. As noted, the term co-administration subsumes the term co-formulation at least for purposes of the timing of the administration of the active compounds at issue.

In one approach, the subject in need of treatment receives cotherapy comprising one or more PLA2 inhibitors (e.g., varespladib or methylvarespladib) and an antivenom.

In some approaches, the PLA2 inhibitor may be used as a combination therapy. In one approach, the subject in need of treatment receives cotherapy comprising one or more PLA2 inhibitors (e.g., varespladib or methylvarespladib) and an MP inhibitor. In some approaches the MP inhibitor is Prinomastat. In some approaches the MP inhibitor is selected from Vorinostat, Cefixime and other cephalosporins, Tazidime, Abbott-50192, Doxycycline and other tetracyclines, Nafamostat, Gingolide A, Levodopa, GM6001, Gabexate, Actarit, Granisetron, Marimastat, Batimastat, and Scopalomine.

In some approaches, the PLA2 inhibitor may be used as a combination therapy. In one approach, the subject in need of treatment receives cotherapy comprising one or more SPL2 inhibitors (e.g., varespladib or methylvarespladib) and an SP inhibitor. In some approaches the SP inhibitor is Nafamostat or Gabexate or AEBSF (4-(2-aminoethyl) benzenesulfonyl fluoride hydrochloride).

In some approaches, the PLA2 inhibitor may be used as a combination therapy. In one approach, the subject in need of treatment receives cotherapy comprising one or more SPL2 inhibitors (e.g., varespladib or methylvarespladib) and a MP inhibitor and an SP inhibitor. In some approaches the SP inhibitor is selected from Nafamostat, Gabexate and AEBSF and the MP inhibitor is selected from Prinomastat, Vorinostat, Cefixime and other cephalosporins, Tazidime, Abbott-50192, Doxycycline and other tetracyclines, Nafamostat, Gingolide A, Levodopa, GM6001, Gabexate, Actarit, Granisetron, Marimastat, Batimastat, and Scopalomine. In some approaches the MP inhibitor is Prinomastat or Vorinostat and the SP inhibitor is Nafamostat, Gabexate or AEBSF.

In some approaches the patient's eye or eyes are exposed to venom (e.g. cobra spit ophthalmia) and a varespladib-based mono- or combination therapy is applied topically.

III. Subject

In some embodiments, the subject at risk for or suffering from an envenomation is at risk of hemotoxin-, cytotoxin-, cardiotoxin- or myotoxin-induced tissue damage, limb or ocular injury with or without resulting kidney failure, multiple organ failure and/or cardiovascular collapse due to envenomation by a snake, fish, arthropod, mollusk, cnidarian or other venomous animal.

Subjects are mammals, including, for example, humans, non-human primates, mice, rats, dogs, and cats.

In some embodiments, a subject known to have been envenomated is treated according to the invention (e.g., treated with a 1H-indole-3-glyoxylamide such as varespladib and/or methylvarespladib). In some embodiments it is known that the subject was envenomated by a viper. In some embodiments it is known that the subject was envenomated by an elapid. In some embodiments it is known that the subject was envenomated by a colubrid. In some embodiments it is not known whether the subject was envenomated by a viper or an elapid or a colubrid (i.e., the snake type is not known at the time of treatment). In some embodiments the subject has been envenomated by a snake of unknown type.

In some embodiments, the subject has been envenomated with a dose of venom that is higher than the average LD50 for the venom in a human or non-human vertebrate. In some embodiments, the subject has been envenomated with a dose of venom that is lower than the average LD50 for the venom in a human or non-human vertebrate. In some embodiments, the subject has been envenomated with a dose of venom that is at least 0.5 times the average LD50 for the venom in a human or non-human vertebrate. In some embodiments the subject has been envenomated with a dose of venom that is at least 2-times the average LD50 for the venom in a human or non-human vertebrate.

IV. Phospholipase A2 Inhibitors

Lipases are enzymes that release biologically active molecules from membrane lipids. A key lipase enzyme family consists of phopholipase A2 (PLA2). Phospholipase A2 catalyzes the hydrolysis of phospholipids at the sn-2 position yielding a free fatty acid and a lysophospholipid. $PLA_2$ contributes towards release and/or formation of at least three important lipid mediators from membrane-arachidonic acid, platelet activating factor and lysophosphatidic acid. The release of arachidonic acid from membrane phospholipids by PLA is believed to be a key step in the control of eicosanoid production within the cell. $PLA_2$ enzymes are usually grouped into cytosolic $PLA_2$ ($cPLA_2$), secretory $PLA_2$ ($sPLA2$) and calcium independent $PLA_2$ ($iPLA_2$). Venom (e.g., snake venom) PLA2 are secreted (i.e., sPLA2s). Classification is based on molecular weight, calcium requirement, structural features, substrate specificity and functional role. See Ray, et al., "Phospholipase $A_2$ in Airway Disease: Target for Drug Discovery," *Journal of Drug Discovery and Therapeutics* 1 (8) 2013, 28-40.

Inhibitors of PLA2 have been identified in plants, snake venom, and other sources. PLA2 inhibitors have been investiated as potential therapeutic agents for treatment of inflammatory diseases. See, Magrioti, Victoria, and George Kokotos. "Phospholipase A2 inhibitors as potential therapeutic agents for the treatment of inflammatory diseases." *Expert opinion on therapeutic patents* 20.1 (2010): 1-18), and Dennis, Edward A., et al. "Phospholipase A2 enzymes: physical structure, biological function, disease implication, chemical inhibition, and therapeutic intervention." *Chemical reviews* 111.10 (2011): 6130-6185. Marcussi et al. suggested that the biotechnological potential of PLA2 inhibitors may provide therapeutic molecular models with antiophidian activity to supplement the conventional serum therapy against PLA2s. See Marcussi, Silvana, et al. "Snake venom phospholipase A2 inhibitors: medicinal chemistry and therapeutic potential." *Current Topics in Medicinal Chemistry* 7.8 (2007): 743-756). Also see Abhijit Dey and Jitendra Nath De, 2012. Phytopharmacology of Antiophidian Botanicals: A Review," *International Journal of Pharmacology,* 8: 62-79, and L S Guimaraes, Cesar, et al. "Biodiversity as a Source of Bioactive Compounds Against Snakebites." *Current medicinal chemistry* 21.25 (2014): 2952-2979. However, no small molecule PLA2 inhibitors have been approved as agents for treatment of evenomations.

sPLA2 inhibitors which can be used in the invention include, but are not limited to, LY315920 and S5920 (varespladib), LY333013 and S-3013 (methylvarespladib), LY 311727, BMS 181162, YM 26567, and Variabilin, SB 203347, S-2474 (methyl indoxam) and Indoxam. In some embodiments the $PLA_2$ inhibitor(s) is varespladib and/or methylvarespladib. Varespladib is an sPLA2 inhibitor that has been formulated for intravenous and oral administration and investigated for treatment of hyperlypidemia, sepsis-induced systematic inflammatory response syndrome, and accute chect syndrome (a complication of sickle cell disease). See, "Varespladib" *American Journal of Cardiovascular Drugs.* 11(2): 137-43. 2011. Methylvarespladib is a varespladib prodrug generally preferred for oral administration.

In preferred embodiments the PLA2 inhibitor is a small molecule (e.g., MW<2000, <1000, or <500).

As described herein, we have deminstrated that, unexpectedly, varespladib and methylvarespladib have remarkable properties that make them suitable as a "universal" first-line and oftentimes, complete, treatment for evenomation. As noted above, varespladib and methylvarespladib, in addition to exhibiting PLA2 inhibitory activity against a broad spectrum of snake venoms blunts the host's pathological response to snake venom, reducing harm via direct and indirect inhibition of snake venom's toxicity. This broad-spectrum activity against snake venom is particularly surprising in view of our observation that varespladib and methylvarespladib are not potent inhibitors of bee venom PLA2 and typically potency of medicinal PLA2 inhibitors is less for snake venoms than for mammals.

Surprisingly, varespladib and methylvarespladib also inhibit MP and SP activity of venom from a number of snakes. Indeed, surprisingly, in some experiments varespladib and methyl-varespladib were more potent SP and MP inhibitors in Russell's viper venom than for several medically important examples of these inhibitors (e.g. nafamostat, marimastat and batimastat).

Also surprising was the observation that the IC50s of varespladib and methyl-varespladib for essentially all snake venoms tested was significantly lower than values reported for inhibition of human sPLA2.

Also surprising was the discovery that even when venom effects were predominantly cytotoxic (including all manifestations in solid and liquid organs), varespladib and methylvarespladib monotherapy resulted in superior survival of mice injected with venom. This indicates that varespladib and methylvarespladib are effective in treating envenomation by snakes including, but not limited to, C. atrox, C. scutulatus, V. russelli (Daboia), V. berus and M. fulvius with hemorrhagic variants. Without intending to be bound by a particular mechanism, the fact that varespladib and methylvarespladib can suppress host response safely and are more potent against snake venom PLA2 (lower IC50) then against human sPLA may account in part for protection against the harmful effects of hemolysis and other tissue destruction. The direct and indirect venom and host MP and SP inhibitory activity of varespladib and methylvarespladib may also account in part for effects of protection against the harmful effects of hemolytic venoms.

Other PLA2 inhibitors, such as but not limited to other 1H-indole-3-glyoxylamides, are also useful in treatment of envonmation. One of ordinary skill in the art guided by the present disclosure will be able to identify PLA2 inhibitors and therapeutic combinations effective against a broad spectrum of venoms and/or tailored to a particular subset of venoms (e.g., particular species of snake, or venoms from particular types of invertebrates, for example).

Additional preferred sPLA2 inhibitors include those described in U.S. Pat. No. 5,654,326—represented by compounds according to the chemical structure:

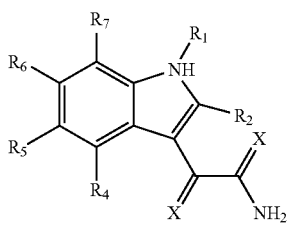

where X is O or S, preferably O;

$R_1$ is $C_7$-$C_{20}$ alkyl, $C_7$-$C_{20}$ alkenyl, $C_7$-$C_{20}$ alkynyl, a carbocyclic radical (preferably a benzyl or ethylphenyl group) or a heterocyclic radical;

$R_2$ is hydrogen, halo (F, Cl, Br, I), $C_1$-$C_3$ alkyl (preferably ethyl) or $C_3$-$C_4$ cycloalkyl;

$R_4$ is H or an —O—$(CH_2)_m$—C(O)ORv group, where m is 1-3 (preferably 1) and Rv is H or a $C_1$-$C_3$ alkyl group, preferably $CH_3$; and $R_5$, $R_6$ and $R_7$ are H, or a pharmaceutically acceptable salt, solvate or polymorph thereof.

Preferred sPLA2 inhibitor compounds (varespladib and methylvarespladib) for use in the present invention are represented by the chemical structure:

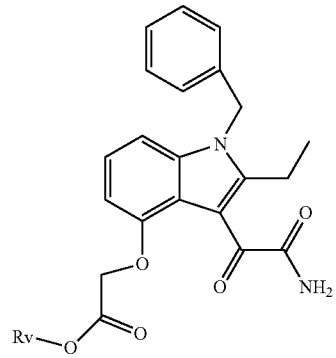

where Rv is H (varespladib) or methyl (methylvarespladib), or their pharmaceutically acceptable salts. The above compounds also may be used as prodrug forms $C_1$-$C_6$ alkyl esters, $C_2$-$C_7$ acyloxyalkyl esters, or $C_3$-$C_9$ alkyloxycarbonyloxyalkyl esters (each formed at $R_4$). These and other related compounds for use in the present invention are described in U.S. Pat. No. 5,654,326 to Bach, et al., which is incorporated by reference in its entirety herein.

Additional PLA2 inhibitors include for example: Varespladib Mofetil, N-Acetyl Cysteine, LY329722 (sodium [3-aminooxyalyl-1-benzyl-2-ethyl-6-methyl-1H-indol-4-yloxy]-acetic acid), ochnaflavone (a naturally occurring biflavonoid), and BPPA (5-(4-benzyloxyphenyl)-4S-(7-phenylhepatonoylamino) pentanoic acid. In certain embodiments, PLA2 inhibitors for use in the current invention are selected from the group consisting of: {9-[(phenyl)methyl]-5-carbamoylcarbazol-4-yl}oxyacetic acid; θ-benzyl-δJ-dimethoxy-S-tetrahydrocarbazole-carboxylic acid hydrazide; 9-benzyl-5,7-dimethoxy-1,2,3,4-tetrahydrocarbazole-4-carboxamide; [9-benzyl-4-carbamoyl-7-methoxy-1,2,3,4-tetrahydrocarbazol-5-yl]oxyacetic acid; [9-benzyl-4-carbamoyl-7-methoxycarbazol-5-yl]oxyacetic acid; methyl [9-benzyl-4-carbamoyl-7-methoxycarbazol-5-yl]oxyacetic acid; 9-benzyl-7-methoxy-5-cyanomethyloxy-S-tetrahydrocarbazole-carboxamide; 9-benzyl-7-methoxy-5-(1H-tetrazol-5-yl-methyl)oxy)-1,2,3,4-tetrahydrocarbazole-4-carboxamide; {9-[(phenyl)methyl]-5-carbamoyl-2-methyl-carbazol-4-yl}oxyacetic acid; {9-[(3-fluorophenyl)methyl]-5-carbamoyl-2-methylcarbazol-4-yl}oxyacetic acid; {9-[(3-methylphenyl)methyl]-5-carbamoyl-2-methylcarbazol-4-yl}oxyacetic acid; {9-[(phenyl)methyl]-5-carbamoyl-2-(4-trifluoromethylphenyl)-carbazol-4-yl}oxyacetic acid; 9-benzyl-5-(2-methanesulfonamido)ethyloxy-7-methoxy-1,2,3,4-tetrahydrocarbazole-4-carboxamide; 9-benzyl-4-(2-methanesulfonamido)ethyloxy-2-methoxycarbazole-5-carboxamide; 9-benzyl-4-(2-trifluoromethanesulfonamido) ethyloxy-2-methoxycarbazole-5-carboxamide; 9-benzyl-5-methanesulfonamidoylmethyloxy-7-methoxy-1, 2,3,4-tetrahydrocarbazole-4-carboxamide; 9-benzyl-4-methanesulfonamidoylmethyloxy-carbazole-5-carboxamide; [5-carbamoyl-2-pentyl-9-(phenylmethyl) carbazol-4-yl]oxyacetic acid; [5-carbamoyl-2-(1-methylethyl)-9-(phenylmethyl)carbazol-4-yl]oxyacetic acid; [5-carbamoyl-9-(phenylmethyl)-2-[(tri(-1-methylethylJsilyOoxymethyllcarbazol^-yl]oxyacetic acid; [5-carbamoyl-2-phenyl-9-(phenylmethyl)carbazol-4-yl]oxyacetic acid; [5-carbamoyl-2-(4-chlorophenyl)-9-(phenylmethyl) carbazol-4-yl]oxyacetic acid; [5-carbamoyl-2-(2-furyl)-9-(phenylmethyl)carbazol-4-yl]oxyacetic acid; [5-carbamoyl-9-(phenylmethyl)-2-[(tri(-1- methylethylJsilyOoxymethyllcarbazol^-ylloxyacetic acid; {9-[(2-Fluorophenyl)methyl]-5-carbamoylcarbazol-4-yl}oxyacetic acid; {9-[(2-trifluoromethylphenyl)methyl]-5-carbamoylcarbazol-4-yl}oxyacetic acid; {9-[(2-benzylphenyl)methyl]-5-carbamoylcarbazol-4-yl}oxyacetic acid; {9-[(1-naphthyljmethyll-δ-carbamoylcarbazol^-yl}oxyacetic acid; {9-[(2-cyanophenyl)methyl]-5-carbamoylcarbazol-4-yl}oxyacetic acid; {9-[(3-cyanophenyl)methyl]-5-carbamoylcarbazol-4-yl}oxyacetic acid; {9-[(3,5-dimethylphenyl)nnethyl]-5-carbannoylcarbazol-4-yl}oxyacetic acid; {9-[(3-iodophenyl)methyl]-5-carbannoylcarbazol-4-yl}oxyacetic acid; {9-[(2-Chlorophenyl)methyl]-5-carbannoylcarbazol-4-yl}oxyacetic acid; {9-[(2,3-difluorophenyl)methyl]-5-carbannoylcarbazol-4-yl}oxyacetic acid; {9-[(2,6-difluorophenyl)methyl]-5-carbannoylcarbazol-4-yl}oxyacetic acid; {9-[(2,6-dichlorophenyl)methyl]-5-carbannoylcarbazol-4-yl}oxyacetic acid; {9-[(2-biphenyl)methyl]-5-carbamoylcarbazol-4-yl}oxyacetic acid; {9-[(2-Biphenyl)methyl]-5-carbamoylcarbazol-4-yl}oxyacetic acid methyl ester; [9-Benzyl-4-carbamoyl-1,2,3,4-tetrahydrocarbazol-5-yl]oxyacetic acid; {9-[(2-Pyridyl)methyl]-5-carbamoylcarbazol-4-yl}oxyacetic acid; {9-[(3-Pyridyl)nnethyl]-5-carbannoylcarbazol-4-yl}oxyacetic acid; [9-benzyl-4-carbamoyl-8-nnethyl-1,2,3,4-tetrahydrocarbazol-5-yl]oxyacetic acid; [9-benzyl-5-carbamoyl-1-methylcarbazol-4-yl]oxyacetic acid; [9-benzyl-4-carbamoyl-8-fluoro-1,2,3,4-tetrahydrocarbazol-5-yl]oxyacetic acid; [9-benzyl-4-carbamoyl-8-chloro-1,2,3,4-tetrahydrocarbazol-5-yl] oxyacetic acid; [5-carbamoyl-9-(phenylnnethyl)-2-[[(propen-3-yl)oxy]methyl]carbazol-4-yl]oxyacetic acid; [5-carbamoyl-9-(phenylmethyl)-2-[(propyloxyjmethyllcarbazolylloxyacetic acid; 9-benzyl-7-methoxy-5-((carboxamidonnethyloxy-tetrahydrocarbazole-carboxannide; 9-benzyl-7-methoxy-S-cyanonnethyloxy-carbazole-carboxannide; 9-benzyl-7-methoxy-5-((1H-tetrazol-5-yl-methyl)oxy)-carbazole-4-carboxannide; 9-benzyl-7-methoxy-5-((carboxamidomethyl)oxy)-carbazole-4-carboxamide; [9-Benzyl-4-carbamoyl-1,2,3,4-tetrahydrocarbazole-5-yl)]oxyacetic acid; {9-[(phenyl)methyl]-5-carbannoyl-2-nnethyl-carbazol-4-yl}oxyacetic acid; {9-[(3-fluorophenyl)methyl]-5-carbannoyl-2-nnethylcarbazol-4-yl}oxyacetic acid; {9-[(3-methylphenyl)nnethyl]-5-carbannoyl-2-nnethylcarbazol-4-yl}oxyacetic acid; {9-[(phenyl)methyl]-5-carbamoyl-2-(4-trifluoromethylphenyl)-carbazol-4-yl}oxyacetic acid; 9-benzyl-5-(2-methanesulfonamido)ethyloxy-7-methoxy-1,2,3,4-tetrahydrocarbazole-4-carboxamide; 9-benzyl-4-(2-methanesulfonamido)ethyloxy-2-methoxycarbazole-5-carboxamide; 9-benzyl-4-(2-trifluoromethanesulfonamido)ethyloxy-2-methoxycarbazole-5-carboxamide; 9-benzyl-5-methanesulfonamidoylmethyloxy-7-methoxy-1,2,3,4-tetrahydrocarbazole-4-carboxamide; 9-benzyl-4-methanesulfonamidoylmethyloxy-carbazole-5-carboxamide; [5-carbamoyl-2-pentyl-9-(phenylmethyl)carbazol-4-yl]oxyacetic acid; [5-carbamoyl-2-(1-methylethyl)-9-(phenylmethyl)carbazol-4-yl]oxyacetic acid; [5-carbamoyl-9-(phenylmethyl)-2-[(tri(-1-methylethylJsilyOoxymethyllcarbazolyloxyacetic acid; [5-carbamoyl-2-phenyl-9-(phenylmethyl)carbazol-4-yl]oxyacetic acid; [5-carbamoyl-2-(4-chlorophenyl)-9-(phenylmethyl)carbazol-4-yl]oxyacetic acid; [5-carbamoyl-2-(2-furyl)-9-(phenylmethyl)carbazol-4-yl]oxyacetic acid; [5-carbamoyl-9-(phenylmethyl)-2-[(tri(-1-methylethylJsilyOoxymethyllcarbazol-ylloxyacetic acid; {9-[(3-fluorophenyl)methyl]-5-carbamoylcarbazol-4-yl}oxyacetic acid; {9-[(3-chlorophenyl)methyl]-5-carbamoylcarbazol-4-yl}oxyacetic acid; {9-[(3-phenoxyphenyl)methyl]-5-carbamoylcarbazol-4-yl}oxyacetic acid; {9-[(2-Fluorophenyl)methyl]-5-carbamoylcarbazol-4-yl}oxyacetic acid; {9-[(2-trifluoromethylphenyl)methyl]-5-carbamoylcarbazol-4-yl}oxyacetic acid; {9-[(2-benzylphenyl)methyl]-5-carbamoylcarbazol-4-yl}oxyacetic acid; {9-[(3-trifluoromethylphenyl)methyl]-5-carbamoylcarbazol-4-yl}oxyacetic acid; {9-[(1-naphthyljmethyll-δ-carbamoylcarbazol-yl}oxyacetic acid; {9-[(2-cyanophenyl)methyl]-5-carbamoylcarbazol-4-yl}oxyacetic acid; {9-[(3-cyanophenyl)methyl]-5-carbamoylcarbazol-4-yl}oxyacetic acid; {9-[(2-methylphenyl)nnethyl]-5-carbannoylcarbazol-4-yl}oxyacetic acid; {9-[(3-methylphenyl)nnethyl]-5-carbannoylcarbazol-4-yl}oxyacetic acid; {9-[(3,5-dimethylphenyl)nnethyl]-5-carbannoylcarbazol-4-yl}oxyacetic acid; {9-[(3-iodophenyl)methyl]-5-carbannoylcarbazol-4-yl}oxyacetic acid; {9-[(2-Chlorophenyl)methyl]-5-carbannoylcarbazol-4-yl}oxyacetic acid; {9-[(2,3-difluorophenyl)methyl]-5-carbannoylcarbazol-4-yl}oxyacetic acid; {9-[(2,6-difluorophenyl)methyl]-5-carbannoylcarbazol-4-yl}oxyacetic acid; {9-[(2,6-dichlorophenyl)methyl]-5-carbannoylcarbazol-4-yl}oxyacetic acid; {9-[(3-trifluoromethoxyphenyl)nnethyl]-5-carbannoylcarbazol-4-yl}oxyacetic acid; {9-[(2-biphenyl)methyl]-5-carbamoylcarbazol-4-yl}oxyacetic acid; {9-[(2-Biphenyl)methyl]-5-carbamoylcarbazol-4-yl}oxyacetic acid methyl ester; [9-Benzyl-4-carbamoyl-1,2,3,4-tetrahydrocarbazole-5-yl]oxyacetic acid; {9-[(2-Pyridyl)methyl]-5-carbamoylcarbazol-4-yl}oxyacetic acid; {9-[(3-Pyridyl)nnethyl]-5-carbannoylcarbazol-4-yl}oxyacetic acid; [9-benzyl-4-carbamoyl-8-nnethyl-1,2,3,4-tetrahydrocarbazol-5-yl] oxyacetic acid; [9-benzyl-5-carbamoyl-1-methylcarbazol-4-yl]oxyacetic acid; [θ-benzyl^-carbamoyl-δ-fluoro-1,2,3,4-tetrahydrocarbazol-5-yl]oxyacetic acid; [θ-benzyl-δ-carbannoyl-1-fluorocarbazol-4-yl]oxyacetic acid; [9-benzyl-4-carbamoyl-8-chloro-1,2,3,4-tetrahydrocarbazol-5-yl] oxyacetic acid; [9-benzyl-5-carbamoyl-1-chlorocarbazol-4-yl]oxyacetic acid; [9-[(Cyclohexyl)methyl]-5-carbannoylcarbazol-4-yl]oxyacetic acid; [9-[(Cyclopentyl)methyl]-5-carbamoylcarbazol-4-yl]oxyacetic acid; [5-carbamoyl-9-(phenylmethyl)-2-(2-thienyl)carbazol-4-yl] oxyacetic acid; [5-carbamoyl-9-(phenylnnethyl)-2-[[(propen-3-yl)oxy]methyl]carbazol-4-yl]oxyacetic acid; [5-carbamoyl-9-(phenylnnethyl)-2-[(propyloxyjmethyllcarbazol-ylloxyacetic acid; 9-benzyl-7-methoxy-5-((carboxamidomethyloxy-tetrahydrocarbazole-carboxamide; 9-benzyl-7-methoxy-6-cyanomethyloxy-carbazole-carboxamide; 9-benzyl-7-methoxy-5-((1H-tetrazol-5-yl-methyl)oxy)-carbazole-4-carboxamide; 9-benzyl-7-methoxy-5-((carboxamidomethyl)oxy)-carbazole-4-carboxamide; [9-Benzyl-4-carbamoyl-1,2,3,4-tetrahydrocarbazole-5-yl]oxyacetic acid; (R,S)-(9-benzyl-4-carbamoyl-1-oxo-3-thia-1,2,3,4-tetrahydrocarbazol-5-yl)oxyacetic acid; (R,S)-(9-benzyl-4-carbamoyl-3-thia-1,2,3,4-tetrahydrocarbazol-5-yl)oxyacetic acid; 2-(4-oxo-5-carboxamido-9-benzyl-9/-/-pyrido[3,4-ib]indolyl)acetic acid chloride; [N-benzyl-1-carbamoyl-1-aza-1,2,3,4-tetrahydrocarbazol-8-yl]oxyacetic acid; 4-methoxy-6-methoxycarbonyl-10-phenylmethyl-6,7,8,9-tetrahydropyrido[1,2-a]indole; (4-carboxamido-9-phenylmethyl-4,5-dihydrothiopyrano[3,4-b]indol-5-yl)oxyacetic acid; 3,4-dihydro-4-carboxamidol-5-methoxy-9-phenylmethylpyrano[3,4-ib]indole; 2-[(2,9 bis-benzyl-4-carbamoyl-i,2,3,4-tetrahydro-betacarbolin-5-yl)oxy]acetic acid; 2-[4-oxo-5-carboxamido-9-(2-methylbenzyl)-9/-/-pyrido[3,4-ib]indolyl]acetic acid; 2-[4-oxo-5-carboxamido-9-(3-methylbenzyl)-9/-/-pyrido[3,4-ib]indolyl]acetic acid; 2-[4-oxo-5-carboxamido-9-(4-methylbenzyl)-9/-/-pyrido[3,4-ib]indolyl]acetic acid; 2-[4-oxo-5-carboxamido-9-(4-tertbutylbenzyl)-9/-/-pyrido[3,4-ib]indolyl]acetic acid; 2-[4-oxo-5-carboxamido-9-pentafluorobenzyl-9/-/-pyrido[3,4-ib]indolyl]acetic acid; 2-[4-oxo-5-carboxamido-9-(2-fluorobenzyl)-9/-/-pyrido[3,4-ib]indolyl]acetic acid; 2-[4-oxo-5-carboxamido-9-(3-fluorobenzyl)-9/-/-pyrido[3,4-ib]indolyl]acetic acid; 2-[4-oxo-5-carboxamido-9-(4-fluorobenzyl)-9/-/-pyrido[3,4-ib]indolyl]acetic acid; 2-[4-oxo-5-carboxamido-9-(2,6-difluorobenzyl)-9/-/-pyrido[3,4-ib]indolyl]acetic acid; 2-[4-oxo-5-carboxamido-9-(3,4-difluorobenzyl)-9/-/-pyrido[3,4-ib]indolyl]acetic acid; 2-[4-oxo-5-carboxamido-9-(2,5-difluorobenzyl)-9/-/-pyrido[3,4-jb]indolyl]acetic acid; 2-[4-oxo-5-carboxamido-9-(3,5-difluorobenzyl)-9/-/-pyπdo[3,4-ib]indolyl]acetic acid; 2-[4-oxo-5-carboxamido-9-(2,4-difluorobenzyl)-9/-/-pyrido[3,4-ib]indolyl]acetic acid; 2-[4-oxo-5-carboxamido-9-(2,3-difluorobenzyl)-9/-/-pyrido[3,4-ib]indolyl]acetic acid; 2-[4-oxo-5-carboxamido-9-[2-(trifluoromethyl)benzyl]-9/-/-pyrido[3,4-ib]indolyl]acetic acid; 2-[4-oxo-5-carboxamido-9-[2-(trifluoromethyl)benzyl]-9/-/-pyrido[3,4-ib]indolyl]acetic acid; 2-[4-oxo-5-carboxamido-9-[3-(trifluoromethyl)benzyl]-9/-/-pyrido[3,4-ib]indolyl]acetic acid; 2-[4-oxo-5-carboxamido-9-[4-(trifluoromethyl)benzyl]-9/-/-pyrido[3,4-ib]indolyl]acetic acid; 2-[4-oxo-5-carboxamido-9-[3,5-bis(trifluoromethyl)benzyl]-9/-/-pyrido[3,4-ib]indolyl]acetic acid; 2-[4-oxo-5-carboxamido-9-[2,4-bis(trifluoromethyl)benzyl]-9/-/-pyrido[3,4-ib]indolyl]acetic acid; 2-[4-oxo-5-carboxamido-9-(a-methylnaphthyl)-9/-/-pyrido[3,4-ib]indolyl]acetic acid; 2-[4-oxo-5-carboxamido-9-(b-methylnaphthyl)-9/-/-pyrido[3,4-ib]indolyl]acetic acid; 2-[4-oxo-5-carboxamido-9-(3,5-dimethylbenzyl)-9/-/-pyrido[3,4-ib]indolyl]acetic acid; 2-[4-oxo-5-carboxamido-9-(2,4-dimethylbenzyl)-9/-/-pyrido[3,4-ib]indolyl]acetic acid; 2-[4-oxo-5-carboxamido-9-(2-phenylbenzyl)-9/-/-pyrido[3,4-ib]indolyl]acetic acid; 2-[4-oxo-5-carboxamido-9-(3-phenylbenzyl)-9/-/-pyrido[3,4-ib]indolyl]acetic acid; 2-[4-oxo-5-carboxamido-9-(4-phenylbenzyl)-9/-/-pyrido[3,4-ib]indolyl]acetic acid; 2-[4-oxo-5-carboxamido-9-(1-fluorenylmethy)-9/-/-pyrido[3,4-ib]indolyl]acetic acid; 2-[4-oxo-5-carboxamido-9-(2-fluoro-3-methylbenzyl)-9/-/-pyrido[3,4-ib]indolyl]acetic acid; 2-[4-oxo-5-carboxamido-9-(3-benzoylbenzyl)-9/-/-pyrido[3,4-ib]indolyl]acetic acid; 2-[4-oxo-5-carboxamido-9-(2-phenoxybenzyl)-9/-/-pyrido[3,4-ib]indolyl]acetic acid; 2-[4-oxo-5-carboxamido-9-(3-phenoxybenzyl)-9/-/-pyrido[3,4-ib]indolyl]acetic acid; 2-[4-oxo-5-carboxamido-9-(4-phenoxybenzyl)-9/-/-pyrido[3,4-ib]indolyl]acetic acid; 2-[4-oxo-5-carboxannido-9-[3-[2-(fluorophenoxy)benzyl]]-9/-/-pyπdo[3,4-ib]indolyl]acetic acid; 2-[4-oxo-5-carboxamido-9-[3-[4-(fluorophenoxy)benzyl]]-9/-/-pyrido[3,4-ib]indolyl]acetic acid; 2-[4-oxo-5-carboxamido-9-[2-fluoro-3-(trifluoronnethyl)benzyl]-9/-/-pyπdo[3,4-f>]indolyl]acetic acid; 2-[4-oxo-5-carboxamido-9-[2-fluoro-4-(trifluoronnethyl)benzyl]-9/-/-pyrido[3,4-ib]indolyl]acetic acid; 2-[4-oxo-5-carboxamido-9-[2-fluoro-5-(trifluoromethyl)benzyl]-9H-pyrido[3,4-ib]indolyl]acetic acid; 2-[4-oxo-5-carboxamido-9-[3-fluoro-5-(trifluoromethyl)benzyl]-9/-/-pyrido[3,4-ib]indolyl]acetic acid; 2-[4-oxo-5-carboxamido-9-[4-fluoro-2-(trifluoronnethyl)benzyl]-9/-/-pyrido[3,4-ib]indolyl]acetic acid; 2-[4-oxo-5-carboxamido-9-[4-fluoro-3-(trifluoronnethyl)benzyl]-9/-/-pyrido[3,4-ib]indolyl]acetic acid; 2-[4-oxo-5-carboxamido-9-[2-fluoro-6-(trifluoronnethyl)benzyl]-9/-/-pyrido[3,4-ib]indolyl]acetic acid; 2-[4-oxo-5-carboxamido-9-(2,3,6-trifluorobenzyl)-9/-/-pyrido[3,4-ib]indolyl]acetic acid; 2-[4-oxo-5-carboxamido-9-(2,3,5-trifluorobenzyl)-9/-/-pyrido[3,4-ib]indolyl]acetic acid; 2-[4-oxo-5-carboxamido-9-(2,4,5-trifluorobenzyl)-9/-/-pyrido[3,4-ib]indolyl]acetic acid; 2-[4-oxo-5-carboxamido-9-(2,4,6-trifluorobenzyl)-9/-/-pyrido[3,4-ib]indolyl]acetic acid; 2-[4-oxo-5-carboxamido-9-(2,3,4-trifluorobenzyl)-9/-/-pyrido[3,4-ib]indolyl]acetic acid; 2-[4-oxo-5-carboxamido-9-(3,4,5-trifluorobenzyl)-9/-/-pyrido[3,4-ib]indolyl]acetic acid; 2-[4-oxo-5-carboxamido-9-[3-(trifluoronnethoxy)benzyl]-9/-/-pyrido[3,4-ib]indolyl]acetic acid; 2-[4-oxo-5-carboxamido-9-[4-(trifluoronnethoxyl)benzyl]-9/-/-pyrido[3,4-ib]indolyl]acetic acid; 2-[4-oxo-5-carboxamido-9-[4-methoxy(tetrafluoro)benzyl]-9/-/-pyrido[3,4-ib]indolyl]acetic acid; 2-[4-oxo-5-carboxamido-9-(2-nnethoxybenzyl)-9/-/-pyrido[3,4-ib]indolyl]acetic acid; 2-[4-oxo-5-carboxamido-9-(3-nnethoxybenzyl)-9/-/-pyrido[3,4-ib]indolyl]acetic acid; 2-[4-oxo-5-carboxamido-9-(4-nnethoxybenzyl)-9/-/-pyrido[3,4-ib]indolyl]acetic acid; 2-[4-oxo-5-carboxannido-9-(4-ethylbenzyl)-9/-/-pyπdo[3,4-ib]indolyl]acetic acid; 2-[4-oxo-5-carboxamido-9-(4-isopropylbenzyl)-9/-/-pyrido[3,4-ib]indolyl]acetic acid; 2-[4-oxo-5-carboxamido-9-(3,4,5-trinnethoxybenzyl)-9/-/-pyrido[3,4-ib]indolyl]acetic acid; 2-[4-oxo-5-carboxamido-9-(3,4-nnethylenedioxybenzyl)-9/-/-pyrido[3,4-ib]indolyl]acetic acid; 2-[4-oxo-5-carboxamido-9-(4-nnethoxy-3-nnethylbenzyl)-9/-/-pyπdo[3,4-ib]indolyl]acetic acid; 2-[4-oxo-5-carboxamido-9-(3,5-dinnethoxybenzyl)-9/-/-pyπdo[3,4-ib]indolyl]acetic acid; 2-[4-oxo-5-carboxamido-9-(2,5-dinnethoxybenzyl)-9/-/-pyπdo[3,4-ib]indolyl]acetic acid; 2-[4-oxo-5-carboxamido-9-(4-ethoxybenzyl)-9/-/-pyrido[3,4-ib]indolyl]acetic acid; 2-[4-oxo-5-carboxamido-9-(cyclohexylnnethyl)-9/-/-pyrido[3,4-ib]indolyl]acetic acid; 2-[4-oxo-5-carboxamido-9-(cyclopentylnnethyl)-9/-/-pyrido[3,4-ib]indolyl]acetic acid; 2-[4-oxo-5-carboxamido-9-ethyl-9/-/-pyrido[3,4-ib]indolyl]acetic acid; 2-[4-oxo-5-carboxamido-9-(1-propyl)-9/-/-pyrido[3,4-ib]indolyl]acetic acid; 2-[4-oxo-5-carboxamido-9-(2-propyl)-9/-/-pyrido[3,4-ib]indolyl]acetic acid; 2-[4-oxo-5-carboxamido-9-(1-butyl)-9H-pyrido[3,4-]indolyl]acetic acid; 2-[4-oxo-5-carboxamido-9-(2-butyl)-9/-/-pyrido[3,4-ib]indolyl]acetic acid; 2-[4-oxo-5-carboxamido-9-isobutyl-9/-/-pyrido[3,4-ib]indolyl]acetic acid; 2-[4-oxo-5-carboxamido-9-[2-(1-phenylethyl)]-9/-/-pyrido[3,4-ib]indolyl]acetic acid; 2-[4-oxo-5-carboxamido-9-[3-(1-phenylpropyl)]-9/-/-pyrido[3,4-ib]indolyl]acetic acid; 2-[4-oxo-5-carboxamido-9-[4-(1-phenylbutyl)]-9/-/-pyrido[3,4-ib]indolyl]acetic acid; 2-[4-oxo-5-carboxamido-9-(1-pentyl)-9/-/-pyrido[3,4-Lb]indolyl]acetic acid; 2-[4-oxo-5-carboxamido-9-(1-hexyl)-9/-/-pyrido[3,4-ib]indolyl]acetic acid; 4-[(9-benzyl-4-carbamoyl-1,2,3,4-tetrahydrocarbazol-6-yl)oxy]butyric acid; 3-[(9-benzyl-4-carbamoyl-1,2,3,4-tetrahydrocarbazol-θ-yOoxylpropylphosphonic acid; 2-[(9-benzyl-4-carbamoyl-1,2,3,4-tetrahydrocarbazol-6-yl)oxy]methylbenzoic acid; 3-[(9-benzyl-4-carbamoyl-7-n-octyl-1,2,3,4-tetrahydrocarbazol-6-yl)oxy]propylphosphonic acid; 4-[(9-benzyl-4-carbamoyl-7-ethyl-1,2,3,4-tetrahydrocarbazol-6-yl)oxy]butyric acid; 3-[(9-benzyl-4-carbamoyl-7-ethyl-1,2,3,4-tetrahydrocarbazol-6-yl)oxy]propylphosphonic acid; 3-[(9-benzyl-4-carbamoyl-7-ethyl-1,2,3,4-tetrahydrocarbazol-6-yl)oxy]propylphosphonic acid; (S)-(+)-4-[(9-benzyl-4-carbamoyl-7-ethyl-1,2,3,4-tetrahydrocarbazol-6-yl)oxy]butyric acid; 4-[9-benzyl-4-carbamoyl-6-(2-cyanoethyl)-1,2,3,4-tetrahydrocarbazol-6-yl]oxybutyric acid; 4-[9-benzyl-4-carboxamido-7-(2-phenylethyl)-1,2,3,4-tetrahydrocarbazol-6-yl]oxybutyric acid; 4-[9-benzyl-4-carboxamidocarbazol-6-yl]oxybutyric acid; methyl 2-[(9-benzyl-4-carbamoyl-1,2,3,4-tetrahydrocarbazol-6-yl)oxy]methylbenzoate; 4-[9-benzyl-4-carbamoyl-7-(2-cyanoethyl)-1,2,3,4-tetrahydrocarbazol-6-yl]oxybutyric acid; 9-benzyl-7-methoxy-5-cyanomethyloxy-tetrahydrocarbazole-carboxamide; [9-benzyl-4-carbamoyl-8-methyl-carbazole-5-yl]oxyacetic acid; and [θ-benzyMcarbamoyl-carbazole-6-yl]oxyacetic acid, or pharmaceutically acceptable salts, solvates, prodrug derivatives, racemates, tautomers, or optical isomers thereof.

Direct and indirect $PLA_2$ inhibitors also include N,N-dimethylcarbamoylmethyl,4-4-guanidinobenzoyloxy-phenylacetate (Camostat, camostate) or ethyl-p[6-guanidinohexanoyloxy]-benzoate methansulfonate (gabexate) and leukotriene synthesis inhibitor selected from the group consisting of methyl arachidonyl fluorophosphonate (MAFP), pyrroxyphene, ONO-RS-082, 1-[3-(4-octylphenoxy)-2-oxopropyl]indole-5-carboxylic acid, 1-[3-(4-octylphenoxy)-2-oxopropyl]indole-6-carboxylic acid, arachidonyl trifluoromethyl ketone, D609, 4-{3-[5-chloro-2-(2-{[(3,4-dichlorobenzyl)sulfonyl]amino}ethyl)-1-(diphenylmethyl)-1H-indol-3-yl]propyl}benzoic acid (WAY-196025), efipladib, 4-{2-[5-chloro-2-(2-{[(3,4-dichlorobenzyl)sulfonyl]amino}-ethyl)-1-(diphenylmethyl)-1H-indol-3-yl]ethoxy}benzoic acid, Ecopladib, (E)-N-[(2S,4R)-4-[N-(biphenyl-2-ylmethyl)-N-2-methylpropylamino]-1-[2-(2,-4-difluorobenzoyl)benzoyl]pyrrolidin-2-yl]methyl-3-[4-(2,4-dioxothiazolidin-5-ylidenemethyl) phenyl]acrylamide (RSC-3388), berberine, glutamine, Indoxam, Me-Indoxam or a pharmaceutically acceptable salt thereof.

Certain embodiments of the invention involve the administration of a $PLA_2$ inhibitor selected from the group consisting of varespladib (LY 315920), methylated varespladib (LY333013), AIPLAI (*Azadirachta indica* $PLA_2$ inhibitor), BMS-181162, LY311727, ARL-67974, FPL67047, SB-203347, Ro-23-9358, YM-26734, YM 26567, IS-741, MJ33, flunixin, Effipladib, Way 196025, Ecopladib, Giripladib, Variabilin, Indoxam, Me-Indoxam, SB 203347, PAF-AH, Darapladib, phosphatidylethanolamine (PE), phosphatidylserine (PS), phosphatidylcholine (PC), phosphatidylinositol (PI), and phosphatidylglycerol (PG) and mixtures thereof linked (conjugated) to at least one compound selected from the group consisting of carboxymethylcellulose (CMPE, CMC-Peor CME), hyaluronic acid (HYPE, HyPE, and Hyal-PE), heparin (HEPPE, HepPE, HePPE, Hepa-PE), chondroitine sulfate A (CSAPE, CsaPE, CsAPE), Polygeline (haemaccel) (HemPE, HEMPE), hydroxyethylstarch (HesPE, HESPE)(preferably Hyaluronic acid-linked phosphatidyl ethanolamine (HyPE)) and analogs, derivatives, pharmaceutically acceptable salts, enantiomers, diastereomers, solvates, polymorphs and mixtures thereof.

$PLA_2$ inhibitors also include compositions comprising at least one phopholipid selected from the group consisting of phosphatidylethanolamine (PE), phosphatidylserine (PS), phosphatidylcholine (PC), phosphatidylinositol (PI), and phosphatidylglycerol (PG) and mixtures thereof linked (conjugated) to at least one compound selected from the group consisting of carboxymethylcellulose (CMPE, CMC-Peor CME), hyaluronic acid (HYPE, HyPE, and Hyal-PE), heparin (HEPPE, HepPE, HePPE, Hepa-PE), chondroitine sulfate A (CSAPE, CsaPE, CsAPE), Polygeline (haemaccel) (HemPE, HEMPE), hydroxyethylstarch (HesPE, HESPE) and mixtures thereof. Hyaluronic acid-linked phosphatidyl ethanolamine (HyPE) is a preferred $PLA_2$ inhibitor.

In some embodiments the PLA2 inhibitor is an inhibitor described below in Example 14 ("HTS Discovery of Elapid PLA2 inhibitors Using *M. fulvius* Venom").

V. Antivenom

The anti-PLA2, MP and SP potency of many antivenoms against vertebrate and invertebrate toxins can be augmented, for example, by varespladib, methylvarespladib (typically used as PLA2 inhibitors) alone and in combination with prinomastat, batimastat, marimastat (with or without varespladib, methylvarespladib in combination with antivenom) and other inhibitors with specific and non-specific activity against components of venom and salutary modification of the host response or a combination of salutary effects.

The ability to deliver an antidote more quickly than antivenom can be prepared (sequential dosing) will address the long unmet need of performing randomized clinical trials of antivenom since small molecule antidotes can be delivered in advance of the final decision to give antivenom or not. In combination with antivenom, the discovery that the potency of the drug-antivenom combinations is improved will address the long-unmet need of reduced antivenom usage, fewer complications and lowered costs of production, storage and hospital time.

Antivenom co-therapy may be particularly appropriate in the case of envenomations that have both neurotoxic and hemotoxic components, causing both paralysis and bleeding or clotting disorders where the snakebite is a viper, elapid or colubrid with variation of need and formulation dictated by specific needs of a region and its snakebite risk and treatment resources. Co-therapies can also entail use of antivenom and inhibitors of other venom enzymes, such as inhibitors of phospholipases (e.g. phospholipase A2) or other venom components that can cause paralysis, destroy nerve terminals and/or cause bleeding disorders (e.g. melittin, which stimulates phospholipase and can be both hemotoxic/cyto and neurotoxic (Clapp et al, 1995, *Brain Res.* 693:101-11). Active ingredients can be conjugated to antivenom or fragments of antibodies directed against venom components, and mACHR antagonists such as atropine, glycopyrrolate can be optionally co-administered to mitigate undesired muscarinic effects of AChEIs.

Monovalent and polyvalent antivenoms can be used in the treatment of envenomations attributable to bites by snakes, spiders, acarids, insects, scorpions and marine animals. Representative antivenoms and antivenom production techniques are well-known to those of ordinary skill in the art. See U.S. Pat. No. 5,340,923. For example, CroFab® (BTG International, Plc.) is a Crotalidae Polyvalent Immune Fab (Ovine) antivenom "indicated for the management of patients with North American crotalid envenomation. The term crotalid is used to describe the Crotalinae subfamily (formerly known as Crotalidae) of venomous snakes that includes rattlesnakes, copperheads, and cottonmouths/water moccasins. Early use of CroFab® (within 6 hours of snakebite) is advised to prevent clinical deterioration and the occurrence of systemic coagulation abnormalities." Early use of varespladib-based therapeutics will decrease antivenom requirements, reducing complications and costs when antivenom is not needed and improving outcomes when both therapeutic strategies are employed. In some instances, varespladib-based therapies will completely replace the need for antivenom (e.g. many viper bites and coral snake bites). Importantly, varespladib-based therapies used in conjuction with specific, paraspecific or non-specific antivenoms will improve the therapeutic efficacy of all antivenom formulations whether coadministered or coformulated.

Importantly, pharmaceutical compositions comprising varespladib, varespladib methyl and optionally, preferred MP inhibitors such as prinomastat, batimastat and marimastat improve the performance of paraspecific antivenoms. As described in Example 11, below, the exemplary PLA2 inhibitor varespladib and the exemplary antivenom, Crofab®, were combined and assayed for PLA2 inhibitory activity, enhanced potency was unxpectedly observed. The synergy was strongest for *Acanthophis antarcticus* (Varespladib). Of the venoms tested, *A. antarcticus* is least related to the viper venom against which Crofab® is raised. This evidence strongly supports the use of sPLA2 inhibitors to broaden the spectrum of snake envenomatons that can be treated by a given antivenom. Co-therapy with a sPLA2 inhibitor can increase the paraspecific effects and potency of an antivenom raised against a snake venom different from that of the evenomating snake (e.g., a subspecies or related species of the snake against which the antivenom is directed). Co-therapy with a sPLA2 inhibitor also allows antivenoms to be used when there is no no antivenom known or available for the particular snake type, or the type of envenomation is unknown (e.g. the snake, fish or invertebrate, e.g. scorpion or spider, is not known. Co-therapy with a sPLA2 inhibitor may also allow lower doses of antivenom to be administered. The ability of prinomastat and other MP inhibitors to improve the performance of Crofab® indicates that coadminsitration of MP inhibitors and antivenom may be used to treat subjects for envneomation.

The present application below lists specific and paraspecific antivenoms and antivenom-based compositions that may be used in combination with a small molecule PLA2 inhibitor (e.g., a 1H-Indole-3-glyoxylamide, such as varespladib and/or methylvarespladib) to treat evenomation by vertebrate or invertebrates.

Exemplary Antivenoms

Non-limiting list of snake antivenoms for which varespladib and methylvarespladib can improve outcomes by improving the efficacy of the antivenom formulations by prior administration, co-administration or co-formulation.

Pit Viper Antivenom, produced by Pfizer Inc, Pit Viper Antivenom (Crotalidae) is a Polyvalent equine antisera product which is a refined and concentrated preparation of serum globulins obtained by fractionating blood from healthy horses immunized with the following venoms: *Crotalus adamanteus* (Eastern diamond rattlesnake), *C. atrox* (Western diamond rattlesnake), *C. durissus terrificus* (tropical rattlesnake, Cascabel) and *Bothrops atrox*. Pit Viper Antivenom is indicated for the treatment of envenomation caused by bites of crotalids (pit vipers);

Anavip Snake Venom, Instituto Bioclon SA de CV, Rare Disease Therapeutics Inc: Anavip contains equine crotalinae F(ab')2 immunoglobulin fragments as an active ingredient;

Anti-Snake Venom Serum Snake Venom by Indian Drugs & Pharmaceuticals Ltd. Anti-Snake Serum contains polyvalent equine snake venom immunoglobulins is indicated for the treatment against snake bites;

Anti-Vipers Serum VACSERA Snake Venom Poisoning by The Holding Company for Biological Products & Vaccines (VACSERA). Anti-Vipers Serum contains polyvalent viper venom antiserum. It is indicated for the treatment of viper bite.

Antivenom PFIZER INC. Antivenom (*Micrurus fulvius*) is a refined, concentrated, and lyophilized preparation of serum globulins obtained by fractionating blood from healthy horses that have been immunized with eastern coral snake (*Micrurus fulvius*) venom;

Antiviperino BIRMEX Snake Venom Poisoning, Laboratorios de Biologicos y Reactivos de Mexico S A de C V (Birmex). Antiviperino contains Vipera berus venom immunoglobulins;

ASVS-Africa Snake Venom Poisoning, Bharat Serums And Vaccines Limited, is a polyvalent snake antitoxin. It is a refined and concentrated preparation of serum globulins obtained by fractionating blood from healthy horses which are hyperimmunized by venoms of different snakes. ASVS-Africa is indicated for the treatment of envenomation caused by snake bites.

ASVS-Asia Snake Venom Poisoning, Bharat Serums And Vaccines Limited, Globulins, ASVS-Asia is a polyvalent snake venom antiserum. Snake venom antiserum is a refined and concentrated preparation of serum globulins obtained by fractionating blood from healthy horses which are hyperimmunized by venoms of different snakes;

Black Snake Antivenom CSL LTD Snake Venom Poisoning, CSL Limited. Black Snake Antivenom is prepared from the plasma of horses immunized with the venom of the king brown snake (*Pseudechis australis*) also known as the mulga snake and then collecting that part of the horse's blood which neutralizes this poison. The venom of the king brown snake contains neurotoxins, myolytic toxins and an anticoagulant toxin. Black Snake Antivenom is used for the treatment of patients who exhibit manifestations of systemic envenoming following a bite by a king brown or mulga snake and related species and subspecies "paraspecific" antivenom use.

Bothrofav Snake Venom Poisoning, Sanofi, Antibodies, Globulins, Immunoglobulins, Immunoproteins, Serum Globulins, BothroFav is an F(ab')2-containing antiserum used for the treatment of envenomation of *Bothrops lanceolatus* snakes;

Brown Snake Antivenom Snake Venom Poisoning, CSL Limited, Antibodies, Antitoxins, Biological Factors, Globulins, Immunoproteins, Peptides, Serum Globulins, Brown Snake Antivenom is prepared from the plasma of horses immunized with the venom of the brown snake (*Pseudonaja textilis*). Brown Snake Antivenom is indicated for the treatment of patients who exhibit manifestations of systemic envenoming following a bite by a snake of the genus *Pseudonaja*. This genus includes the Eastern brown snake, the dugite and the gwardar (Western brown snake);

Coralmyn Snake Venom Poisoning, Instituto Bioclon SA de CV, Toxins, Biological, Coralmyn is a polyvalent anticoral fabotherapetic containing fragments F(ab')2 and Fab of immunoglobulin G (IgG);

Serum Globulins, CroFab® (BTG) contains ovine crotalidae immunoglobulin fragments as an active ingredient. Crotalidae Polyvalent Immune Fab (Ovine) is a venom-specific Fab fragment of immunoglobulin G (IgG) that works by binding to and neutralizing venom toxins, facilitating their redistribution away from target tissues and their elimination from the body.

Death Adder Antivenom CSL LTD Snake Venom Poisoning, CSL Limited is prepared from the plasma of horses immunized with the venom of the death adder (*Acanthophis antarcticus*). Death Adder Antivenom is indicated for the treatment of patients who exhibit manifestations of systemic envenoming following a bite by a death adder;

Fav-Afrique, Sanofi, Globulins, FAV-Afrique is a polyvalent snake antivenom, elaborated by immunization of horses with venom from 10 different snake species among the most dangerous in Africa and belonging to Elapidae and Viperidae families. Only F(ab')2 fragments are kept and purified. This serum is able to decrease the quantity of circulating venom and therefore its toxicity. Favirept (Sanofi Pasteur) is a polyvalent equine F(ab')2 antivenom indicated for snakebite in the Middle East snakes: *Bitis, Echis, Naja, Cerastes*, and *Macrovipera*;

Freeze-dried Habu Antivenom produced by KAKETSUKEN. Freeze-dried Habu Antivenom contains *Trimeresurus flavoviridis* immunoglobulin of equine origin. Freeze-dried Mamushi Antivenom (KAKETSUKEN) is of equine origin;

Polyvalent Snake Antivenom CSL LTD polyvalent Snake Antivenom contains antibodies to the venom of the following snakes King brown snake (*Pseudechis australis*), Tiger snake (*Notechis scutatus*), Brown snake (*Pseudonaja textilis*), Death adder (*Acanthophis antarcticus*), Taipan (*Oxyuranus scutellatus*). The antivenom is prepared from the plasma of horses immunized with the venom of these snakes. It is indicated for the treatment of patients in Papua New Guinea and in all Australian states except Victoria and Tasmania;

Sea Snake Antivenom (CSL Limited). Sea Snake Antivenom is prepared from the plasma of horses immunized with the venom of the sea snake *Enhydrina schistosa*. Sea Snake Antivenom is indicated for the treatment of patients who exhibit manifestations of systemic envenoming following a bite by a sea snake;

Polyvalent Anti Snake Venom Serum by Serum Institute of India Ltd is a polyvalent anti-snake venom serum is prepared from hyperimmunized horses against the venoms of the four most commonly encountered venomous snakes in India;

BIOLOGICAL E by Biological E. Limited antivenom is a polyvalent preparation that is a pepsin-digested, refined and concentrated preparation obtained from equine hyper immune serum. It is used to neutralize the venom of *Echis carinatus, Naja naja, Bangarus caeruleus* and *Vipera (Daboia) russelli*.

VINS Bioproducts Ltd produces antiserum contains snake venom immunoglobulins (equine) as an active ingredient. Snake Venom Vaccine by United Company for Biological Industries Ltd (Bio Egypt is indicated as prophylactic vaccine against snake bites;

Taipan Antivenom by CSL LTD is a Taipan Antivenom prepared from the plasma of horses immunized with the venom of the taipan snake (*Oxyuranus scutellatus*) and similar preparations;

Tiger Snake Antivenom by CSL LTD is prepared from the plasma of horses immunized with the venom of the tiger snake (*Notechis scutatus*). Tiger Snake Antivenom is indicated for the treatment of patients who exhibit manifestations of systemic envenoming following a bite by a tiger, copperhead or black snake;

ViperaTAb contains Vipera berus venom immunoglobulins as an active ingredient. It is a polyvalent immune fab (Ovine), comprising of specific antibody fragments that bind and neutralize *Vipera berus* venom components, including proteases, lipases and cardiotoxins, facilitating their redistribution away from target tissues and subsequent elimination from the body;

Viperfav (Sanofi) is a polyvalent equine F(ab')2 immunoglobulin antivenom indicated for the prevention of poisoning against European snakes (*Vipera* sp);

Snake Antiserum (KAMADA) Antivipmyn by Instituto Bioclon SA de CV contains snake venom immunoglobulin fragments (equine) as an active ingredient. It is a polyvalent anti snake fabotherapeutic containing fragments F(ab')2 of immunoglobulin G (IgG) hyperimmunoglobulins.

List of Specific and paraspecific Invertebrate antivenoms with efficacy being enhanced by varespladib and methylvarespladib and combinations thereof:

Box Jellyfish Antivenom CSL LTD Jellyfish, CSL Limited Box Jellyfish Antivenom is prepared from the plasma of sheep immunized with the venom of the box jellyfish (*Chironex fleckeri*). Analatro (Instituto Bioclon SA de CV and Rare Disease Therapeutics Inc contains latrodectus venom F(ab')2 immunoglobulin fragments as an active ingredient;

Aracmyn Plus by Instituto Bioclon SA de CV and Rare Disease Therapeutics Inc contains polyvalent spider venom F(ab')2 immunoglobulin as active ingredient;

Funnel Web Spider Antivenom Poisoning, CSL Limited: Funnel Web Spider Antivenom is a purified immunoglobulin (mainly immunoglobulin G), derived from rabbit plasma *Atrax robustus*;

Reclusmyn Instituto Bioclon SA de CV: Reclusmyn contains immune F(ab')2 antivenom.

Red Back Spider Antivenom Poisoning, CSL Limited. Red Back Spider Antivenom is prepared from the plasma of horses immunized with the venom of the female red back spider (*Latrodectus hasselti*);

Stonefish Antivenom (CSL Limited) is prepared from the plasma of horses immunized with the venom of the stonefish (*Synanceia trachynis*);

Scorgen is produced by Bharat Biotech International Limited. Scorgen consists of scorpion venom antiserum, which is of equine origin. This antiserum contains purified, enzyme refined and concentrated specific heterologous immunoglobulins;

Anascorp Instituto Bioclon SA de CV, Accredo Health Group Inc, Rare Disease Therapeutics Inc. Anascorp contains Centruroides immunoglobulin fragments (equine);

Anti-Scorpion Serum VACSERA Scorpion. Anti-Scorpion Serum is a purified polyvalent scorpion antiserum;

Scorpifav Scorpion, Scorpifav is a polyvalent equine F(ab')2 antivenom. Scorpifav is indicated for the prevention of poisoning against North African and Middle East scorpions (*Androctonus, Leiurus, Buthus*);

Scorpion venom antiserum Scorpion, VINS Bioproducts Ltd. Scorpion venom antiserum contains of scorpion venom immunoglobulin fragments (equine) as an active ingredient. Scorpion venom antiserum is indicated for the treatment of scorpion bite;

Scorpion Venom Vaccine Scorpion, United Company for Biological Industries Ltd (Bio Egypt). Scorpion Venom Vaccine is indicated as prophylactic vaccine against scorpion sting;

Scorpion Venoms Antitoxin by United Company for Biological Industries Ltd (Bio Egypt). Scorpion Venoms Antitoxin contains immunoglobulins against scorpion venom with the ability to neutralize toxins;

Stop Itch Skin Rash, Valeant Pharmaceuticals Australasia Pty Ltd. The active ingredient in Stop Itch is Papain, an enzyme extracted from the unripe fruit of paw paw (*Carica papaya*). Papain works two ways by inhibiting sensory transmission and neutralizing insect venom to quickly soothe and reduce the pain, itching and swelling associated with insect bites and minor skin irritations;

CSL Tick Antivenom Tick Antivenom helps to neutralize the effect of the *Ixodes holocyclus* venom. The antivenom is produced by immunizing dogs Tick Antivenom is indicated for the treatment of patients showing evidence of paralysis as a result of tick poisoning.

VI. Metalloproteinase Inhbitors

In one aspect cotherapy of a PLA2 inhibitor (e.g., an 1H-Indole-3-glyoxylamide, such as varespladib and/or methylvarespladib) is used in combination with a small molecule with inhibitor activity agains a snake venom metalloproteinase.

Useful "metalloproteinase inhbitors" include, but are not limited to, Prinomastat, BB-94 (ma rimastat), BB-2516 (batimastat), vorinostat, cefixime, ginkolide. Other metalloproteinase inhbitors that may be used in the invention include but are not limited to, TAPI-2, TAPI-1, EGTA, EDTA, phosphoramadon, TAPI-0, Luteolin, alendronate, tanomastat, ilomastat, prinomastat, nafamostat, collagenase inhibitor 1, Ro-32-3555, lactobionic acid, o-phenantroline, ecotin, 4-epi-chlortetracycline, teracycline, doxycycline or related antibiotic with additional, salutary antimicrobial effect, n-dansyl-d-phenylalanine, 20[R]ginsenosideRh2, pro-leu-gly-hydroxymate, gm6001, actinonin, a rp-100, MMP9 inhibitor I, MMP2 inhibitor I, SB-3CT, Thiorphan (DL), 4-epi-demeclocycline, zinc methacrylate, funalenone, naturally derived or synthetic short peptide-inhibitor of snake venom metalloproteinase and analogs, derivatives, pharmaceutically acceptable salts, enantiomers, diastereomers, solvates and polymorphs and mixtures thereof.

Unexpectedly, a combination of varespladib and/or methylvarespladib without and with certain metalloproteinase inhibitors likely prove effective in the treatment of bites for every major venomous snake in Japan, many if not all American vipers and others from around the world. Further, co-administration of varespladib and/or methylvarespladib with or without neostigmine or pyridostigmine and optionally atropine or glycopyrrolate will treat effectively bites of every coral snake found in the Americas, a discovery with profound therapeutic implications as it enables immediate treatment of life-threatening symptoms, especially through self-administration of therapeutics by a victim at the time of envenomation.

In some embodiments the MP inhibitor is an inhibitor described below in Example 12 ("HTS Discovery Of Useful Inhibitors Of *C. Atrox* Venom MP (Representing New World Vipers)") or Example 13 ("Example 13 HTS Discovery Of MP Inhibitors Against *E. Carinatus* (Representing Old World Vipers").

VII. Serine Protease Inhibitors

In one aspect cotherapy of a PLA2 inhibitor (e.g., a 1H-Indole-3-glyoxylamide, such as varespladib and/or methylvarespladib) is used in combination with a small molecule with inhibitory activity agains a snake venom serine protease.

Useful serine protease inhibitors include, but are not limited to, nafamostat and gabexate, camostat or camostate and unexpectedly in certain instances, varespladib and methylvarespladib themselves. In certain instances cited herein, above and below, gabexate, camostat or camostate and other inhibitors directly or indirectly suppress snake venom or host PLA2 activity with salutary effect following snakebite or other envenomation. Other useful serine protease inhibitors include, but are not limited to, aprotinin, leupeptin, antithrombin (AT), alpha-1 antitrypsin ($\alpha_1$-antitrypsin (A1AT)), AEBSF (4-(2-aminoethyl) benzenesulfonyl fluoride hydrochloride), PMSF (phenylmethanesulfonylfluoride or phenylmethylsulfonyl fluoride), protein C inhibitor (PCI, SERPINAS), protein Z-dependent protease inhibitor, methoxy arachidonyl fluorophosphonate (MAFP), myeloid and erythroid nuclear termination stage-specific protein (MENT), plasminogen activator inhibitor-1 (PAI-1), plasminogen activator inhibitor-2 (placental PAI), protease-nexin-1 (PN-1), antithrombin III colligin, phosphatidylethanolamine-binding protein, neuroserpin, $\alpha_2$-antiplasmin, serine protease inhibitor 3, murinoglobin I, a naturally derived or synthetic short peptide-inhibitor of snake venom serine protease, ribozymes and small molecule agents that reduce the transcription or translation of a serine protease polynucleotide as described in U.S. Patent Application Document No. 20090318534, the serine protease inhibitors described or referenced in U.S. Patent Application Document No. 20140341881 and analogs, derivatives, pharmaceutically acceptable salts, enantiomers, diastereomers, solvates, polymorphs and mixtures thereof.

VIII. Other Agents

A. Acetylcholinesterase Inhibitors

Acetylcholine (ACh) is a neurotransmitter synthesized in the cytoplasm of nerve cells and in non-neuronal tissues such as those found in the mucosal surfaces of the head and neck. When an action potential reaches a nerve ending, a vesicle releases acetylcholine into a synapse. Once in the synapse, acetylcholine diffuses across the synaptic cleft and binds with a post-synaptic acetylcholine receptor. The binding of acetylcholine to its receptor triggers depolarization of the post-synaptic cell. The receptor-mediated response is subsequently terminated when acetylcholine is hydrolyzed by an acetylcholinesterase to acetic acid and choline. Acetylcholinesterase (AchE; EC 3.1.1.7) is a serine protease that hydrolyzes acetylcholine. Assays for acetylcholinesterase activity are known (see, e.g., Ellman et al., *Biochem. Pharmacol.*, 7, 88-95, 1961).

Acetylcholine binds to two main types of receptors, the nicotinic acetylcholine receptor (nAChR) and the muscarinic acetylcholine receptor (mAChR). Nicotinic acetylcholine receptors are generally found in the plasma membranes of certain neurons and on the postsynaptic side of neuromuscular junctions (which controls skeletal muscles). Muscarinic acetylcholine receptors are generally found in organs involved in the parasympathetic nervous system. The deleterious effects of neurotoxic venoms, or residual effects of nondepolarizing neuromuscular blocking agents (NNBAs), can be counteracted by inhibiting acetylcholinesterase at the neuromuscular junction. Acetylcholinesterase terminates the nAChR response by hydrolyzing ACh to acetic acid and choline. It is possible that inhibiting acetylcholinesterase activity prevents the hydrolysis of ACh, which increases the effective ACh concentration in the neuromuscular junction and thereby ameliorates the effect of the α-neurotoxins and other neurotoxins such as β-neurotoxins, or residual effects of NNBAs.

Neurotoxins (such as alpha- and beta-neurotoxins) found in snake venom compete with or block ACh for binding to nicotinic acetylcholine receptors. Most deaths from acetylcholine-modulating neurotoxins are caused by skeletal muscle paralysis from presynaptically targeted toxins preventing nerve function ("pre-synaptic") or at the Ach receptor sites associated with direct activation of muscle contraction ("post-synaptic") side. Together, these make and up the neuromuscular junction and failure or disruption of these mechanisms this triggers respiratory failure and unless the victim is treated, results in death. In general, the mechanism of action of these neurotoxins is the disruption of the normal function of the nAChR by decreasing the effective concentration of ACh that is available for binding to the neuromuscular junction. This occurs because neurotoxins are antagonists of nAChR and compete with ACh for the nAChR binding site or damage the synapse itself, compromising the ability of the neuron to release ACh. The severity of the physiological response of the venom/neurotoxin is directly correlated with the affinity of the neurotoxin for the nAChR or the nerve terminals responsible for releasing ACh or both.

Useful acetylcholinesterase inhibitors include, but are not limited to, ambenonium; demarcarium; donepezil; edrophonium; galantamine; huperzine A; ladostigil; lactucopicrin; neostigmine; physostigmine; pyridostigmine; rivastigmine; tacrine; phospholine iodide; and ungeremine.

Useful mAChR antagonists include competitive antagonists. The mAChR antagonist can be a reversible competitive antagonist and preferably does not cross the blood brain barrier. Preferably, the mAChR antagonist is selective for mAChR over the nAChR and has a half-life of 4 to 6 hours or less. Useful mAChR agonists include, but are not limited to, glycopyrrolate and atropine, and preferred acetylcholinesterase inhibitor-mAChR antagonist co-therapy combinations include neostigmine and glycopyrrolate or atropine. Exemplary combinations of adjuvant therapeutics that can be co-administered with the metalloproteinase inhibitor, $PLA_2$ inhibitor and serine protease inhibitor include phospholine iodide, an oxime-derived AChE restoring agent such as pralidoxime and a mAChR inhibitor such as atropine or biperiden. In one embodiment, the mAChR antagonist is selected from the group consisting of atropine, benzatropine, glycopyrrolate, ipratropium, mebeverine, oxybutynin, pirenzepine, scopolamine, biperiden, tiotropium and tropicamide.

B. NMDA Receptor Antagonists

"NMDA receptor antagonists" include, but are not limited to, dizocilpine (MK801), ifenprodil, R025-6981, TCN-201, ketamine, fluorofelbamate, felbamate, memantine, dextromethorphan, eliprodil, selfotel, Conantokin-G, -R, aptigamel (CNS1102), dynorphin A(1-13), DQP 1105, and NVP-AAM077.

C. Antibiotics

Useful venom-inhibiting antibiotics include, but are not limited to, Demeclocycline, Doxycycline, Vibramycin Minocycline, Tigecycline, Oxytetracycline, Tetracycline, Gentamicin, Kanamycin, Neomycin, Netilmicin, Tobramycin, Paromomycin, Spectinomycin, Geldanamycin, Herbimycin, Rifaximin, Streptomycin, Ertapenem, Doripenem, Imipenem/Cilastatin, Meropenem, Cefadroxil, Cefazolin, Cephalothin, Cephalexin, Cefaclor, Cefamandole, Cefoxitin, Cefprozil, Cefuroxime, Cefixime, Cefdinir, Cefditoren, Cefoperazone Cefotaxime, Cefpodoxime, Ceftazadime, Ceftibuten, Ceftizoxime Ceftriaxone, Cefepime, Ceftaroline fosamil, Ceftobiprole, Teicoplanin, Vancomycin, Telavancin, Daptomycin, Oritavancin, WAP-8294A, Azithromycin, Clarithromycin, Dirithromycin, Erythromycin, Roxithromycin, Telithromycin, Spiramycin, Clindamycin, Lincomycin, Aztreonam, Furazolidone, Nitrofurantoin, Oxazolidonones, Linezolid, Posizolid, Radezolid, Torezolid, Amoxicillin, Ampicillin, Azlocillin, Carbenicillin, Cloxacillin Dicloxacillin, Flucloxacillin, Mezlocillin, Methicillin, Nafcillin, Oxacillin, Penicillin G, Penicillin V, Piperacillin, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Mafenide, Sulfacetamide, Sulfadiazine, Sulfadimethoxine, Sulfamethizole, Sulfamethoxazole, Sulfasalazine, Sulfisoxazole, Trimethoprim-Sulfamethoxazole, Su lfonamidochrysoidine, Clofazimine, Capreomycin, Cycloserine, Ethambutol, Rifampicin, Rifabutin, Rifapentine, Arsphenamine, Chloramphenicol, Fosfomycin, Fusidic acid, Metronidazole, Mupirocin, Platensimycin, Quinupristin/Dalfopristin, Thiamphenicol, Tigecycline and Tinidazole and combinations thereof.

Particularly useful venom inhibiting antibiotics treat snakebite-related microbes and act as venom neutralizing agents. Examples of such antibiotics include cephalosporins such as cefixime and tetracyclines such as doxycycline and demeclocycline.

D. Distribution Enhancing Agents

In addition to the above components, compositions and methods according to the present invention may be enhanced by the inclusion of an effective amount of an agent which promotes biodistribution, such as, for example lidocaine and/or bupivacaine, which may be included in compositions according to the present invention to enhance distribution of the active components in the tissue into which the composition is injected while relaxing smooth muscle and slowing venom spread.

E. Spreading Factor Inhibitors

Methods of treatment and pharmaceutical compositions of the invention can inhibit angiogenesis associated with snakebite through use of "spreading factor inhibitors". "Spreading factor inhibitors" encompass inhibitors of the vitronectin receptor $\alpha_5\beta_3$ including, but not limited to those vitronectin receptor $\alpha_5\beta_3$ inhibitors described or referenced in U.S. Pat. No. 8,546,526, and those inhibitors of plasminogen activator inhibitor-1 (PAI-1; SERPINE1) described or referenced in Simone, et al., "Chemical Antagonists of Plasminogen Activator Inhibitor-1: Mechanisms of Action and Therapeutic Potential in Vascular Disease", *J Mol Genet Med*, Volume 8, Issue 3, 1000125 (2014). XR330, XR334, XR1853, XR5082, XR5967, XR1121, AR-H029953XX, fendosalanthranalic acid derivatives of the fibrinolytic antagonist flufenamic acid, ANS, bis-ANS, 1-dodecyl sulphurc acid, XR-5118 CDE-066, CDE-081, IMD-1622, Tiplaxtinin and TM5007. Useful spreading factor inhibitors also include naturally derived or synthetic short peptide-inhibitors of snake venom spreading factors and naturally derived or synthetic short peptide-inhibitor of non-enzymatic, tissue destructive, cardiotoxic, myotoxic, paralytic or hemorrhagic toxins. Lidocaine and other -caines can relax lymphatic smooth muscle and slow the spread of venom. Physical spreading factor inhibitors include pressure immobilzation devices can be used in conjunction with the present invention to slow the spread of venom and increase the time window to definitive or adjunct treatment.

IX. Dosages and Routes of Administration

Generally, dosages and routes of administration of the pharmaceutical compositions and therapeutic compounds described herein are determined according to the size and condition of the subject, according to standard pharmaceutical practices. Dose levels employed can vary widely, and can readily be determined by those of skill in the art. Typically, amounts in the milligram up to gram quantities are employed.

Formulations comprising a drug, prodrug or combinations described herein (e.g., varespladib or methylvarespladib, a produg of varespladib and other inhibitor compounds when included in compositions according to the present invention) and saline are provided. In one aspect, such formulations are at physiologically acceptable pH (e.g., about 7.4-8.5) e.g. when solubilized in 58% v/v 8.4% bicarbonate and 42% v/v 10% dextrose solution. Such formulations may be amenable to storage and subsequent use with the drug, prodrug or combinations remaining intact for prolonged periods of time (e.g., during storage) and converted to varespladib with or without other components after administration to an individual (e.g., an adult, child, or infant). In some embodiments, the drug, prodrug or combinations are stored as a dry powder or powders (especially a lyophilized powder) and the formulation is generated by dissolving the dry powder in saline or other diluent prior to administration. In one aspect, formulations are provided, e.g., formulations comprising the drug, prodrug or combinations at molar equivalents of about any of 1 ng/mL to 1 ug/mL to 0.01, mg/mL, 0.1 mg/mL, 1 mg/mL, 5 mg/mL, 10 mg/mL, 25 mg/mL, 50 mg/mL, 75 mg/mL, 100 mg/mL, 125 mg/mL, 150 mg/mL, 175 mg/mL, or 200 mg/mL or 400 mg/mL or 600 mg/mL or 800 mg/mL or 1000 mg/mL of parent drug (e.g., varespladib), wherein the molar equivalent of drug, prodrug or combinations is the amount of drug, prodrug or combinations that would result in the indicated amount of parent drug upon complete conversion. For any amount (e.g., dosage) of drug, prodrug or combinations described herein, also contemplated is the molar equivalent of prodrug for that amount of parent drug. Single bolus formulations are also provided, e.g., up to about any of 5 mL, 10 mL, or 15 mL (at, for example, the stoichiometric prodrug equivalent of about 1450 mg to about 1600 mg of parent drug, such as varespladib) or in examples of pill, capsule or oral elixir forms: 1 mg to 100 mg, 250 mg, 500 mg, 1000 mg for oral dosing once, twice, three times per day to achieve serum concentrations of 10 pM, 100 pM, 1 nM, 10 nM, 50 nM, 100 nM, 200 nM, 500 nM, 1 uM, 10 uM, 100 uM and in non-human animals up to 1, 10, 25, 50, 100, 150 mg/kg/day but preferably 0.5 to 100 mg/kg/day in single or divided doses.

The dosage administered will vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active compound can be about 0.1 to 500 milligrams per kilogram of body weight. Ordinarily 0.5 to 50, and preferably 1 to 25 milligrams per kilogram per day given in divided doses 1 to 6 times a day or in sustained release form is effective to obtain desired results. Depending on the patient's state, a lower dose range or a higher dose range is given prior to the onset of symptoms or signs of snakebite or invertebrate bite or sting inducing conditions (i.e., as determined clinically or potentially by increase in sPLA2 levels in a hospital setting), while a higher dose may be given when aggressive intervention is indicated to combat rising sPLA2 levels.

In general, the sPLA2 inhibitor will be administered to an animal so that a therapeutically effective amount is received. A therapeutically effective amount may conventionally be determined for an individual patient by administering the active compound in increasing doses and observing the effect on the patient, for example, reduction in paralysis, tissue damage or suppression of increasing sPLA2 activity levels, or a reduction in other symptoms or signs associated with snakebite or invertebrate bite or sting.

Generally, the compound should be administered in a manner and a dose to achieve in the animal a blood level concentration of sPLA2 or other inhibitor of from 0.01 to 5000 nanograms/ml and preferably a concentration of 1 to 1000 nanograms/ml.

The treatment regimen may stretch over a number of hours to a day to several weeks to months or to years as determined by a competent caregiver (treating physician). Oral dosing and/or intravenous infusion are preferred for patient convenience and tolerance. With oral dosing, one to four oral doses per day, each from about 0.01 to 100 mg/kg of body weight with preferred doses being from about 0.1 mg/kg to about 10 mg/kg.

X. Dosage Forms, Pharmaceutical Formulations; Modes of Delivery

The active compounds (especially including the IH-indole-3-glyoxylamide compounds varespladib and methylvarespladib may be used at a concentration of 0.01 to 99.9 weight percent of the formulation, or in some cases a concentration of 0.001 to 99.9 weight percent of the formulation. Preferably the pharmaceutical formulation is in unit dosage form. The unit dosage form can be a capsule or tablet itself, or the appropriate number of any of these. The quantity of active compound in a unit dose of composition may be varied or adjusted from about 0.1 to about 1000 milligrams or more according to the particular treatment involved.

Compositions (dosage forms) suitable for internal administration contain from about 1 milligram to about 1000 milligrams of active compound per unit. In these pharmaceutical compositions the active compound will ordinarily be present in an amount of about 05-95% by weight based on the total weight of the composition. Examples of useful pharmaceutical compositions and their proportions of ingredients are illustrated as follows:

Capsules: Capsules may be prepared by filling standard two-piece hard gelatin capsules each with 50 mg of powdered active compound, 175 mg of lactose, 24 mg of talc, and 6 mg of magnesium stearate.

Soft Gelatin Capsules: A mixture of active compound in soybean oil is prepared and injected by means of a positive displacement pump into gelatin to form soft gelatin capsules containing 50-500 mg of the active compound. The capsules are washed in petroleum ether and dried.

Tablets: Tablets may be prepared by conventional procedures so that the dosage unit is 50 mg of active compound, 6 mg of magnesium stearate, 70 mg of macrocrystalline cellulose, 11 mg of cornstarch, and 225 mg of lactose. Appropriate coatings may be applied to increase palatability or delay absorption.

Suspensions: An aqueous suspension is prepared for oral administration so that each 5 ml contain 25 mg of finely divided active compound, 200 mg of sodium carboxymethyl cellulose, 5 mg of sodium benzoate, 1.0 g of sorbitol solution, U.S. P., and 0.025 mg of vanillin.

Injectables: A parenteral composition suitable for administration by injection is prepared by stirring 1.5% by weight of active compound in 10% by volume propylene glycol and water. The solution is sterilized by commonly used techniques. Other injectables are prepared from powders, especially lyophilized powders that are dissolved in saline solution at medically acceptable pH).

Nasal Spray: An aqueous solution is prepared such that each 1 ml contains 10 mg of active compound, 1.8 mg methylparaben, 0.2 mg propylparaben and 10 mg methylcellulose. The solution is dispensed into 1-5 ml vials.

Aerosol formulations are capable of dispersing into particle sizes of from about 0.5 to about 10 microns and have sufficient sPLA2 inhibitor to achieve concentrations of the inhibitor on the airway surfaces of from about $10^{-10}$ to $10^{-2}$ moles per liter.

Parenteral administration (particularly, intravenous administration) is often preferred in instances where rapid alleviation of patient distress is required such as when analysis shows an increase in sPLA2 levels or up to 24 hours after the first organ failure. With parenteral administration doses of 0.001 to 200 mg/kg/day administered continuously or intermittently throughout the day may be used. For parenteral administration, the compound may be administered in a physiologic saline vehicle (e.g., 0.9%-normal saline, 0.45% normal saline, etc.) a dextrose vehicle (e.g., 5% dextrose in water), or a combination of saline and dextrose vehicle (0.9% normal saline in 5% dextrose) and might or might not include sodium bicarbonate 4.2%-8.4% in order to increase pH of solution to >8.0 for parenteral administration.

Parenteral administration is also preferably effected by use of a freeze dried lyophilized composition (s) of a compound useful for the practice of the present invention.

Compositions according to the present invention may be administered to the patient alone, in combination in a single dosage form or sequentially in more than one composition (in any order). Dosage forms of the present compositions may include solid compositions which are dried and available for reconstitution in the field, solutions for injection or oral administration or the compositions may be incorporated into mixtures or prepared as individual components to be given in sequence following a suspected or confirmed envenomation. In certain embodiments, the composition dosage form is a parenteral dosage form that is formulated for injection by needle or jet (e.g. intramuscularly, subcutaneously) or intravenous infusion for immediate or sustained release. Other dosage forms are adapted for administration by microinjection or patch (transdermal administration) alone or underneath a pressure immobilization splint, intranasally, orally as a pill, elixir or solution, buccally, sublingually, as a gel, aerosolized with pharmaceutically active or inert carriers with or without additional properties such as antibiotic and analgesic activity and optionally delivered in vesicles encompassing liposomes, micelles, polymeric, metallic and lipid nanoparticles among others as well as penetrating agents to enhance tissue delivery.

Dosage and Test Product—varespladib (LY315920) or methylvarespladib, supplied. Administration: as a lyophilized powder dissolved in saline with an appropriate solubilizer as needed and injected. Each vial can contain 0.1, 1, 10, 50, 100, 250, 500, 750, 1000, 2000, 5000 to 50,000 mg varespladib, with appropriate portions metered from package into solution. Following reconstitution, all doses of varespladib targeting varespladib plasma concentrations of approximately 1 and 2500 ng/mL, preferably about 1000 ng/mL. In preferred aspects of the invention, varespladib serum concentrations reach 500 ng/mL to about 1500 ng/mL, preferably about 750 ng/mL to about 1250 ng/mL and most preferably about 1000 ng/mL (1 µg/mL) serum concentration for maximum therapeutic effect. Other $PLA_2$ inhibitors will vary in concentration, most considerably higher than varespladib as a consequence of their activity generally being diminished compared to varespladib. In some embodiments metalloproteinase inhibitors and/or serine protease inhibitors, are administered to reach a serum concentration ranging from about 0.1 ng/mL to about 500 µg/ml.

Modes of delivery, doses and routes of administration are expected to vary by stage of care. For illustration, a human or non-human patient is bitten by a snake and administers a pharmaceutically effective dose of the antidote composition by intramuscular injection and seeks medical care at an appropriate facility where the patient could receive antivenom with or without the antidote or the antidote with or without antivenom in the form of an intravenous injection, as a pill, sponge, repeat injection, nasal spray or other aerosol delivery for the purpose of maintaining sufficient blood levels to continue inhibiting venom until the patient is stabilized or it is determined that no other treatment is necessary.

Exemplary dosage ranges for the metalloproteinase inhibitor, $PLA_2$ inhibitor and serine protease inhibitor include amounts of the inhibitors sufficient, when dispersed, dissolved or diluted with a pharmaceutically-acceptable carrier (excipient) to yield inhibitor concentrations of between about 0.000001, 0.00001, 0.0001, 0.001, 0.01, 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 230, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 525, 550, 575, 600, 625, 650, 675, 700, 725 to about 750 µM or as high as 800, 850, 900, 950 or 1,000 µM. These exemplary dosage ranges also apply to the adjuvant therapeutics described herein. Dosages of between about about 0.000001, 0.00001, 0.0001, 0.001, 0.01, 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 230, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 to about 500 µM are possible.

In certain embodiments, the therapeutically active agents described herein are administered locally to a bite or sting site as a paste or gel to neutralize deposited venom. In some embodiments, a first therapeutic agent is administered directly or proximally to a bite site or damaged tissue, while a second therapeutic agent is co-administered by another route (optionally in combination with a traditional antivenom as adjunct treatment). In some embodiments, therapeutically active agents are administered in lieu of antivenom for non-lethal or non-limb threatening injuries (e.g. isolated facial paralysis or cranial nerve palsy). In some embodiments the therapeutically active agent(s) is administered by transdermal patch or in conjunction with a pressure-immolization device used to slow the spread of venom by decreasing lymphatic flow.

In some embodiments, the inhibitors described herein are conjugated to another molecule such as a biocompatible and/or biodegradable nanoparticle. For example, an inhibitor may be combined with another drug that combats the hemotoxic effects of complex venoms and prevents clotting disorders by preventing the consumption of fibrin or other clotting factors alone or in combinations such as mixtures or conjugates. In some embodiments, the antidote is combined with herbal extracts or other compounds that inhibit phospholipase A2 preventing clotting disorders and degradation of the pre-synaptic neurons at the neuromuscular junction. In some embodiments, the combined antidotes are combined with permeation enhancers.

The therapeutically active agents used in the methods and pharmaceutical compositions of the invention can be administered in a wide variety of ways. Exemplary routes of administration include direct needle injection, jet or other propulsive injection, intravenous administration, direct application to a bite site, ocular exposure and affected tissues (topical, transdermal), inhalation, intranasal administration, and sublingual, rectal, vaginal, oral or ocular administration. Methods for preparing such dosage forms are known or is apparent to those skilled in the art; for example, see Remington's Pharmaceutical Sciences (17th Ed., Mack Pub. Co., 1985). The composition to be administered will contain a quantity of the selected compound in a pharmaceutically effective amount for therapeutic use in a biological system, including a patient or subject according to the present invention.

Generally, the metalloproteinase inhibitor, $PLA_2$ inhibitor and/or a serine protease inhibitor and optional adjuvant therapeutic agent(s) are administered as soon as possible following identification of the envenomated subject/patient. If the subject/patient exhibits signs of neurotoxin envenomation, one or more of the aforementioned active ingredients is administered immediately. In some approaches, therapy is initiated when there is reason to believe that the subject has suffered a venomous bite or sting (e.g. the subject expresses symptoms such as pain, shortness of breath, bleeding, bruising), or when the snake is identified as being one known to inject neurotoxins. Multiple administrations may be indicated over time, depending on a subject's response or to prevent symptoms prior to professional medical attention (e.g. appearance or progression of signs of paralysis). For example, a 1%-10% solution of a $PLA_2$ inhibitor, metalloproteinase inhibitor and/or a serine protease inhibitor, preferably a $PLA_2$ inhibitor and metalloproteinase inhibitor (and optional adjuvant therapeutic (e.g. an acetylcholinesterase inhibitor and a mAChR antagonist)) may be administered at 15 minute to 12 hour intervals or longer. Administration of active ingredient(s) several times per day may be necessary or the administration of an extended release formulation.

In one embodiment, the practice of the present invention involves use of a pharmaceutical composition which comprises a sPLA2 inhibitor as Active Ingredient and an effective amount of a Solubilizer acting as a chelating agent, for example, preferably at least one compound selected from citric acid, edetic acid (e.g., EDTA, disodium which also has metalloproteinase inhibiting properties), polyphosphoric acid and their salts, more preferably sodium citrate. Examples of polyphosphoric acid and their salts are potassium polyphosphate as described in the Japanese standards of food additives, 6th ed., and sodium polyphosphate as described in the Japanese standards of food additives, 6th ed., or the Japanese standards of cosmetic ingredients, 2nd ed. Sodium citrate is available as trisodium citrate anhydrous, trisodium citrate dihydrate, and trisodium citrate pentahydrate, but is most conveniently and preferably used in the form of trisodium citrate dyhydrate (mol. wt. 294.10).

The amount of the Solubilizer varies with the kind of the Solubilizer and the concentration of the inhibitor compound(s) included for example, and may be from about 1% to about 400% (w/w), preferably 1 to 200% (w/w), most preferably 1 to 100% (w/w) of the amount of the inhibitor compound. For pharmaceutical compositions using sodium citrate the weight of Solubilizer is from 10% to 60% (w/w) and most preferable 25% to 50% (w/w) of the amount of the inhibitor compound.

Preferably, the pharmaceutical composition also contains an effective amount of a Stabilizer. The Stabilizer is at least one pharmaceutically acceptable compound selected from solid sugars and sugar-alcohols more preferably at least one compound selected from mannitol, xylitol, sorbitol, glucose, fructose, lactose and maltose. Mannitol is the more preferred Stabilizer ingredient.

The amount of the Stabilizer varies with the kind of Stabilizer and the concentration of sPLA2 and/or other inhibitor included, and may be 40% to 500% (w/w), preferably from 50% to 300% (w/w), more preferably from 50 to 200% (w/w), most preferably from 100% to 200% (w/w) of the amount of the inhibitor compound(s).

Sometimes Poloxamers are nonionic triblock copolymers composed of a central hydrophobic chain of polyoxypropylene (poly(propylene oxide)) flanked by two hydrophilic chains of polyoxyethylene (poly(ethylene oxide)). Poloxamers are also known by the trade names Synperonics, Pluronics and Kolliphor, among others. Because the lengths of the polymer blocks can be customized, many different poloxamers exist that have slightly different properties. For the generic term "poloxamer", these copolymers are commonly named with the letter "P" (for poloxamer) followed by three digits: the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). Among other things, they can be used to increase the water solubility of hydrophobic, oily substances or otherwise increase the miscibility of two substances with different hydrophobicities. For this reason, these polymers are commonly used in industrial applications, cosmetics, and pharmaceuticals. They have also been evaluated for various drug delivery applications and are useful for both the delivery of varespladib-based therapies and offer certain therapeutic effects related to the prevention and treatment of coagulopathic and cytotoxic effects of venom (e.g. Poloxomer 188 and its purified derivatives usually given as an infusion). Poloxomers may be given by any route of administration: orally, ocularly, topically, rectally or intravenously increasing the versatility of small molecule anti-snake venom therapeutics (e.g. varespladib, methylvarespladib and combinations thereof with MP and SP inhibitors, antivenom itself and pharmaceutically acceptable combinations thereof) also having therapeutic effects on their own.

Without departing from the object and scope of the present invention, other pharmaceutically acceptable additive agents may optionally be added to the preparations useful for the practice of the present invention. Where a solution according to the invention is prepared for injection, and isotonizing agent, a soothing agent or other additives may be added thereto.

Preferably, the pharmaceutical compositions described above are salt-free except for the Active Ingredient, the Solubilizer and the Stabilizer.

IX. Compositions

A. Compositions

One or more compositions comprising at least one inhibitor compound selected from the group consisting of a metalloproteinase inhibitor, a $PLA_2$ inhibitor and a serine protease inhibitor and, optionally, an adjuvant therapeutic also may be (co-)administered, as described above to treat or reduce the likelihood of neurotoxin-induced respiratory failure following envenomation by venomous arthropods such as *Centuroides* spp stings (wood scorpion), cone snails and tropical jellyfish. In preferred aspects, the composition described above comprises at least one PLA2 inhibitor, preferably varespladib and/or methyl varespladib, which may be used in the absence of a serine protease inhibitor.

In some embodiments a composition comprising at least one inhibitor agent selected from the group consisting of a metalloproteinase inhibitor, a $PLA_2$ inhibitor and a serine protease inhibitor is administered directly to the bite site or damaged tissues or proximal to the bite site while another composition comprising at least one inhibitor agent selected from the group consisting of a metalloproteinase inhibitor, a $PLA_2$ inhibitor and a serine protease inhibitor is administered by another route with or without injection, and may even be administered with or after administration of antivenom as adjunct treatment or to shorten the duration of routine or intensive hospital care. In some embodiments, one or more compositions comprising at least one inhibitor agent selected from the group consisting of a metalloproteinase inhibitor, a $PLA_2$ inhibitor and a serine protease inhibitor are administered in lieu of antivenom for non-lethal or non-limb threatening injuries including, but not limited, to isolated facial paralysis or cranial nerve palsy. In preferred aspects, the composition comprises at least one $PLA_2$ inhibitor, more preferably varespladib and/or methyl varespladib.

i) Lyophilized Compositions

Preferably, the pharmaceutical compositions described in the preceding section are lyophilized. Most preferably the lyophilized composition is prepared with an annealing step by employing the collapse temperature characteristics of the compound(s) useful for the practice of the invention.

For example, the lyophilized composition contains Solubilizer from about 1 to about 200% (w/w) or more of the amount of active compound in the composition. The proportions of the Solubilizer may vary according to the active compounds and the solubilizer used. When the Solubilizer is disodium EDTA (or its acid or other salts) it is preferably used from about 1% to about 15% (w/w) of the amount of the active compound(s). The identity and proportions of Stabilizer are readily determined the skilled person. Mannitol is most often used as the Stabilizer ingredient of the lyophilized compositions of the invention.

The lyophilized pharmaceutical formulation can be dissolved in a pharmaceutically acceptable carrier, such as sterile water, sterile water optionally containing saline and/or sterile water containing sugars. For example, for intravenous or intramuscular or subcutaneous injection, the compositions of the invention may be dissolved in at a concentration of 2 mg/ml in a 4% dextrose/0.5% Na citrate aqueous solution.

Method of Making the Lyophilized Compositions Useful for the Practice of the Invention:

The lyophilized compositions useful for the practice of the present invention refer to a preparation prepared by freeze drying a solution containing a sPLA2 inhibitor compound, e.g. varespladib or methyl varespladib, optionally being subjected to a heat treating process, and being dried in a high vacuum for sublimating water. Such lyophilized preparations include lyophilized preparations for injection as mentioned above. The lyophilized preparation may be produced by conventional methods including tray lyophilization, spray lyophilization and vial lyophilization methods. Vial lyophilization is advantageous for preparing multi-dosage units of the invention.

In order to obtain a solution of an active compound by the process of the present invention, the active compound(s), a Solubilizer and a solvent are mixed and stirred until the mixture becomes clear. The solvent is preferably an aqueous solvent such as water, purified water, water for injection, isotonic sodium chloride solution or glucose injection as described in the Japanese Pharmacopoeia, more preferably a salt-free aqueous solvent such as water, purified water, water for injection or glucose solutions for injection.

Alternatively, a suitable solvent for forming a solution from the composition of the invention is any injectable solution as further exemplified by those described in The United States Pharmacopeia (1995, ISBN 0195-7996), for example, "Sterile Water for Injection", "Dextrose and Sodium Chloride Injection", "Dextrose Injection", "Mannitol Injection" or "Mannitol in Sodium Chloride Injection." These are well known in the art.

In order to obtain a lyophilized preparation of active compound for example, by the process of the present invention, first, a processing solution prior to lyophilization is prepared. The processing solution before lyophilization is a solution prepared by mixing and stirring the active compound(s), a Solubilizer and a solvent, preferably varespladib, a Solubilizer, a Stabilizer and a solvent, until the mixture becomes clear. For the sequence of addition of the ingredients to the solvent it is highly preferred to first dissolve the Solubilizer and Stabilizer, and thereafter dissolve the active compound(s). The solvent is preferably an aqueous solvent such as previously set out above and as described in the Japanese Pharmacopoeia more preferably a salt-free aqueous solvent such as water, purified water, water for injection or glucose injection. The processing solution before lyophilization of active compound for example, may contain active for example, at a concentration of from about 0.5% to 2% (w/w). If desired, the processing solution before lyophilization may be subjected to a filtration process. The filtration process includes, for example in the case of injection preparations, a sterilizing filtration and/or an ultra filtration of the processing solution before lyophilization to eliminate microorganisms or other contaminating matter from the processing solution before lyophilization.

If desired, the processing solution before lyophilization may be subjected to a distributing process. The distributing process includes, for example in the case of vial lyophilizations, a process distributing a suitable volume of the processing solution before lyophilization into vials taking the concentration of a $sPLA_2$ inhibitor compound into consideration in order that vial products carry a desired amount of sPLA2 inhibitor compounds.

A typical lyophilization process is performed as follows: Preferably, the lyophilized composition is prepared by a sequential heating and cooling process. A process for preparing a lyophilized composition comprises the sequential steps of:

(a) dissolving lyophilized composition ingredients comprising a sPLA2 inhibitor e.g. varespladib, Solubilizer, and Stabilizer in an aqueous solvent;

(b) cooling the processing solution of step (a) to a temperature below −33° C.;

(c) heating the product of step (b) to a temperature above −33° C.;

(d) cooling the product of step (c) to a temperature below −33° C.;

(e) heating the product of step (d) to a temperature above −13° C., under subatmospheric pressure for a time sufficient to remove water from the aqueous solvent and yield a solid lyophilized product.

Preferably, step (a) is conducted by dissolving in an aqueous solvent: an sPLA2 inhibitor and/or other actives; Solubilizer selected from citric acid, edetic acid, polyphosphoric acid and their salts, the amount of which is 1 to 100% (w/w) of the amount of the equivalent acid of active agent; and Stabilizer selected from mannitol, xylitol, sorbitol, glucose, fructose, lactose and maltose, the amount of which is about 50 to 200% (w/w) of the equivalent amount of active compound. Moreover, each of steps (b), (c), (d) and (e) is preferably conducted for a period of at least one-half hour, and step (e) is performed at a subatmospheric pressure less than 133 Pa (1000 milliTorr). Preferred parameters in the lyophilization process are those wherein Compound (Vb) for example, is frozen by cooling to −35° C. to −45° C. This cooling step is performed preferably over 2 to 4 hours. This process is herein after referred to as the "primary freezing process". If desired, the frozen solution obtained in the primary freezing process is then warmed to −5° C. to −25° C. preferably from −10° C. to −20° C. This warming step is performed over 3 hours, preferably from 5 to 10 hours. This process is referred to as the "heat treating process".

The composition obtained in the heat treating process is re-frozen, preferably from about −35° C. to −45° C. This cooling step is performed preferably over 2 to 4 hours. This process is referred to as the "re-freezing process".

The composition obtained through the primary freezing process, the heat treating process and the re-freezing process, is dried under a high vacuum by sublimating water according to methods known to those skilled in the art. Thus, a lyophilized preparation of the present invention is obtained. If desired, two step drying in which the temperature and the degree of vacuum are different may be performed for completely removing water. This process is herein after referred to as the "drying process". If the two step drying is performed, these processes are referred to as the "primary drying" process and the "secondary drying" process. The lyophilization process removes most of the water originally present, but the final product lyophilized composition may contain some free water. Typically, the water content can range from 0.5% to 5.0% weight percent. More typically, the water content ranges from 0.8% to 2.0%. Once prepared, the lyophilization powder may be used to prepare saline solutions and formulated for injection via needle or propulsion without a needle (e.g. jet injector).

Inhalation therapy also may be useful either alone or as an adjunct to other routes of administration. With inhalation therapy, doses necessary to produce a decrease in the clinical symptoms of envenomation are readily determined and used.

Pharmaceutical compositions according to the present invention typically include a conventional pharmaceutical carrier or excipient and may additionally include other medicinal agents, carriers, adjuvants, additives and the like. Preferably, the composition is about 0.1% to about 95%, about 0.25% to about 85%, about 0.5% to about 75%, about 0.1% to about 10% by weight of a compound or compounds of the invention, with the remainder consisting essentially of suitable pharmaceutical excipients.

In certain embodiments, pharmaceutical formulations of the invention are administered as a liquid, a solid, a semi-solid or lyophilized powder form (e.g. formulated into solutions and injected), an immediate or sustained-release formulation, a tablet, a capsule, a powder, a suppository, a cream, an ointment, a lotion, an aerosols, a patch or the like, preferably in unit dosage forms suitable for simple administration of precise dosages. In the immediate stage of therapy, in order to provide a rapid increase in serum concentration of active, a composition in parenteral dosage form (preferably, by intramuscular injection in immediate release form), is preferably used. Thereafter, in order to maintain active at effective levels in the serum, compositions may be administered by alternative routes of administration for the maintenance doses.

In certain embodiments, pharmaceutical formulations of the invention are administered using an oil-in-water emulsion, microemulsion or nanoemulsion, a water-in-oil emulsion, microemulsion or nanoemulsion, a water-in-silicone emulsion, microemulsion or nanoemulsion, a liquid, a gel, an oil, a paste, a cream, a lotion, an ointment, a suspension, a foam, a spray or a serum carrier, a suspension, a liposome-containing formulation, a transfersome, an elastic (deformable) vesicle, an ethosome, an invasome or a penetration-enhancer-containing vesicle, a lacquer, or the formulations can comprise a component of a patch, bandage, or occlusive dressing, or other passive or active system for absorption through the skin or mucosal surface.

Passive or active systems for absorption through the skin or mucosal surface may include "skin penetration enhancers" such as alkyl (N,N-disubstituted amino alkanoate) esters, such as dodecyl 2-(N,N-dimethylamino) propionate (DDAIP), a water-dispersible acid polymer, such as a polyacrylic acid polymer, a carbomer (e.g., Carbopol® or Carbopol 940P® (B. F. Goodrich Co. Akron, Ohio)), copolymers of polyacrylic acid (e.g., Pemulen® (B. F. Goodrich Co.) or Polycarbophil® (A. H. Robbins, Richmond, Va.).; a polysaccharide gum (e.g. agar gum, alginate, carrageenan gum, ghatti gum, karaya gum, kadaya gum, rhamsan gum, xanthan gum, and galactomannan gum (e.g., guar gum, carob gum, and locust bean gum)), cellulose derivatives (e.g. ethyl cellulose, methyl cellulose, hydroxypropyl cellulose), dimethyl sulfoxide (DMSO) and dimethyl acetamide (DMA), 2-pyrrolidone, N,N-diethyl-m-toluamide (DEET), 1-dodecylazacycloheptane-2-one (Azone® Nelson Research), N,N-dimethylformamide, N-methyl-2-pyrrolidone, calcium thioglycolate, dioxolanes, cyclic ketones, alkyl N,N-2-(disubstituted amino) alkanoates including tetradecyl (N,N-dimethylamino) acetate, dodecyl (N,N-dimethylamino) acetate, decyl (N,N-dimethylamino) acetate, octyl (N,N-dimethylamino) acetate, and dodecyl (N,N-diethylamino) acetate. One group of preferred skin penetration enhancers includes isopropyl myristate, isopropyl palmitate, dimethyl sulfoxide, decyl methyl sulfoxide, dimethylalanine amide of a medium chain fatty acid, dodecyl 2-(N, N-dimethylamino) propionate and salts, thereof (e.g., hydrochloric, hydrobromic, sulfuric, phosphoric, and nitric acid addition salts) and inorganic salts (e.g., acetic, benzoic, salicylic, glycolic, succinic, nicotinic, tartaric, maleic, malic, pamoic, methanesulfonic, cyclohexanesulfamic, picric, and lactic acid addition salts).

In some embodiments, a pharmaceutical composition of the invention is administered by a patch which comprises an active-ingredient containing adhesive matrix disposed between an impermeable backing layer and a removable film layer. See e.g. U.S. Patent Application Document Nos. 20140322284 and 20140335150.

Composition for Parenteral Administration

An injectable composition for parenteral administration (e.g. intravenous, intramuscular, subcutaneous or intrathecal) will typically contain the compound in a suitable standard intravenous solution, such as sterile physiological salt solution. The composition may also be formulated as a suspension in an aqueous emulsion. The compositions may be provided as final compositions loaded into syringes or injection devices for immediate administration, or alternatively, may be provided as lyophilized or other powders that are mixed with solution (e.g., saline or other solution) temporal to the envenomation and administered.

Injectable formulations may be administered subcutaneously, intracutaneously, intravenously, intramuscularly, intra-articularly, intrasynovially, intrasternally, intrathecally, intralesionally, intracranially or via infusion. Excipients for injectable solutions include, but are not limited to, buffers (e.g. citrate/citric acid), acidifying agents (e.g. hydrochloric acid), alkalizing agents (e.g. sodium hydroxide), preservatives (e.g. phenol), co-solvents (e.g. polyethylene glycol 400), tonicity adjusters (e.g. mannitol), stabilizers (e.g. surfactant, antioxidants, amino acids). Active ingredients may be administered in single or multiple dose injectable form, e.g. in the form of a pen. Pharmaceutical compositions may be provided together with a device for application, for example together with a syringe, an injection pen or an autoinjector. Such devices may be provided separate from a pharmaceutical composition or prefilled with the pharmaceutical composition. Examples of injection devices include intramuscular devices such as EpiPen® Auto-Injector—Dey Pharma, DuoDote® Auto-Injector—Meridian Medical technologies corp, EVZIO® Auto-Injector—kaleo, Inc., subcutaneous devices such as Rasuvo—Medac (subcutaneous), Otrexup—Antares Pharma Inc., Imitrex STATdose SYSTEM® and STATdose—GlaxoSmithKline, Mini-Ject™—Valeritas, Inc., Uniject®—Becton Dickinson, and jet injectors such as Vitajet3—Bioject and Penjet—Penjet corporation, among numerous others.

Liquid compositions can be prepared by dissolving or dispersing the active ingredient(s) (about 0.5% to about 20% by weight or more), and optional pharmaceutical adjuvants, in a carrier, such as, for example, aqueous saline, aqueous dextrose, glycerol, or ethanol, to form a solution or suspension. For use in an oral liquid preparation, the composition may be prepared as a solution, suspension, emulsion, or syrup, being supplied either in liquid form or a dried form suitable for hydration in water or normal saline.

Ii) Oral Administration Forms

For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations and additives to formulate extended release preparations.

Mucosal Adsorption Enhancer

Injectable, aerosolized and intranasal formulations may contain a mucosal adsorption enhancer such as DMSO, citric acid, sodium citrate, propylene glycol, glycerin, L-ascorbic acid, sodium metabisulfite, edetate disodium, benzalkonium chloride, sodium hydroxide, dimethylformamide, ethanol, propylene glycol, 1,3 butanediol, 2-pyrrolidones and mixtures thereof. Other mucosal adsorption enhancers are known in the art, including Copackaging In one aspect kits are provided for treatment of envenomation. Kits of the invention may comprise a PLA2 inhibitor along with one of more of a MP inhibitor, a SP inhibitor, and an antivenom. In kits multiple agents may be contained in separate containers which are packaged together.

EXEMPLARY EMBODIMENTS

In preferred aspects the invention utilizes an effective amount of $PLA_2$ inhibitor (preferably, the 1H-Indole-3-glyoxylamides, especially varespladib, methylvarespladib or mixtures thereof) as the sole agent or agents to treat the subject suffering from an envenomation. It has unexpectedly been discovered that both varespladib and methylvarespladib exhibit potent PLA2 inhibition as well as, at times, metalloproteinase and/or serine protease inhibition and may be used alone or in combination to great effect as agents to treat envenomation. In alternative embodiments, the invention may additionally comprise effective amounts of one or more additional agents including one or more additional $PLA_2$ inhibitors (as otherwise described herein, often camostate or gabexate, when used), one or more acetylcholinesterase inhibitors (for example, preferably neostigmine or pyridostigmine and/or atropine or glycopyrrolate), one or more metalloproteinase inhibitors (e.g. prinomastat, marimastat, vorinostat or batimastat), one or more serine protease inhibitors (e.g. nafamostat, camostat or gabexate), at least one spreading factor inhibitor and at least one NMDA receptor antagonist, among others, including lidocaine and/or bupivacaine which may be included in effective amounts in order to increase blood flow in the area while providing pain relief in which the composition is administered in order to increase biodistribution to the active site of the agent(s). In certain preferred embodiments, a small molecule inhibitor such as Varespladib and/or Methyvarespladib is combined with antivenom to produce an unexpectedly potent treatment for envenomation.

The invention provides methods of treatment, pharmaceutical compositions, systems and kits which use at least one active component, in some instances at least two active components and in other Instances no more than two active components selected from the group consisting of a selective secretory $PLA_2$ inhibitor (sPLA2 or $PLA_2$ inhibitor which also may function as an effective metalloproteinase inhibitor), a metalloproteinase inhibitor, a serine protease inhibitor, one or more acetylcholinesterase inhibitors, a NMDA receptor antagonist, an L-aminooxidase inhibitor, a hyaluronidase inhibitor and a a spreading factor inhibitor to treat a subject who suffers from an envenomation. Initial administration may be at the time of envenomation and often within a period of several hours (1 minute to 12 hours) to less than about an hour after an envenomation, sometimes no more than about 1 to about 20 minutes, sometimes about 1 to about 10 minutes, after an envenomation by, for example, a snake or invertebrate. In other embodiments, especially when one or more of the above-described compounds (preferably, small molecules) is combined with antivenom, these compositions may be administered a number of hours after envenomentation before or after receiving antivenom but preferably before, for example, as a first line treatment for snakebite in a hospital or other patient care facility. In some embodiment, or in addition, sequential dosing of PLA2ls may be used. In preferred aspects the invention utilizes an effective amount of $PLA_2$ inhibitor (preferably, the 1H-Indole-3-glyoxylamides, especially varespladib, methylvarespladib or mixtures thereof) as the sole agent or agents to treat the subject suffering from an envenomation.

1. It has unexpectedly been discovered that both varespladib and, most notably methylvarespladib exhibit potent snake venom PLA2 inhibition, but NOT highly potent bee venom PLA2 inhibition as well as serine protease and metalloproteinase inhibition in some cases and so may be used alone or in combination to great effect as agents to treat envenomation. In alternative embodiments, the invention may additionally comprise effective amounts of one or more additional agents including one or more additional $PLA_2$ inhibitors (as otherwise described herein, often indoxam or methyindoxam) an SP inhibitor that might lower serum PLA2 activity levels camostate or gabexate, when used), one or more acetylcholinesterase inhibitors (for example, preferably neostigmine, edrophonium or pyridostimine with atropine or glycopyrrolate), one or more metalloproteinase inhibitors (e.g. marimastat, prinomastat, tanomastat, vorinostat, batimastat, ilomastat and antibiotics such as doxycycline, cefixime and other cephalosporins), one or more serine protease inhibitors (e.g. nafamostat, which also has metalloproteinase inhibitory effects in some venoms, gabexate and camostat or camostate), at least one spreading factor inhibitor and at least one NMDA receptor antagonist, among others and including lidocaine and/or bupivacaine which may be included in effective amounts in order to increase blood flow in the area in which the composition is administered in order to increase biodistribution to the active site of the agent(s). Unexpectedly, alone or in combination with antivenom, varespladib was discovered to have IC50s specific for snake venoms lower than any ever reported for any snake venom or human sPLA2 isoform—as low as 0.05 nM when combined with antivenom with reported low ranges usually between 3 and 9 nM for varespladib, indoxam and related compounds (Dennis, Edward A., et al. "Phospholipase A2 enzymes: physical structure, biological function, disease implication, chemical inhibition, and therapeutic intervention." *Chemical reviews* 111.10 (2011): 6130-6185).

In one preferred embodiment, at least one agent selected from the group consisting of a 1H-Indole-3-glyoxylamide compound, especially varespladib and/or methylvarespladib, and optionally camostat (N,N-dimethylcarbamoylmethyl,4-4-guanidinobenzoyloxy-phenylacetate or camostate) and/or gabexate (ethyl-p[6-guanidinohexanoyloxy]-benzoate methansulfonate), preferably at least varespladib, is co-administered with an acetylcholinesterase inhibitor (AChI) (e.g. neostigmine, edrophonium, or pyridostigmine, each preferably with atropine or glycopyrrolate) to provide a particularly effective universal antiparalytic whose significant anti-hemotoxic activity is conferred by varespladib and/or methylvarespladib, camostat and/or gabexate. In certain preferred embodiments, the composition to be administered contains an effective amount of at least versapladib or methylvarespladib which is metabolized into varespladib as its prodrug in mammals.

In another embodiment, varespladib and/or methylvarespladib, optionally in combination with one or more additional $PLA_2$ inhibitors, but preferably at least varespladib, is co-administered with at least one metalloproteinase inhibitor (e.g. prinomastat, marimastat or batimastat, preferably prinomastat) and/or at least one acetylcholinesterase inhibitor (AChEI) (e.g. neostgmine and/or atropine). In certain additional preferred embodiments, both one or more metalloproteinase inhibitors and one or more acetylcholinesterase inhibitors is included with the varespladib and/or methylvarespladib to reduce the likelihood that an envenomated subject will die or be permanently debilitated from bleeding, clotting or paralysis induced by the envenomation.

Notably, methods of treatment, pharmaceutical compositions, systems and kits of the invention obviate the need for antivenom in treating envenomated subjects, at least in the initial stages (e.g. from immediately after the bite until up to about 24 hours or more after bite) to allow the envenomated subject to travel to a hospital or other patient care facility for further diagnosis and/or treatment with an anti-venom agent or anti-venom-small molecule combination (often varespladib/methyl varespladib). The antivenom agents and the anti-venom small molecule(s) combination may be administered in combination with MMP inhibitors such as doxycycline, cefixime or prinomastat. Quite unexpectedly varespladib and/or methylvarespladib alone are quite effective in inhibiting the effects of envenmomentation by a large number of venomous animals, including snakes and likely other reptiles (e.g. lizards), amphibians (poisonous frogs), scorpions, spiders, insects, cnidarian (a.k.a. "coelenterates" and including poisonous jellyfish and corals) and the like. Quite unexpectedly, a combination of varespladib and/or methylvarespladib without and with certain metalloproteinase inhibitors likely prove effective in the treatment of bites for every major venomous snake in Japan. Further, co-administration of varespladib and/or methylvarespladib with or without neostigmine or pyridostigmine and optionally atropine or glycopyrrolate will treat effectively bites of every coral snake found in the Americas, a discovery with profound therapeutic implications as it enables immediate treatment of life-threatening symptoms, especially through self-administration of therapeutics by a victim at the time of envenomation. In other embodiments, the inclusion of varespladib and/or methylvarespladib and optionally another $PLA_2$ inhibitor (e.g. indoxam or methylindoxam among other direct or indirect inhibitors—eg gabexate), and one or more of prinomastat, chemostat, batimastat and marimastat and an acetylcholinesterase inhibitor (e.g. neostigmine and/or atropine) will provide a composition which is particularly useful in treating envenomated subjects in areas where venomous animals produce effects through impact on bleeding/coagulation and paralysis.

Quite unexpectedly, varespladib and methylvarespladib alone inhibit the activities of a wide variety of venom components suggesting either or both a direct regulatory role for PLA2 in the activity of many enzymatic and non-enzymatic venom components as well as host-mediated responses that facilitate entry of non-enzymatic, tissue destroying toxins into host cells if not by direct inhibition of the non-PLA2 snake venom enzymes heretofore undescribed in the scientific literature. Furthermore, varespladib and methyl varespladib have anti-inflammatory activity decreasing vascular permeability and decreasing the ability of venom to spread while small molecule therapeutics can diffuse to the site of venom deposition. This surprising combination of salutary effects (direct inhibition of the venom by varespladib and its prodrug, methylvarespladib) make it an ideal candidate for a multifunctional antidote to snakebite alone or in combination with other small molecule therapeutics and/or antivenom.

Significantly, unlike antivenom, compositions of the present invention can diffuse or penetrate nervous system tissues, blood clots and/or dead tissue found at envenomation sites, thus providing effective therapy where antivenom exhibits reduced or negligible impact. The inclusion of lidocaine and/or bupivacaine may assist in having the agent, once administered more quickly reach its site of activity while potentially providing pain relief from the bite and prevention of pain from delivery of the drugs when any parenteral mechanism is used and for general analgesia.

Methods of treatment, pharmaceutical compositions, systems and kits of the invention may be used to treat not only humans, but also in veterinary applications such as the treatment of livestock, horses or companion animals as otherwise described herein.

The invention provides methods of treatment, pharmaceutical compositions, systems and kits which use at least one active component, in some instances at least two active components and in other instances no more than two active components selected from the group consisting of a selective secretory $PLA_2$ inhibitor (sPLA2 or $PLA_2$ inhibitor), a metalloproteinase inhibitor, a serine protease inhibitor, one or more acetylcholinesterase inhibitors or a nAChR agonist paired with a mAChR antagonist, a NMDA receptor antagonist and a spreading factor inhibitor to treat a subject who suffers from an envenomation, preferably at the time of envenomation and often within a period of less than about an hour after an envenomation, more no more than about 1 to about 20 minutes, more often about 1 to about 10 minutes, after an envenomation by, for example, a snake or invertebrate. In preferred aspects the invention utilizes an effective amount of $PLA_2$ inhibitor (preferably, the 1H-Indole-3-glyoxylamides, especially varespladib, methylvarespladib or mixtures thereof) as the sole agent or agents to treat the subject suffering from an envenomation. It has unexpectedly been discovered that both varespladib and methylvarespladib exhibit potent PLA2 inhibition as well as, at times, metalloproteinase and/or serine protease inhibition and may be used alone or in combination to great effect as agents to treat envenomation. In alternative embodiments, the invention may additionally comprise effective amounts of one or more additional agents including one or more additional $PLA_2$ inhibitors (as otherwise described herein, often camostate or gabexate, when used), one or more acetylcholinesterase inhibitors (for example, preferably neostigmine and/or atropine), one or more metalloproteinase inhibitors (e.g. marimastat, nafamostat or prinomastat), one or more serine protease inhibitors (e.g. nafamostat), at least one spreading factor inhibitor and at least one NMDA receptor antagonist, among others, including lidocaine and/or bupivacaine which may be included in effective amounts in order to increase blood flow in the area while providing pain relief in which the composition is administered in order to increase biodistribution to the active site of the agent(s). In certain preferred embodiments, a small molecule inhibitor such as Varespladib and/or Methyvarespladib is combined with antivenom to produce an unexpected potent treatment for envenomation.

The invention provides methods of treatment, pharmaceutical compositions, systems and kits which use at least one active component, in some instances at least two active components and in other instances no more than two active components selected from the group consisting of a selective secretory $PLA_2$ inhibitor that also may function as an effective metalloproteinase inhibitor), a metalloproteinase inhibitor, a serine protease inhibitor, one or more acetylcholinesterase inhibitors, a NMDA receptor antagonist, an L-aminooxidase inhibitor, a hyaluronidase inhibitor and a a spreading factor inhibitor to treat a subject who suffers from an envenomation, preferably at the time of envenomation and often within a period of several hours to less than about an hour after an envenomation, more often no more than about 1 to about 20 minutes, more often about 1 to about 10 minutes, after a bite or sting by, for example, a snake or invertebrate. In other embodiments, especially when one or more of the above-described compounds (preferably, small molecules) is combined with antivenom, these compositions may be administered a number of hours after envenomentation, for example, as a first line treatment for snake bite in a hospital or other patient care facility.

It has unexpectedly been discovered that both varespladib and, most notably methylvarespladib exhibit potent snake venom PLA2 inhibition, but not as potent bee venom PLA2 inhibition as well as serine protease and metalloproteinase inhibition in some cases and so may be used alone or in combination to great effect as agents to treat envenomation. In alternative embodiments, the invention may additionally comprise effective amounts of one or more additional agents including one or more additional $PLA_2$ inhibitors (as otherwise described herein, often camostate or gabexate, when used), one or more acetylcholinesterase inhibitors (for example, preferably neostigmine, edrophonium or pyridostimine with atropine or glycopyrrolate), one or more metalloproteinase inhibitors (e.g. marimastat, prinomastat, tanomastat, nafamostat, batimastat and antibiotics such as doxycycline, cefixime and other cephalosporins, one or more serine protease inhibitors (e.g. nafamostat, which also has metalloproteinase inhibitory effects in some venoms), at least one spreading factor inhibitor and at least one NMDA receptor antagonist, among others and including lidocaine and/or bupivacaine which may be included in effective amounts in order to increase blood flow in the area in which the composition is administered in order to increase biodistribution to the active site of the agent(s). Unexpectedly, alone or in combination with antivenom, varespladib was discovered to have IC50s specific for snake venoms lower than any ever reported for any snake venom sPLA2 human isoform—as low as 0.05 nM when combined with antivenom (compared to ranges 3-9 nM).

In one preferred embodiment, at least one agent selected from the group consisting of a 1H-Indole-3-glyoxylamide compound, especially varespladib and/or methylvarespladib, and optionally an SP inhibitor such as camostat (N,N-dimethylcarbamoylmethyl,4-4-guanidinobenzoyloxy-phenylacetate or camostate) and/or gabexate (ethyl-p[6-guanidinohexanoyloxy]-benzoate methansulfonate), preferably at least varespladib, is co-administered with an acetylcholinesterase inhibitor (AChI) (e.g. neostigmine, edrophonium, or pyridostigmine, each preferably with atropine or glycopyrrolate) to provide a particularly effective universal antiparalytic whose significant anti-hemotoxic activity is conferred by varespladib and/or methylvarespladib, camostat and/or gabexate. In certain preferred embodiments, the composition to be administered contains an effective amount of at least versapladib or methyl varespladib which is metabolized into varespladib as its prodrug in mammals.

In another embodiment, varespladib and/or methylvarespladib, optionally in combination with one or more additional $PLA_2$ inhibitors, but preferably at least varespladib, is co-administered with at least one metalloproteinase inhibitor (e.g. prinomastat, marimastat or batimastat, preferably prinomastat) and/or at least one acetylcholinesterase inhibitor (AChEI) (e.g. neostgmine and/or atropine). In certain additional preferred embodiments, both one or more metalloproteinase inhibitors and one or more acetylcholinesterase inhibitors is included with the varespladib and/or methyl-varespladib to reduce the likelihood that an envenomated subject will die or be permanently debilitated from bleeding, clotting or paralysis induced by the envenomation.

Notably, methods of treatment, pharmaceutical compositions, systems and kits of the invention obviate the need for antivenom in treating envenomated subjects, at least in the initial stages (e.g. from immediately after the bite until up to about 24 hours or more after bite) to allow the envenomated subject to travel to a hospital or other patient care facility for further diagnosis and/or treatment with an anti-venom agent or anti-venom small molecule combination (often varespladib/methylvarespladib). The anti-venom agents and the antidote small molecule(s) combination may be administered in combination with MP inhibitors such as doxycycline or marimastat. Quite unexpectedly varespladib and/or methylvarespladib alone are quite effective in inhibiting the effects of envenmomentation by a large number of venomous animals, including snakes and likely other reptiles (e.g. lizards), amphibians (poisonous frogs), scorpions, spiders, insects, coelenterates (poisonous jelly fish) and the like. Quite unexpectedly, a combination of varespladib and/or methylvarespladib without and with certain metalloproteinase inhibitors likely prove effective in the treatment of bites for every major venomous snake in Japan. Further, co-administration of varespladib and/or methylvarespladib with or without neostigmine or pyridostigmine and optionally atropine or glycopyrrolate will treat effectively bites of every coral snake found in the Americas, a discovery with profound therapeutic implications as it enables immediate treatment of life-threatening symptoms, especially through self-administration of therapeutics by a victim at the time of envenomation. In other embodiments, the inclusion of varespladib and/or methylvarespladib and optionally another $PLA_2$ inhibitor (e.g. camostate and/or gabexate, among others), and one or more of prinomastat, chemostat, batimastat and marimastat and an acetylcholinesterase inhibitor (e.g. neostigmine and/or atropine) will provide a composition which is particularly useful in treating envenomated subjects in areas where venomous animals produce effects through impact on bleeding/coagulation and paralysis.

Unexpectedly, varespladib and methyl varespladib alone inhibit the activities of a wide variety of venom components suggesting either or both a direct regulatory role for PLA2 in the activity of many enzymatic and non-enzymatic venom components as well as host-mediated responses that facilitate entry of non-enzymatic, tissue destroying toxins into host cells if not by direct inhibition of the non-PLA2 snake venom enzymes heretofore undescribed in the scientific literature. Furthermore, varespladib and methyl varespladib have anti-inflammatory activity decreasing vascular permeability and decreasing the ability of venom to spread while small molecule therapeutics can diffuse to the site of venom deposition. This surprising combination of salutary effects (direct inhibition of the venom by varespladib and its prodrug, methyl varespladib) make it an ideal candidate for a multifunctional antidote to snakebite alone or in combination with other therapeutics and/or antivenom.

Significantly, unlike antivenom, compositions of the present invention can diffuse or penetrate nervous system tissues, blood clots and/or dead tissue found at envenomation sites, thus providing effective therapy where antivenom exhibits reduced or negligible impact. The inclusion of lidocaine and/or bupivacaine may assist in having the agent, once administered more quickly reach its site of activity while potentially providing pain relief from the bite and prevention of pain from delivery of the drugs when any parenteral mechanism is used and for general analgesia.

Methods of treatment, pharmaceutical compositions, systems and kits of the invention may be used to treat not only humans, but also in veterinary applications such as the treatment of livestock or companion animals as otherwise described herein.

The invention is illustrated further in the following non-limiting examples.

Example 1

In Vitro Experiments

Overview: Initial experiments were performed to assess sPLA2 activity using the 1,2-dithio analog of diheptanoyl phosphatidylcholine and were not optimized, but yielded surprisingly robust results confirming the present inventor's idea of testing varespladib and methyl-varespladib in greater detail. Background. Phospholipase A2 (PLA2) catalyzes the hydrolysis of phospholipids at the sn-2 position yielding a free fatty acid and a lysophospholipid. The release of arachidonic acid from membrane phospholipids by PLA is believed to be a key step in the control of eicosanoid production within the cell. The Bee Venom PLA2 Control was a 100 μg/ml solution of bee venom PLA2 is supplied as a positive control in the kit (Abcam kit catalog number ab133089). Substrate for MP was DQ Gelatin and assay run per EnzChek gelatinase assay manufacturers instructions. Venom MP activity was not optimized in initial experiments, but reaction rates were during experiments performed by an independently contracted laboratory. SP assay was performed using Nα-Benzoyl-L-arginine-7-amido-4-methylcoumarin hydrochloride. These kits were stored as specified if stored at −20° C. Unless otherwise specified, in the case of my experiments, only crude, unfractionated lyophilized venom purchased from Sigma or the Miami Serpentarium were used. Plate Setup: Manufacturers guidelines (paraphrased herein) were followed unless otherwise specified. Data Analysis: xcel per manufacturers recommendations. MP and SP assays were prepared and plated in the same manner as PLA2 assays except substrates and fluorophores were different. PBS was the buffer in the case of MP and SP assays and absorbance measured at 495 nm. Substrate for MP was DQ Gelatin and assay run per EnzChek gelatinase assay manufacturers instructions except that experiments were run, unconventionally at 37 C to estimate human body temperature and initial experiments for PLA2, MP activity and SP activity were not optimized for screening (e.g. extremely high doses of venom were used—10 mg/mL stock in all cases since the quality of the venom was unknown with final concentration of 0.444 mg/mL in the test wells). SP assay was performed using Na-Benzoyl-L-arginine-7-amido-4-methylcoumarin hydrochloride (Sigma). Specifics of contract laboratory technique vary from the present inventor's initial experiments in terms of venom and substrate optimization, plate size (384 instead of 96), volume and temperature and other factors including different operators such as those described immediately below, performed following the first pilot experiments and subsequently extended by a contract laboratory.

Example 2

Small Molecule Screening and Dose-Response Experiments

Small molecule screening and dose-response experiments took place in the Yale Center for Molecular Discovery. Instrumentation used when indicated included Tecan EVO (2), Tecan Aquarius, Matrix PlateMatePlus (2), Matrix PlateMate2×2 liquid transfer robots and Titertek and Thermo Multidrop liquid dispensers (7). PerkinElmer EnVision (3) and Tecan infinite M1000 (2) plate readers sensitively measure absorbance, fluorescence, fluorescence polarization and luminescence in 96- and 384-well plate formats. A GE InCell Analyzer 2200 imaging system acquires multicolor fluorescent and transmitted light images from plates. Piloting collections used in the first phases of screening were selected by the inventor or from libraries of known compounds and natural products available at the time of experiments on selected venoms including: NCC, GenPlus, Pharmakon, Bioactive lipids, Protease Inhibitors, Procured Drugs and FDA Approved Drugs libraries. The GenPlus (the NINDS Custom Collection) from MicroSource Discovery Systems contains 960 compounds. This unique selection of known bioactive compounds permits the simultaneous evaluation of hundreds of marketed drugs and biochemical standards. The Pharmakon 1600 collection (MicroSource) includes known drugs used globally or studied in clinical trials. An Enzo 640 compound set of FDA-approved drugs has bioactivity, safety and bioavailability known for each representative.

Each assay was characterized in similar fashion, using methodology well-established in the Center. Assays are typically performed in 384-well microtiter plates. As standard procedure, three sample populations are added to each plate; two control populations (32 wells per control in a 384-well plate) and a test population (320 wells) that will receive compounds. Positive control (c+) wells will be treated to simulate the result from an active small molecule. Negative control (c−) wells receive DMSO vehicle (in which compounds are administered). Signals from replicate positive and negative control wells are used to assess assay performance, specifically its sensitivity and reproducibility, and suitability for HIS. A statistical value, the Z' factor, mathematically represents the separation of signals between the two control populations, and an assay's ability to discriminate active compounds with high probability from inactive compounds (J-H Zhang, T D Y Chung, K R Oldenburg, (1999), A simple statistical parameter for use in evaluation and validation of high throughput screening assays, *J Biomol. Screen,* 4, 67-73). The Z' factor was calculated from the positive and negative control mean signals and their standard deviations for each plate using the formula $Z'=1-[3(\sigma_{c+}+\sigma_{c-})/|\mu_{c+}-\mu_{c-}|]$. A robust assay for screening single compounds has Z'-factors greater than 0.5 consistently. Typically, HTS assays with a high discriminatory power also have signal-to-background ratios (mean signals of positive controls divided by negative controls) greater than five, and coefficients of variation (mean-adjusted standard deviations) for positive and negative controls below 15% (Y Sui, Z Qu, (2007), Alternative statistical parameter for high-throughput screening assay quality assessment, *J Biomol Screen,* 12, 229-34).

In each case, a number of general experimental parameters was empirically evaluated, including plate type, reagent dilutions, aliquoting protocols, reference standards, spectroscopic filter sets, detection parameters, and dimethylsulfoxide (DMSO) sensitivity. In the generic protocol, reagents are added sequentially to achieve total well volumes of 20 μL in 384-well plates using the Aquarius (Tecan) or PlateMatePlus (Matrix) liquid handing robots or a Multidrop (TiterTek or Thermo). Compounds from the chemical libraries were added to a final concentration of approximately 10 μM/well using a 384-head pin tool with quills (V&P Scientific, Inc.) on the Aquarius or PlateMatePlus. Signals are quantified on platereaders or the imaging system with integrated image analysis algorithms or CellProfiler scripts. Primary screening data is analyzed using a commercial software and database package, ActvityBase (IDBS), to monitor assay performance and determine thresholds based on assay signals to identify compounds that display significant activity to warrant further characterization. After evaluation by the medicinal chemists, hit compounds can be arrayed into plates in any number of formats for confirmation, artifact detection, testing in mammalian cell lines or dose-response testing. As indicated, data were plotted and fit to models such that IC50 or EC50 values.

Example 3 sPLA2 Activity Assays

Screening was carried out for inhibitors of venom sPLA2, MP and SPs. Stock solutions of venom at 10 mg/mL were used without typical dilution for assaying various inhibitors of sPLA2, MP and SPs. The final venom concentration in the assays was very high at 0.444 mg/mL. Unexpectedly, despite substrate overconsumption in the control wells, several inhibitors exhibited significant ability to inhibit the consumption of substrate. Most notable among these were varespladib and methyl varespladib showing effects even in the presence of venom concentrations more than 100,000 times the optimized concentrations (see e.g. FIG. 4 venom concentrations for comparison using same kits and methods). A further unexpected observation with review of the data from the three assays run against venom stock solutions was that, for ceveral venoms, varespladib and methyl varespladib showed inhibition of MP and SP in several instances suggesting it could be a highly valuable multifunctional antidote and the core element of a wide array of snake and invertebrate venom antidotes.

FIG. 1 shows a time course of snake venom PLA2 activity in the presence of varespladib (100 uM) or methyl varespladib (100 uM). Despite use of an excess of venom (0.444 mg/mL final concentration), varespladib inhibited PLA2 activity in all snake venoms tested and very surprisingly so did its prodrug, methyl-varespladib in several instances (most notably *Echis carinatus*). Arrow points to varespladib and downward triangle denotes instances where the prodrug, methylvarespladib ('Met-Varespladib'), showed significant and surprising inhibition of snake venom PLA2.

Example 4

MP Activity Assays

Figure 2A:
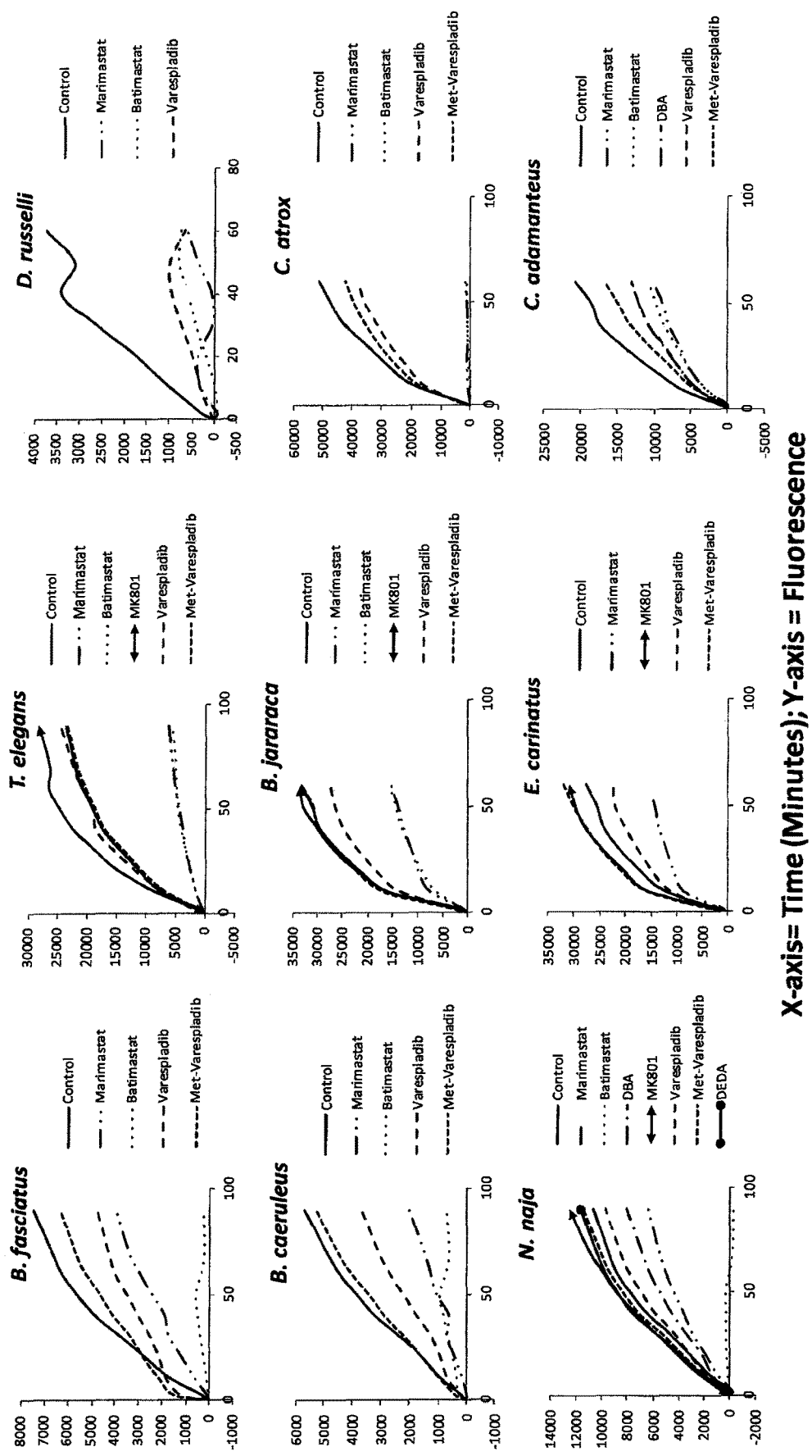
FIGS. 2A & B shows a time course of metalloproteinase activity when an extremely high concentration of venom is combined with test agents (Example 4).
Figure 2B:
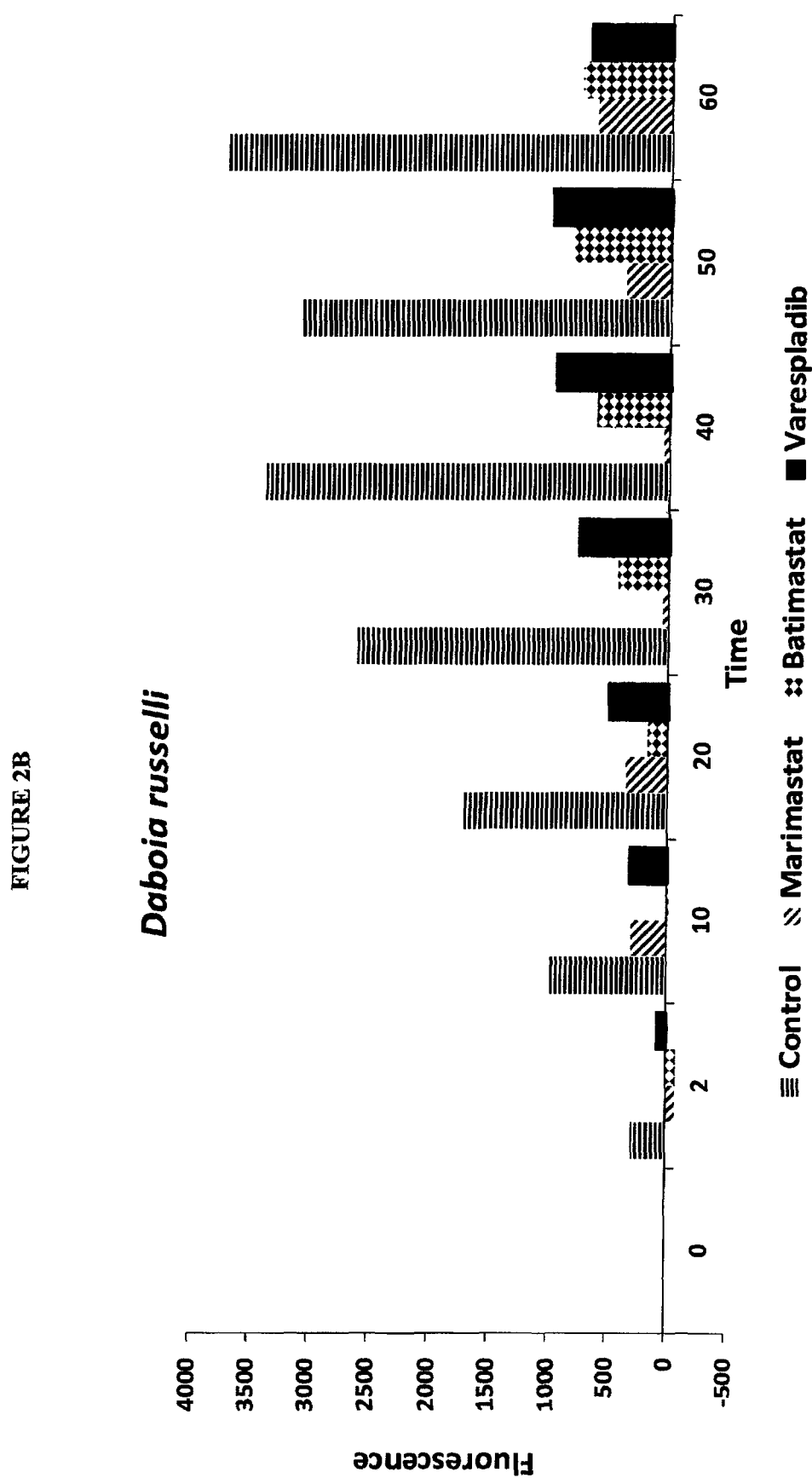

FIGS. 2A-2B show the inhibition of metalloproteinase activity when venom (0.444 mg/mL) is combined with inhibitors. FIG. 2A shows the effects of shows a time course of metalloproteinase activity when venom (0.444 mg/mL) is combined with inhibitors (100 uM). MP inhibitors batimastat and marimastat most consistently showing significant inhibition of venoms tested. NAC, DEDA and DBA also showed varying levels of MP inhibition. Unexpectedly, varespladib showed inhibition of MP activity in several snake venoms, most notably, Russell's viper. FIG. 2B The histogram shows that over time (x-axis) marimastat, batimastat and varespladib showed comparable inhibition of *Daboia russelli* venom at 100 uM.

To the inventor's knowledge, the inhibitory activity of varespladib against venom MPs is previously unreported. These findings suggest either direct inhibition of MP, a regulatory role for PLA2 in the activity of these key venom components, or both. This suggests a single agent or just a two- or three-drug combination could successfully treat the bite of several important, deadly snakes without need for antivenom and idea tested as described in Example 8.

Example 5

SP Activity assays

Figure 3:
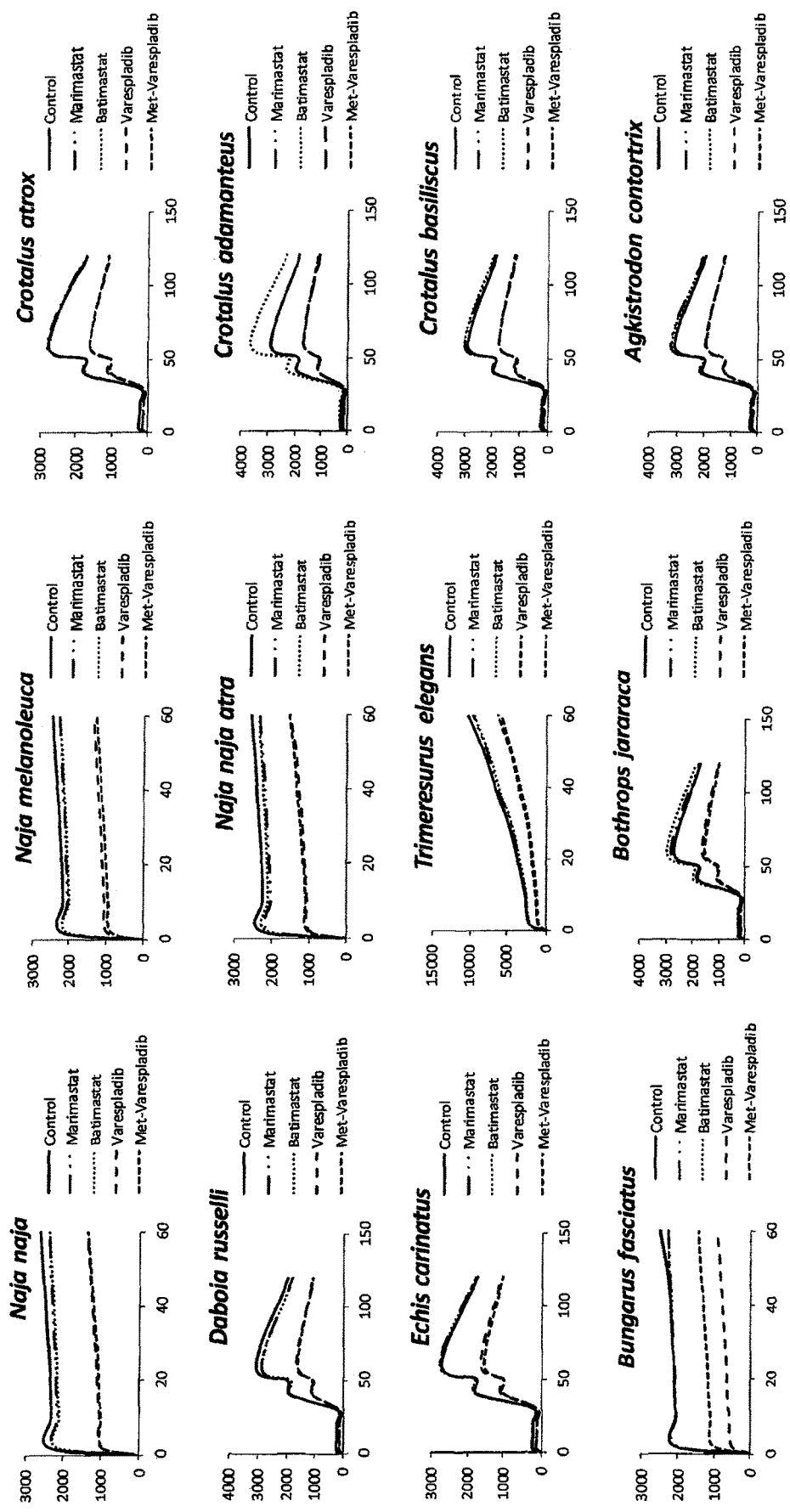
FIG. 3 shows a time course of serine protease activity when extremely high concentrations of venom were combined with known MP and sPLA2 inhibitors. Varespladib and methylvarespladib demonstrated inhibitory activity against snake venom SPs tested (Example 5).

FIG. 3 shows data from the same series in which high concentrations of venom (final concentration 0.444 mg/mL) were used for assaying sPLA2, MP and SP activity using the methods described in Example 1. Even at extremely high venom concentrations varespladib and methylvarespladib exerted unexpected inhibitory effects on snake venom serine proteases compared to marimastat and batimastat at the same concentrations (100 um) in vitro.

Example 6 sPLA2 Activity Assays

To confirm the findings from early experiments in which only high concentration venom solutions were used to assay the effects of sPLA2, and substrate consumption was performed lower concentrations selected PLA2 inhibitors such as varespladib and darapladib were performed in more appropriately optimized assay conditions and following manufacturer's recommendations. A further difference between this assay and as described in FIGS. 1, 2A and 3 is that assays were run at 25° C. Inhibition of snake venom PLA2 was seen for all the so-called 'Big 4' snakes of India: *N. naja*, *B. caeruleus* (and *B. fasciatus*) as well as *E. carinatus* and *D. russelli*. Notably, bee venom sPLA2 activity was not inhibited by either varespladib or darapladib.

Figure 4:
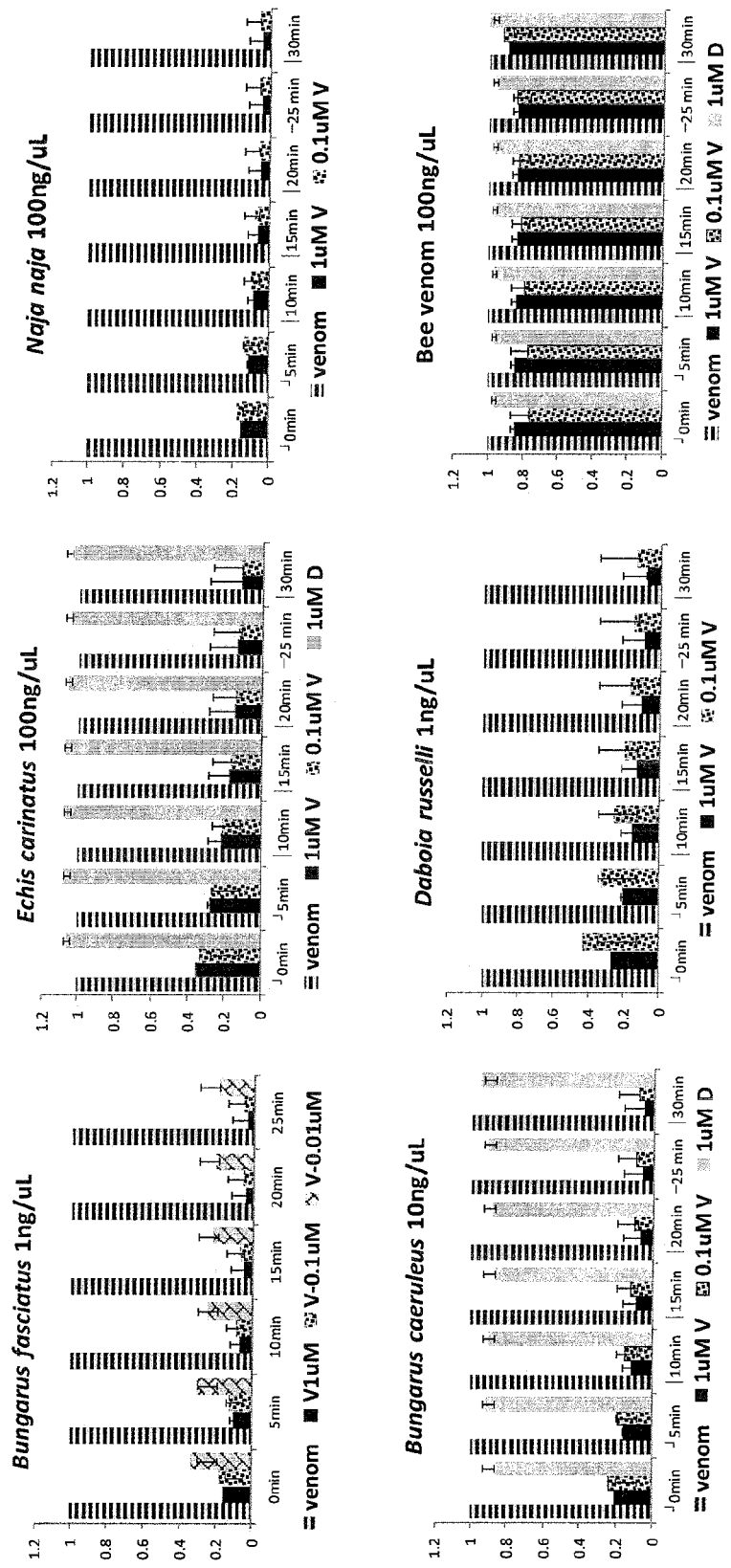
FIG. 4 shows inhibition of PLA2 activity of snake venoms by varespladib. Neither varespladib nor darapladib significantly inhibited sPLA2 of bee venom with the same degree of potency as for snake venom. Varespladib but not darapladib (negative control) effectively inhibits snake venom PLA2. Surprisingly, bee venom PLA2 is not inhibited by varespladib (Example 6).

FIG. 4 shows that varespladib but not darapladib (an Lp-PLA2 inhibitor) inhibited snake venom PLA2 in vitro. Surprisingly, bee venom PLA2 was not inhibited by either varespladib or darapladib. There was no apparent synergistic effect between darapladib and varespladib when the two agents were tested in combination (data not shown). Data were normalized to venom control. Assays were performed as in Example 1 except that venom activity was optimized prior to drug testing and much lower concentrations of varespladib were tested, but yielded the same conclusion: Potent inhibition of snake venom PLA2 enzyme activity.

FIGS. 5A-5R show that varespladib and methylvarespladib inhibited the measured sPLA2 activity of several medically important snake venoms in vitro (Dose-Response methods in Example 2). 5A) *Naja naja naja* 5B) *Bungarus caeruleus* 5C) *Daboia russelli* 5D) *Echis carinatus* 5E) *Oxyuranus scutellatus* and 5F) *Micrurus fulvius* 5G) shows that varespladib and methylvarespladib are less potent inhibitors of Bee Venom sPLA2 at concentrations up to 1 uM, and only a modest effect at concentrations up to 100 uM 5H) *Dendroaspis polylepis* 5I) *Acanthophis antarcticus* 5J) *Vipera berus* 5K) *A. blomhoffii brevicaudus* 5L) *Crotalus adamanteus* 5M) *Agkistrodon contortrix* 5N) *Crotalus atrox* 5O) *Crotalus scutulatus scutulatus* 5P) *Agkistrodon piscivorus* 5Q) *Crotalus atrox* repeat experiments 5R) *Crotalus scutalatus* repeat experiments. The breadth of action and high potency of varespladib (V) and methylvarespladib (V-m) against representative snake venom PLA2 from around the world is striking.

Example 7

Varespladib is Protective and Therapeutically Effective Against *M. fulvius* Venom in Mice and Rats This example shows that administration of varespladib (4 mg/kg unless stated otherwise) protected mice evenomated with *M. fulvius* venom (4 mg/kg).

Mice received SC injections of *M. fulvius* venom at ~4 times the expected LD50 (typically estimated to be 1.3 mg/kg SC) (0.1 mg *M. fulvius* venom/animal for approximate dose of ~4 mg/kg). Prior to venom injection animals received either total dose 0.1 mg varespladib exipient (sham treatment) by SC route for calculated concentration of 4 mg/kg varespladib ~10-15 minutes before venom administration. Surviving animals were euthanized by CO2 inhalation at the end of experiments and observations periods ranging from ~12 hours to as long as 30 hours (survival being designated at 24 hours). Surprisingly, many animals survived with only single doses of varespladib rather than just extending their survival times. Another surprise was the virtual absence of hemorrhagic complications and gross hemolysis seen in control animals. In fact, there was virtually no gross hemolysis in treated animals (e.g. 6 G) and little or no pulmonary hemorrhage on necropsy. Venom-induced rises in PLA2 were suppressed by varespladib and corresponded with both clinical descriptions of the animals and gross hemolysis (or lack of). Typically, animals were found to be bright, active and responsive when treated with therapeutically effective doses of varespladib. Treatment of mice with methylvarespladib prior to administration of high dose venom conferred complete protection from the effects of the venom and suggests that immediate field treatment of bites by an oral formulation is very plausibly realistic by blocking critical venom components before they have spread in the manner typical by the time patients receive medical attention. One important implication of these experiments (oral and parenteral) is that a single agent antidote for one or more medically important snake venoms can mitigate both neurotoxic and hemotoxic components of snake venom with life-saving effect. Because some mice died with only a single treatment (in the absence of dose-finding studies), it is contemplated that PLA2 inhibitor (e.g., varespladib) may be administered more than once in some therapeutic regimens and/or a varespladib treatment may be followed with auxiliary treatments with other agents. FIG. 6A-H shows the effects of varespladib in mice or rats envenomed with *M. fulvius* venom at various concentrations usually at 4-8 mg/kg and pre-treated or treated usually only one time with varespladib confers a huge survival advantage over placebo (excipient) treated animals. In mice: Varespladib 4-8 mg/kg subcutaneously or orally with methylvarespladib, taken ad libitum. In rats, varespladib or excipient was administered intravenously at 30 seconds or 5 minutes following subcutaneous administration of venom at 4 or 8 mg/kg. Blood sampling and assay for sPLA2 activity was performed with samples taken from a surgically implanted jugular venous catheter at precise intervals (baseline, 30 minutes, 1 hour and 4 hours). It was from this sampling that the first observation of protection from hemolysis was made (6 G). This unexpected effect of varespladib—protection from hemolysis—suggests, without committing to, multiple mechanisms by which varespladib-based therapeutics can prevent or mitigate coagulopathies and tissue damage.

FIG. 6A shows the fate of 5 of 5 (100%) of mice given 4 mg/kg SC injections of *M. fulvius* venom. Control mice died quickly with paralytic and hemorrhagic complications. 0 of 5 (0%) of mice pre-treated with varespladib (4 mg/kg) minutes before venom injection died within 8 hours. Only one showed any evidence of hemorrhage, but this was significantly less than the controls. Surviving mice showed no gross evidence of coagulopathy or hemorrhage at death (2 of 5). Two mice survived and one at 30 hours had only mild ptosis that was significantly improved between 24 and 30 hours post venom administration. A Kaplan-Meier survival plot shows profound survival benefit of varespladib treatment. 6B Mice fed methylvarespladib or exipient ad libitum in biscuits had high-dose *M. fulvius* venom administered ~5 hours after introduction of the biscuits (N=2 each group). Neither treated mouse exhibited any signs or symptoms of envenomation and were bright, active and responsive throughout, resuming running on their wheel minutes after venom administration. 6C Venom and varespladib (4 mg/kg) or venom and excipient were mixed just prior to administration and injected subcutaneously. At 5 hours (300 minutes, down-pointing arrow), surviving animals were retreated with ½ dose varespladib (2 mg/kg) or excipient. 5/5 treated mice survived to the endpoint of 24 hours (1440 minutes) and 4/5 controls eventually succumbed. 6D Results of two experiments using the same protocol. Mice either received venom and sham/excipient (N=7), methylvarespladib (N=3) or varespladib (N=7) ~30 seconds to 1.5 minute following venom administration. This is the first demonstration that varespladib can be given in therapeutic mode as a single agent therapy for envenomation. Confirmatory experiments and results of 6E-H were performed in rats by a contract laboratory to assess expand knowledge of varespladib's capacity to act in therapeutic mode and see if the effects of intravenous administration were similar to subcutaneous administration. 6E and 6F *M. fulvius* venom was administered subcutaneously (4 mg/kg or 8 mg/kg) and then excipient or varespladib 8 mg/kg was administered at 30 seconds or 5 minutes after envenomation. 12/12 treated animals survived 24 hours with 10/12 being described as "bright, active and responsive" while 6/6 control animals died in under 500 minutes. All control animal's serum samples exhibited gross hemolysis while treated animals had no or minimally visible hemolysis (6G—sample at right, 4 hour time-point, T=5 minutes). At necropsy, treated animals had either no or minimal pulmonary hemorrhage while all examined control animals had gross evidence of pulmonary hemorrhage. 6H Shows dramatic suppression of sPLA2 activity in the face of high dose coral snake venom administered SC and resulting in 100% mortality within 8 hours (Venom/Excipient) and 100% survival in treated animals (4 mg/kg venom N=6; 8 mg/kg venom N=6). 12/12 animals surviving received varespladib intravenously either at 30 seconds or 5 minutes post venom administration.

Example 8

Figure 7:
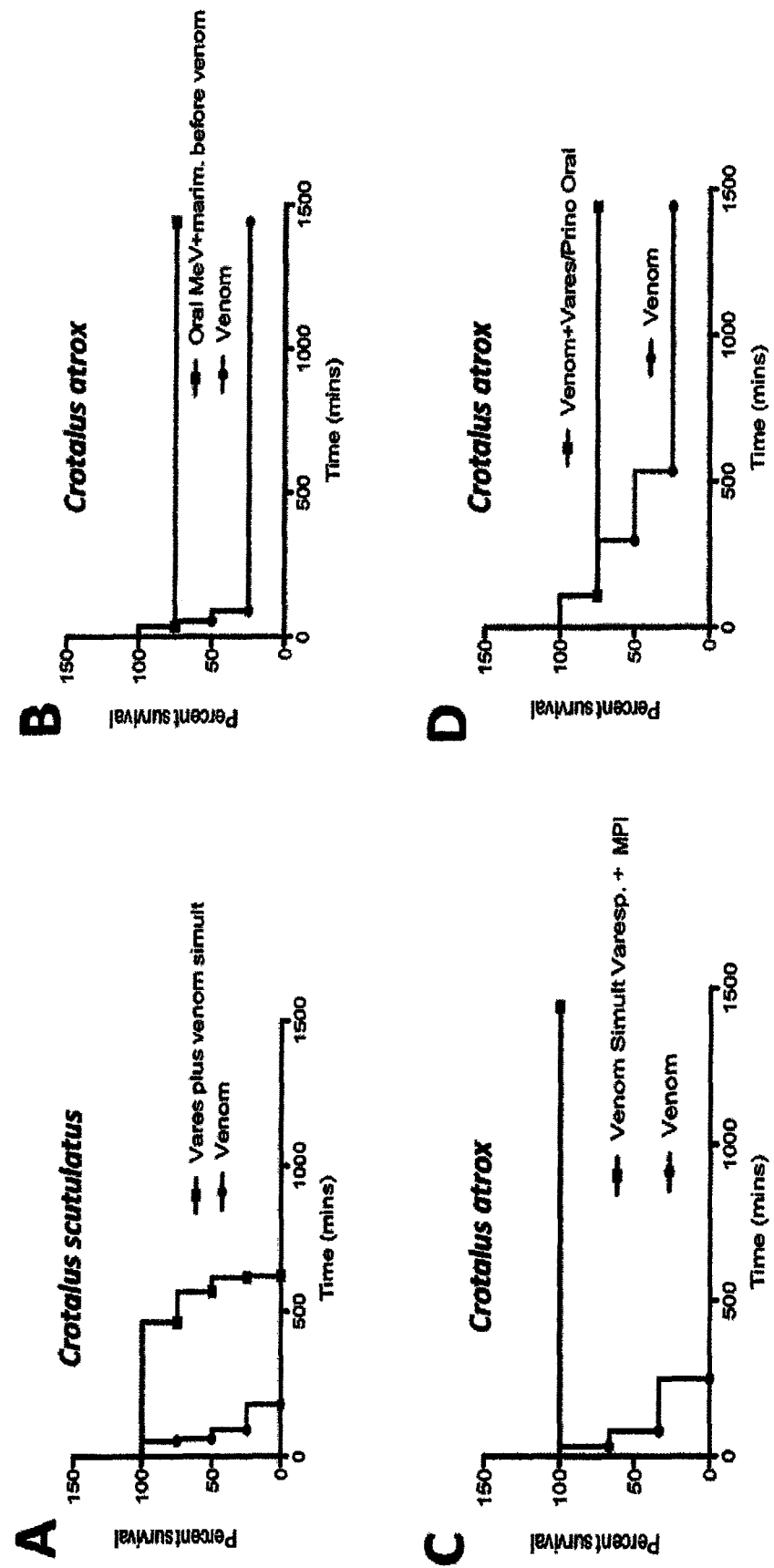
FIG. 7 shows improved survival in mice co-injected with rattlesnake venom and varespladib or varespladib and an MP inhibitor. Additionally, mice fed methyl-varespladib and an MP inhibitor were protected from death by rattlesnake (*C. atrox*) venom (Example 8).

(FIG. 7): Varespladib-Based Therapies are Protective Against Death by Crotalid Envenomation As shown in FIG. 7, varespladib and methyl-varespladib are the foundation of successful pharmacolotherapy for viper envenomation alone or in combination with an MP inhibitor such as prinomastat, for example or an SP inhibitor given parenterally or orally. 7A. Mice coinjected with *C. scutulatus* venom and single dose varespladib outlived controls injected with venom alone (Venom only control, subcutaneous (SC) N=4; Venom+Varespladib SC N=4). 7B. Mice fed methyl-varespladib+marimastat ad libitum prior to envenomation outlived controls injected with venom alone (Venom alone SC N=4; Venom+PO Varespladib/Marimastat N=4). 7C. Mice coinjected with venom and single dose of varespladib+mixture of marimastat/batimastat outlived controls (Venom alone SC, N=3; Venom+Varespladib/MP inhibitor mixture N=3). 7D. Mice fed ad libitum a biscuit treated with methyl-varespladib and prinomastat were protected from death by *C. atrox* venom injected subcutaneously 3 hours after biscuits were placed in cage and each mouse directly observed to have fed on assigned biscuit at least once (N=4 each group).

Example 9

(FIG. 8): Varespladib Protects Mice from Death by *Daboia russelli* Venom

Figure 8:
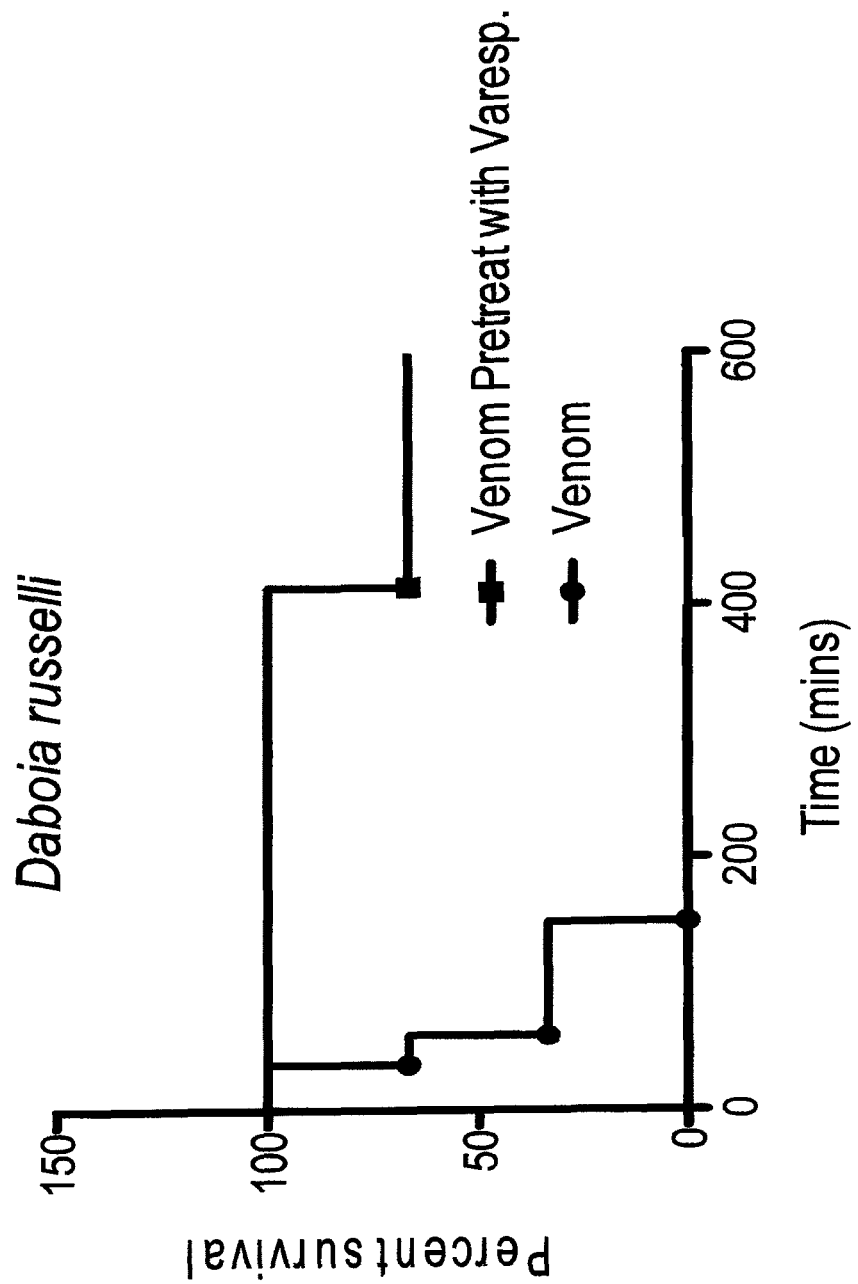
FIG. 8. Mice pretreated with varespladib subcutaneous injection were protected from death by administration of *Vipera* (*Daboia*) *russelli* venom that was also injected subcutaneously (Example 9).

*Daboia russelli* is a major killer and among the "Big 4" in India. Hematological and neurological catastrophes are common with highly variable presentations of bleeding and paralysis resulting neurological, renal and limb threatening catastrophes. Varespladib in this scenario is protective against peripheral and central nervous system insult, kidney failure and catastrophic bleeding. Mice pretreated with varespladib 4 mg/kg administered subcutaneously 60 to 90 minutes before an otherwise lethal dose of *D. russelli* venom outlived controls as shown in FIG. 8 (N=3 each group). All mice had local hematoma at the site of injection, but controls appeared to die exclusively from paralysis. Treated animals all survived 24 hours, but at 30 hours became weak and died from uncertain cause possibly related to venom effects, directly or indirectly.

Example 10

Figure 9:
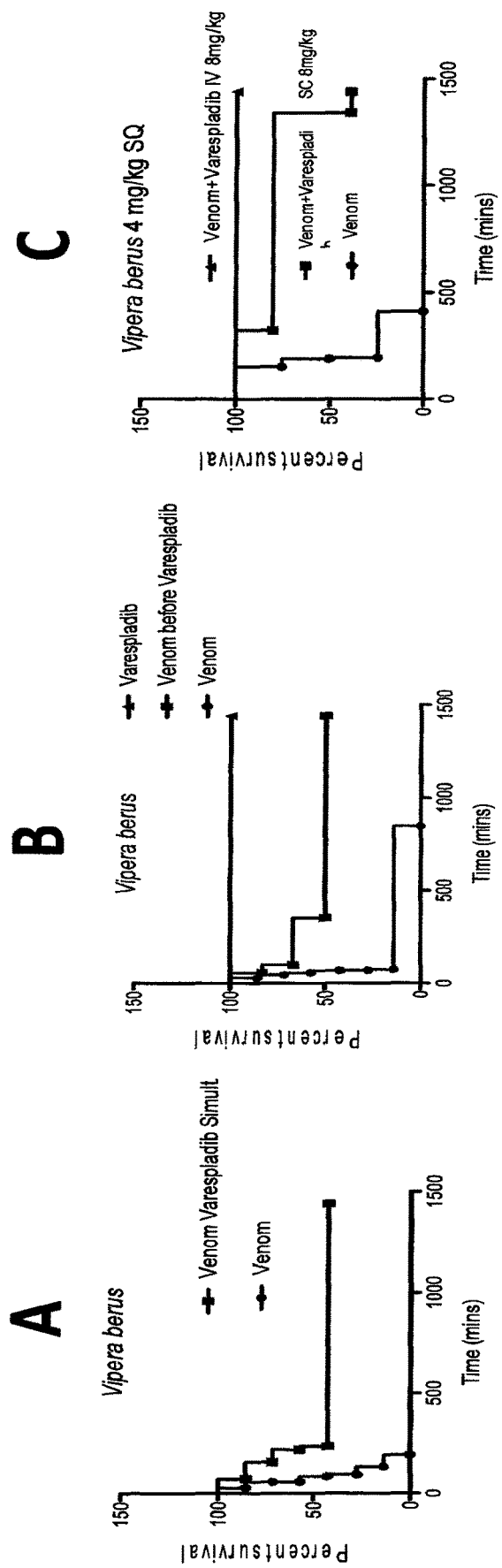
FIG. 9 Varespladib is protective and therapeutically effective against lethal doses of *Vipera berus* (Common adder) venom in mice (Example 10).
Figure 10:
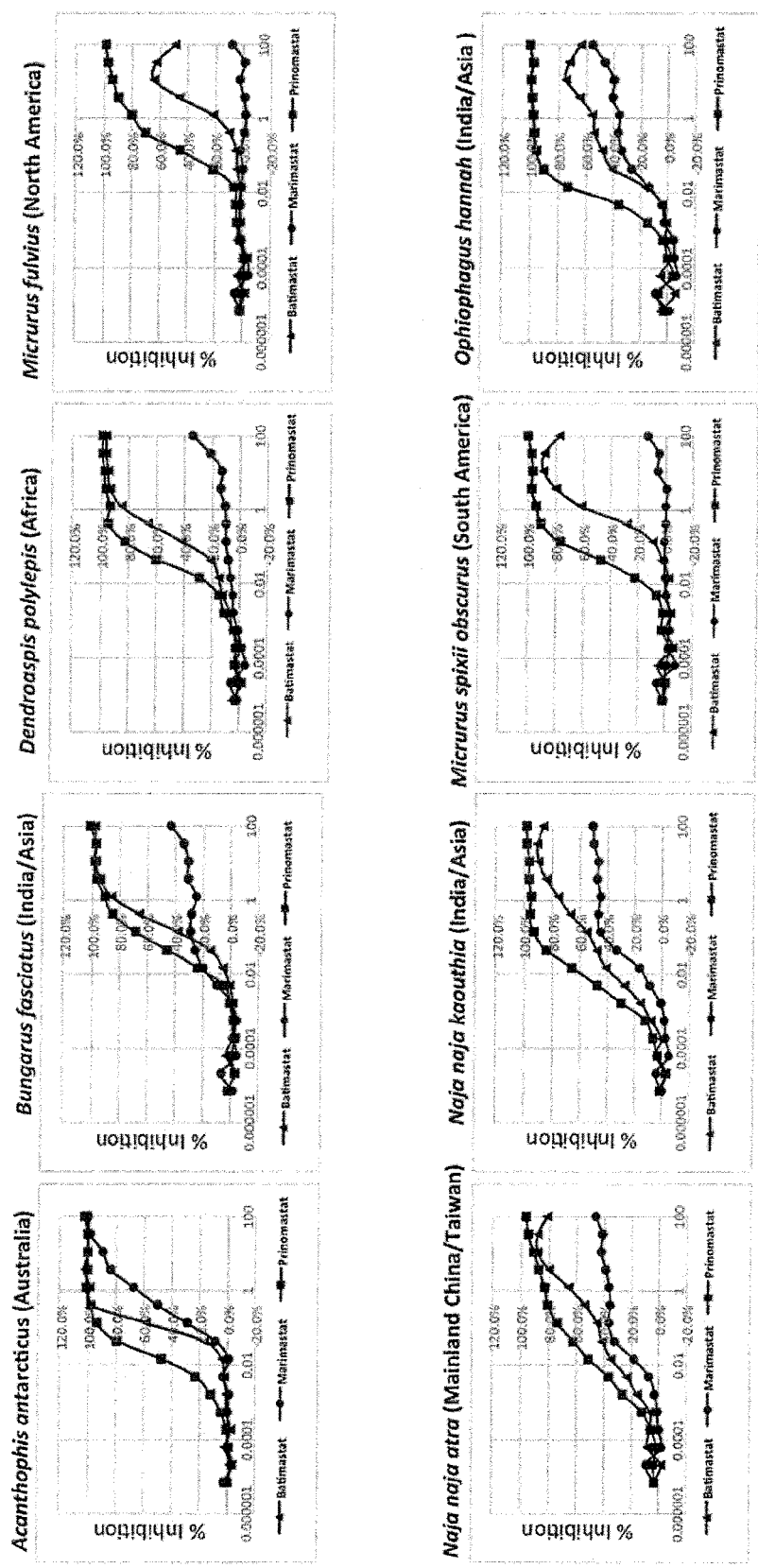
FIG. 10 shows Prinomastat, batimastat and marimastat inhibition of elapid venoms in vitro.
Figure 11:
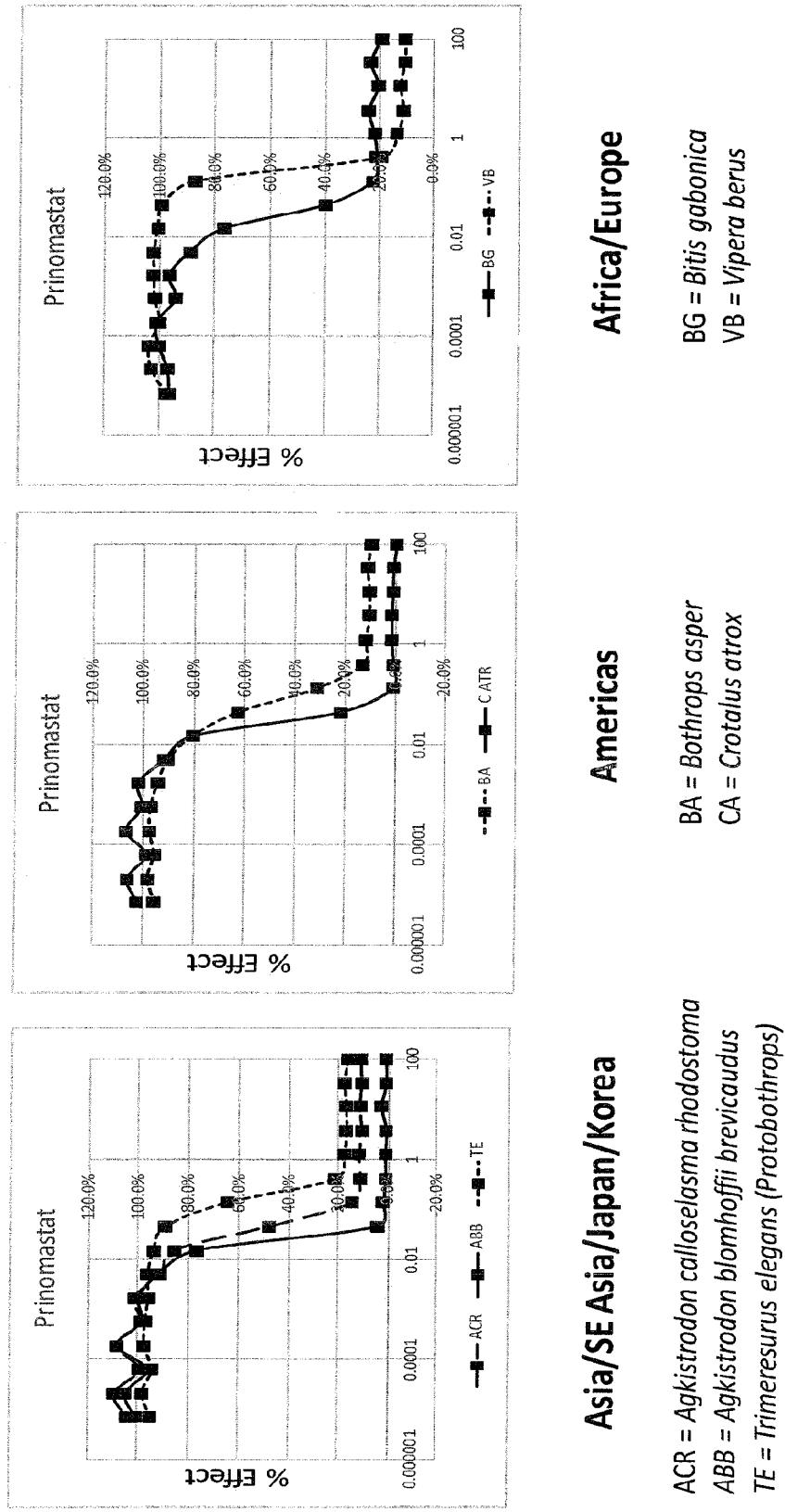
FIG. 11 shows the effect of Prinomastat as an MP inhibitor of viper venoms in vitro.
Figure 12:
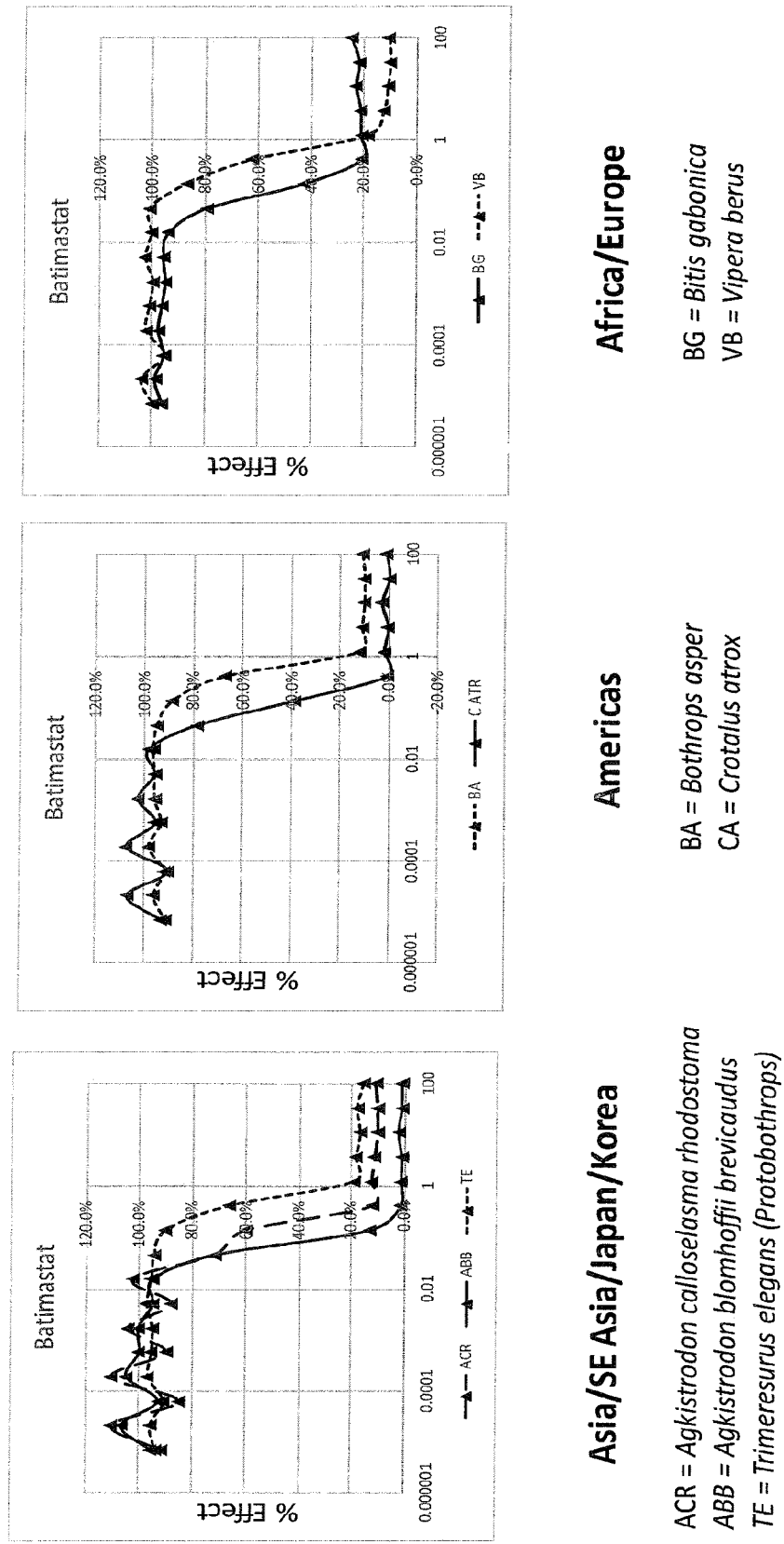
FIG. 12 shows the effect of Batimistat as an MP inhibitor of viper venoms in vitro.
Figure 13:
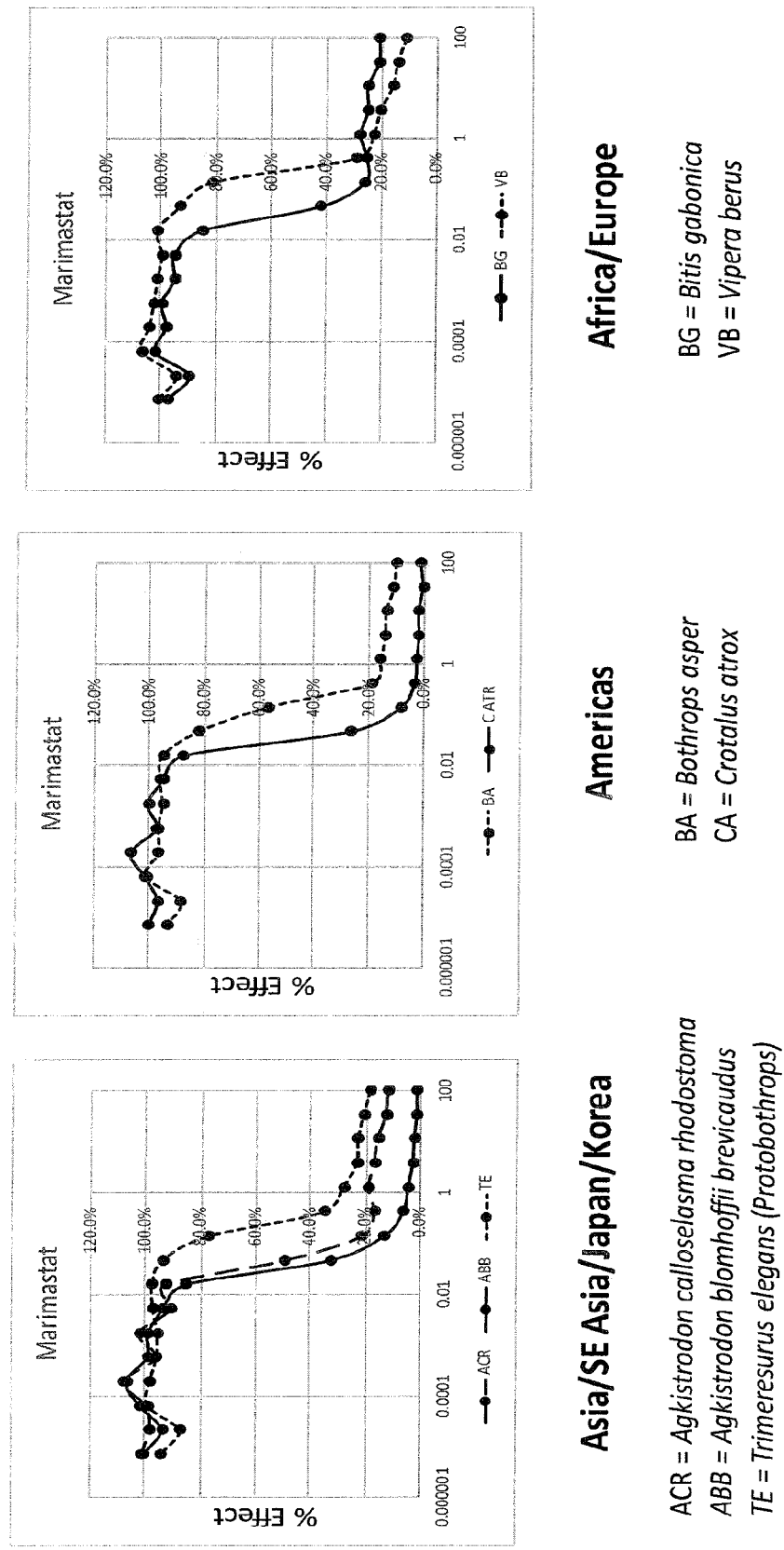
FIG. 13 shows the effect of Marimastat as an MP inhibitor of viper venoms in vitro.
Figure 14:
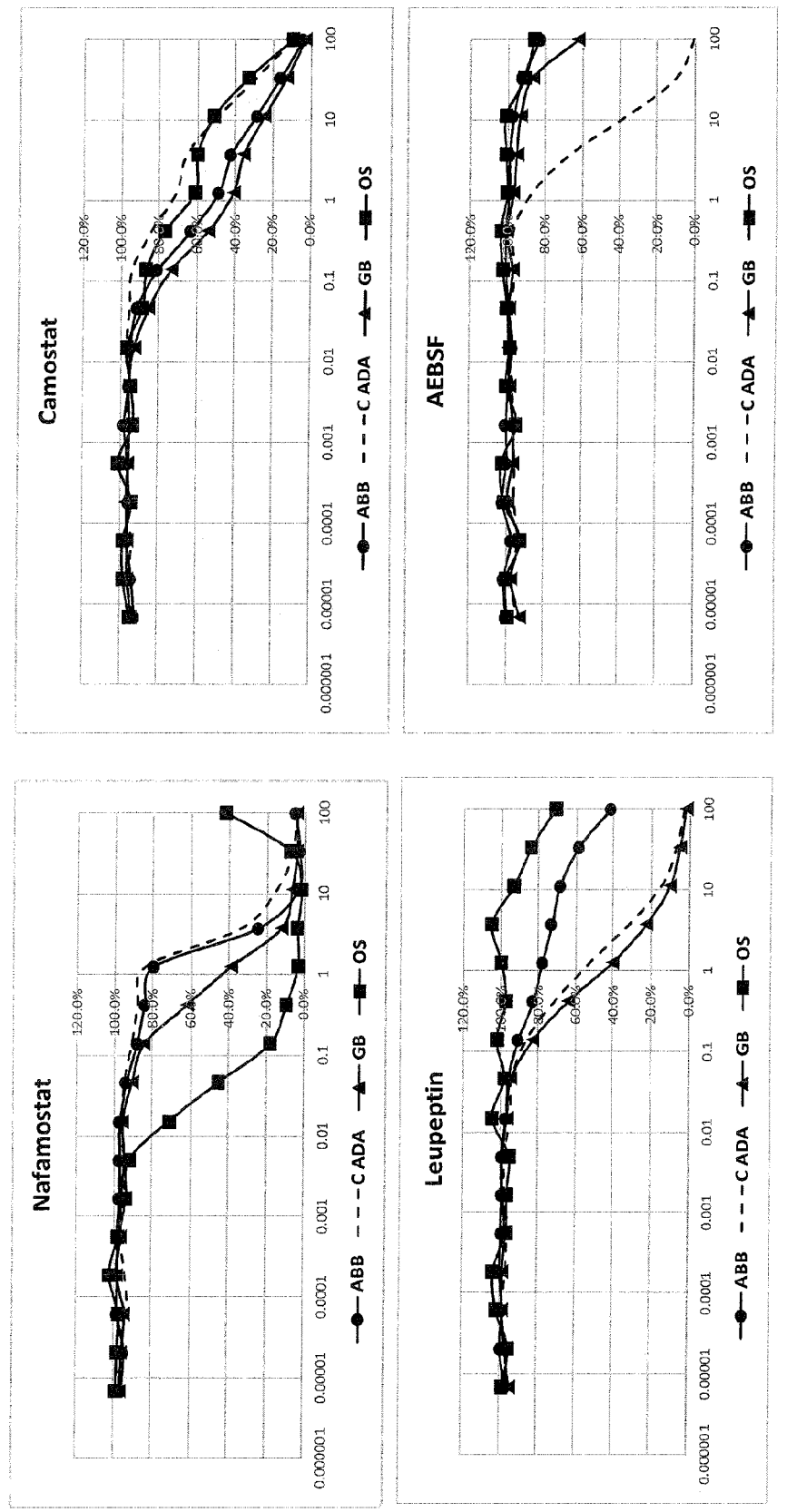
FIG. 14 shows the effect of inhibitors of serine proteases in vipers and one elapid (in vitro). Nafamostat had surprising activity against the elapid, *Oxyuranus scutellatus*, in vitro.

(FIG. 9): Varespladib is Protective and Therapeutically Effective Against *Vipera berus* Venom In Vivo in Mouse As shown in FIG. 9 Mice injected with lethal doses of *Vipera berus* venom outlived or were completely protected from death when treated with varespladib administered subcutaneously (4 or 8 mg/kg unless stated otherwise) at the same time as or after venom administration. All mice treated with IV varespladib following administration of venom survived 24 hours. *V. berus* is the most widely distributed viper in the world, ranging across Europe and Eurasia and as far north as the Arctic circle. It elaborates both hemo- and neurotoxins dangerous especially to children, pets and large animals such as horses. 9A Venom and varespladib injected simultaneously into the subcutaneous space outlived controls (venom+excipient) N=7 each group. 9B Mice injected with lethal doses of venom just prior to SC administration of varespladib outlived controls (N=7 each). Those injected with varespladib alone showed no signs of toxicity (N=2). 9C Varespladib administered SC or IV (8 mg/kg) in the lateral tail vein following venom administration resulted in significant survival benefit with 5 of 5 treated with intravenous varespladib animals surviving 24 hours in scruffy condition and 0/5 control animals surviving past 7 hours. 4 of 5 animals treated following venom administration (Venom SC followed by Varespladib SC) outlived controls.

Example 11

Combination of Antivenom and Varespladib

The purpose of this experiment was to determine how varespladib and the antivenom, CroFab® (Crotalidae Polyvalent Immune Fab (Ovine) snake antivenom; BTG Plc.) interact to block the key venom component PLA2. Using the assay described in Example 2, the IC50% was determined CroFab® alone, varespladib alone, and varespladib and CroFab® together. It was not predictable whether the two compositions would interfere with each other or have an additive effect. Surprisingly, a synergistic effect was observed.

A BLISS Independence calculation (Analysis is conducted using the regression approach developed in Cokol et al. (2011) *Systematic exploration of synergistic drug pairs. Molecular System Biology.* 7: 544) The main quantity is "beta" in the first equation. A beta value less than 1 suggests synergy, whereas a beta value greater than 1 suggests antagonism. The analysis results are as follows. "p-value" is the significance level of the beta value. Beta values (in parentheses) showing synergy between varespladib and polyvalent crotaline antivenom aka "CroFab®" were: *A. contortrix* (0.86) *C. atrox* (0.848) *C. adamanteus* (0.855) and *A. antarcticus* an Australian elapid related to cobras (0.725). For each of these four examples p-value<0.0001. IC50s for this experiment are reported in Table 1 below.

TABLE 1

Synergistic Activity of Antivenom (CroFab ®) plus small molecule inhibitor of sPLA2 (Varespladib)

| | Varespladib $IC_{50}$ (nM) With CroFab ® | Varespladib ($IC_{50}$ nM) | CroFab ® ($IC_{50}$ mg/mL) |
|---|---|---|---|
| Agkistrodon piscivorus | 0.05 | 0.28 | 2.86 |
| Agkistrodon contortrix | 0.045 | 0.22 | 5.51 |
| Crotalus scutulatus scutulatus | 0.82 | 1.51 | 16.2 |
| Crotalus otrox | 0.07 | 0.32 | 4.85 |
| Crotalus adamanteus | 0.05 | 0.25 | 3.96 |
| Acanthophis antarcticus | 0.43 | 0.74 | 190.6 |

The above experimental procedure was then carried out for selected MP inhibitors alone and in combination with CroFab® alone and with varespladib TABLE 2, below. Table 2 Illustrates the effects of different inhibitors in combination with antivenom.

In this example, CroFab®. The concentration at which CroFab® inhibited 50% of snake venom MP activity was found and then additional inhibitors added in order to determine if the remaining 50% MP activity could be effectively neutralized. Data for the combinations are shown. Where varespladib (1 uM) was added, it was done so in order to neutralize background PLA2 activity. Prinomastat, marimastat and batimastat were selected based on their ability to neutralize snake venom MPs as determined in experiments in Table 1. *A. blomhoffi* was included to see if a situation in which an antivenom not indicated for a particular snake could be made more effective by the addition of one or more small molecule inhibitors.

TABLE 2

Effects of Different Inhibitors in Combination with Antivenom

| Venom | INHIBITOR COMBINATION | R-square | $IC_{50}$ for Inhibitor (uM) CroFab ® (mg/mL) |
|---|---|---|---|
| *A. blomhoffii brevicaudus* | CroFab ® alone | 0.995 | 0.37 |
| | CroFab ® + Prinomastat | 0.997 | 0.02 |
| | Prinomastat + Varespladib | 0.993 | ~0.02 |

TABLE 2-continued

Effects of Different Inhibitors in Combination with Antivenom

| Venom | INHIBITOR COMBINATION | R-square | $IC_{50}$ for Inhibitor (uM) CroFab ® (mg/mL) |
|---|---|---|---|
| C. atrox | CroFab ® alone | 0.996 | 0.18 |
| | CroFab ® + Prinomastat | 0.980 | 0.02 |
| | Prinomastat + Varespladib | 0.975 | 0.04 |
| C. durissus terrificus | CroFab ® alone | 0.998 | 0.09 |
| | CroFab ® + Prinomastat | 0.929 | ~0.01 |
| | Prinomastat + Varespladib | 0.987 | ~0.01 |
| C. scutulatus scutulatus | CroFab ® alone | 0.998 | 0.02 |
| | CroFab ® + Prinomastat | 0.638 | ~0.01 |
| | Prinomastat + Varespladib | 0.920 | 0.002 |

Illustrations the effects of various inhibitors on snake venom metalloproteases. *A. blomhoffi brevicaudis* is not a snake for which CroFab® antivenom therapy in indicated but the addition of prinomastat to the antivenom or the combination of prinomastat+varespladib without antivenom illustrates two novel ways in which a specific polyvalent antivenom or a paraspecific antivenom can be made effective (small molecule+antivenom or small molecule such as prinomastat+a varespladib-based molecule).

The methods employed in example 2, above, were followed in order to generate $IC_{50}$ values for varespladib, methylvarespladib (for $PLA_2$ inhibition), and for prinomastat, marimastat, batimastat, vorinostat, ilomastat, gabexate and nafamostat on various venoms as set forth in Tables 3-8 of FIGS. 15-20 and in FIGS. 10-14. The results of these experiments were tabulated and presented in the tables and Figures. The results evidence that in many instances, the $IC_{50}$ values of varespladib and methylvarespladib for inhibition of $PLA_2$ are surprisingly low for an astonishing array of snake venoms. The same is true for the $IC_{50}$ values of prinomastat, marimastat and batimistate for inhibition of Metalloproteinase. As indicated, vorinostat, gabexate and nafamostat were somewhat less effective, generally with $IC_{50}$s in the micromolar range. Prinomastat has not previously been known have such a broad range of inhibitory effect on snake venoms.

Example 13

HTS Discovery of Useful Inhibitors of *C. Atrox* Venom MP (Representing New World Vipers)

High Throughput Screening (HTS), as described in Example 2, was carried out to identify inhibitors of *C. Atrox* venom MP useful in combination with varespladib or methyvarespladib for treatment of envonomation by *C. Atrox* and other new world vipers. Results are given as the percental (%) reduction of MP activity. Agents screened included FDA approved drugs, bioactive lipids and protease inhibitor libraries (YCMD libraries: GenPlus, FDA approved drugs, NCC, Pharmakon 1600, Bioactive lipid and Protease libraries). The following agents inhibited at least 1% of MP activity. Unexpectedly MP inhibition was seen with gabexate. Gabexate is an approved marketed drug with broad effects on the inflammatory pathways and is a serine protease inhibitor. It was not expected that a SP inhibitor would also inhibit a zinc protease like the MP family. CGS 27023 had a >95% effect. Actinonin had a 92% effect and could be considered useful in an acute situation. Vorinostat was notable for a 42% effect. Aspartame at 6.31% and other artificial sweeteners may be useful as partial inhibitors while serving to improve the taste of varespladib and methylvarespladib which are slightly bitter and varespladib salty when mixed with bicarbonate and 10% dextrose (personal observation).

Example 14

HTS Discovery of MP Inhibitors Against *E. carinatus* (Representing Old World Vipers)

High Throughput Screening (HTS), as described in Example 2, was carried out to identify inhibitors of *E. carinatus* venom MP useful in combination with varespladib or methyvarespladib for treatment of envonomation by *E. carinatus* other old world vipers. HIGH THROUGHPUT SCREENING INCLUDING FDA approved drugs, bioactive lipids and protease inhibitor libraries (YCMD libraries: GenPlus, FDA approved drugs, NCC, Pharmakon 1600, Bioactive lipid and Protease libraries): With a 67% Effect. Cefixime and other cephalosporins had surprisingly robust effects against *E. carinatus* MP and are useful to prevent envenomation effects, infection and inflammation, especially in combination with varespladib or methyl-varespladib and combinations thereof with one or more of the following: With a 28% Effect. Norepinephrine and other sympathetic and dopaminergic agents known to be useful in Parkinson's disease are unexpectedly useful, FDA approved and readily available where *E. carinatus* is indigenous. With a 28% Effect, Nafamostat, and FDA approved serine protease inhibitor had unexpected activity against taipan snakevenom serine protease and is similar in structure to gabexate which showed a 23% effect. Aspartame had a 6% effect similar to that seen with *C. atrox* and might be included in oral formulations of varespladib-based therapies to improve the taste (inventor's observation). Injection of varespladib-based therapy in conjunction with bupvicaine >10% effect decreases pain of injection and paralyses lymphatic muscle slowing the spread of venom.

Example 15

HTS Discovery of Elapid PLA2 inhibitors Using *M. fulvius* Venom

High Throughput Screening (HTS), as described in Example 1, was carried out to identify inhibitors of *M. fulvius* venom PLA2 useful in combination with varespladib or methyvarespladib for treatment of envonomation by elapids. (YCMD libraries: GenPlus, FDA approved drugs, NCC, Pharmakon 1600, Bioactive lipid and Protease libraries): Ceramide (Ceramine) had a 43% effect (% inhibition). Others found to be useful as well as suramin and other mixtures and compositions thereof in combination with varespladib, methyl-varespladib, B-vitamins, antibiotics indoxam and others noted below, some of which also have useful MP and SP inhibitory properties. Suramin, an antiparasitic 21% effect, Lidocaine 11% tropicamide >15% and atropine >20% effect can be combined in parenteral, oral, nasal and ocular formulations of varespladib-based therapeutic strategies especially in conjunction with Neostigmine, rivastigmine and physostigmine all with 15% to 20% inhibitory effect on elapid sPLA2 with great utility and effect to additionally neutralize post-synaptic snake venom alpha-toxins causing weakness.

Example 16

Formulation Example—Dosages and Dosage Forms

A. Exemplary Injectable Formulations

Exemplary injectable formulations of the invention include the following (excipients as illustrated in U.S. Patent Application Document No. 20120232031):
1. An aqueous injectable solution comprising a $PLA_2$ inhibitor in 10% beta-hydroxypropyl cyclodextrin (BHPC) in water;
2. An aqueous injectable solution comprising a $PLA_2$ inhibitor (1.0 g), ethyl alcohol (0.5 mL), ascorbic acid (0.5 g), chlorobutanol (0.1 mL), sodium hyaluronate (10 g) and sodium chloride (0.9%) qs to 100 mL;
3. An aqueous injectable solution comprising a $PLA_2$ inhibitor (2.0 g), poly(lactic acid)(PLA) (1.0 g), sodium citrate (1 mL), Ringer's Solution qs to 100 mL;
4. An aqueous injectable solution comprising a $PLA_2$ inhibitor (1.5 g), copolymers of lactic and glycolic acid (PLGA) (1.5 g), benzyl alcohol qs to 2% Vitamin E 1 ml, corn oil qs to 100 mL; and
5. An aqueous injectable solution comprising a $PLA_2$ inhibitor (2.5 g), copolymers of lactic and glycolic acid (PLGA) (1.5 g), benzyl alcohol qs to 2%, Vitamin E 1 mL, corn oil qs to 100 mL.

B. Nasal Spray Inhaler

An exemplary nasal spray inhaler contains an aerosol spray formulation comprising:
(a) a metalloproteinase inhibitor such as batimastat or a serine protease inhibitor;
(b) a phospholipase $A_2$ ($PLA_2$) inhibitor for example, selected from the group consisting of effipladib, Lilly 315920 (varespladib), LY 311727, BMS 181162, YM 26567, variabilin, SB 203347, recombinant PAF-AH, darapladib, among others and compositions comprising at least one phopholipid selected from the group consisting of phosphatidylethanolamine (PE), phosphatidylserine (PS), phosphatidylcholine (PC), phosphatidylinositol (PI), and phosphatidylglycerol (PG) and mixtures thereof linked (conjugated) to at least one compound selected from the group consisting of carboxymethylcellulose (CMPE, CMC-Peor CME), hyaluronic acid (HYPE, HyPE, and Hyal-PE), heparin (HEPPE, HepPE, HePPE, Hepa-PE), chondroitine sulfate A (CSAPE, CsaPE, CsAPE), Polygeline (haemaccel) (HemPE, HEMPE), hydroxyethylstarch (HesPE, HESPE) and mixtures thereof; and
(d) a pharmaceutically acceptable dispersant;
wherein the nasal spray inhaler is metered to disperse an amount of the aerosol formulation by forming a spray that contains a dose of the metalloproteinase inhibitor or serine protease inhibitor and phospholipase $A_2$ ($PLA_2$) inhibitor which is effective to treat an envenomation.

One exemplary dose of the metalloproteinase inhibitor and phospholipase $A_2$ ($PLA_2$) inhibitor which is effective to treat an envenomation includes about 0.01, 0.1, 1, 10, 100 and 1,000 mg of the metalloproteinase inhibitor and phospholipase $A_2$ ($PLA_2$) inhibitor, or in an amount of between about 0.001, 0.01, 0.1, 1, 10, 20, 30, 40, 50, 60, 70, 80, 90 to about 100 g of each of the metalloproteinase inhibitor and $PLA_2$ inhibitor dispersed, dissolved or diluted in a pharmaceutically-acceptable carrier (excipient) to yield an inhibitor concentration of 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 230, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 525, 550, 575, 600, 625, 650, 675, 700, 725 to about 750 µM or as high as 800, 850, 900, 950 or 1,000 µM.

Example 17

Response to Snakebite

A subject with known or suspected snakebite exhibits no or few, if any, or in certain instances, early signs of weakness in form of lid-lag or other bulbar palsy, pain at the bite site or bleeding and the venomous or non-venomous nature of the snake is known or unknown. A companion, a medical practitioner or the patient administers intranasally, orally or by by injection, aerosol or combination of these delivery routes including inhibitor-containing paste directly a therapeutically effective amount of a composition which comprises at least one $PLA_2$ inhibitor which is preferably varespladib and/or methylvarespladib, and optionally, at least one additional active ingredient selected from the group consisting of a metalloproteinase inhibitor, a serine protease inhibitor, an acetylcholinesterase inhibitor, nAChR agonist (e.g. nicotine or cotinine) (administered preferably by injection), a muscarinic acetylcholine receptor (mAChR) antagonist (e.g. glycopyrrolate or atropine in the appropriate ratio with the selected acetylcholinesterase inhibitor), a NMDA receptor antagonist (e.g. dizocilpine (MK-801)), a spreading factor inhibitor and optionally, lidocaine and/or bupivacaine. The subject thereafter exhibits clinical improvement in the form of improved muscle function (determined by subjective improvement in strength, mobility and ease of breathing, or by quantitative means such as by electro-myographic techniques and other standardized measures of strength). If the patient's condition deteriorates, then additional doses of the aforementioned therapeutic agents are administered in appropriate intervals until the patient either recovers or more common resuscitative techniques are available or needed. Advantageously, and in contrast to conventional methods, the aforementioned treatment regimen may be administered by someone with minimal or no medical training (e.g. a subject who is not medically trained and who must self-administer in the field), including the envomenation patient or subject themselves.

REFERENCES

References (Selected, Alphabetical)

2. Abhijit Dey and Jitendra Nath De, 2012. Phytopharmacology of Antiophidian Botanicals: A Review," *International Journal of Pharmacology*, 8: 62-79
3. Alirol et al., 2010, "Snakebite in South Asia: A Review" *PLoS Negl Trop Dis.* 4(1): e603
4. Anil, A., S. Singh, A. Bhalla, N. Sharma, R. Agarwal, and I. D. Simpson. 2010. Role of neostigmine and polyvalent antivenom in Indian common krait (*Bungarus caeruleus*) bite. *J. Infect. Prev.* 3:83-87.
5. Arora, P., S. Sharma, and S. Garg. 2002. Permeability issues in nasal drug delivery. *Drug Discov. Today* 7:967-975.
6. Broggini, M., C. Benvenuti, V. Botta, A. Fossati, and M. Valenti. 1991. Bioavailability of intranasal neostigmine: comparison with intravenous route. *Methods Find. Exp. Clin. Pharmacol.* 13:193-198.
7. Casewell, et al., "Medically important differences in snake venom composition are dictated by distinct postgenomic mechanisms", Proceedings of the National Academy of Sciences 111.25 (2014): 9205-9210
8. Chippaux, J. P. 2008. Estimating the global burden of snakebite can help to improve management. *PLoS Med.* 5:e221.
9. Cokol et al. (2011) Systematic exploration of synergistic drug pairs. *Molecular System Biology.* 7: 544)
10. Costantino et al., 2008, "Intranasal administration of acetylcholinesterase inhibitors," *BMC Neuroscience* 2008, 9(Suppl 3):S6;
11. Currie et al., 1988, "Resolution of neurotoxicity with anticholinesterase therapy in death-adder envenomation. Med. J. Aust. 148:522-525)
12. Dennis, Edward A., et al. "Phospholipase A2 enzymes: physical structure, biological function, disease implication, chemical inhibition, and therapeutic intervention." *Chemical reviews* 111.10 (2011): 6130-6185
13. Di Costanzo, A., A. Toriello, C. Mannara, C. Benvenuti, and G. Tedeschi. 1993. Intranasal versus intravenous neostigmine in myasthenia gravis: assessment by computer analysis of saccadic eye movements. *Clin. Neuropharmacol.* 16:511-517.
14. Dooley, J. M., K. J. Goulden, J. G. Gatien, E. J. Gibson, and B. S. Brown. 1986. Topical therapy for oropharyngeal symptoms of myasthenia gravis. *Ann. Neurol.* 19:192-194
15. Fossati, A., M. G. Vimercati, G. L. Bandi, and A. Formenti. 1990. Pharmacokinetic study of neostigmine after intranasal and intravenous administration in the guinea pig. *Drugs Exp. Clin. Res.* 16:575-579.
16. Girish, K. S., and K. Kemparaju. 2011. Overlooked issues of snakebite management: time for strategic approach. *Curr. Top. Med. Chem.* 11:2494-2508.
17. Gore et al., 1998, "Comparative biomembrane permeation of tacrine using Yucatan minipigs and domestic pigs as the animal model" *J Pharm Sci* 87:441-447;
18. Kasturiratne et al., 2008, "The global burden of snakebite: a literature analysis and modeling based on regional estimates of envenoming and deaths," *PLoS Med.* 5:e218.
19. L S Guimaraes, Cesar, et al. "Biodiversity as a Source of Bioactive Compounds Against Snakebites." *Current medicinal chemistry* 21.25 (2014): 2952-2979.
20. Magrioti, Victoria, and George Kokotos. "Phospholipase A2 inhibitors as potential therapeutic agents for the treatment of inflammatory diseases." *Expert opinion on therapeutic patents* 20.1 (2010): 1-18),
21. Mebs, D. 2002. *Venomous and Poisonous Animals.* CRC Press, Boca Raton, Fla. 339 pages.
22. Marcussi, Silvana, et al. "Snake venom phospholipase A2 inhibitors: medicinal chemistry and therapeutic potential." *Current Topics in Medicinal Chemistry* 7.8 (2007): 743-756).
23. *Medecins Sans Frontieres*: Snakebite how a public health emergency went under the radar. http://www.doctorswithoutborders.org/article/snakebite-how-public-health-emergency-went-under-radar
24. Ray, et al., "Phospholipase $A_2$ in Airway Disease: Target for Drug Discovery," *Journal of Drug Discovery and Therapeutics* 1 (8) 2013, 28-40
25. Remington: The Science and Practice of Pharmacy, 19th Ed., incorporated herein by reference, at Chapter 95 "Aerosols", and Chapter 41, "Drug Absorption, Action and Disposition."
26. Ricciardi, R., B. Rossi, M. Nicora, A. Sghirlanzoni, and A. Muratorio. 1991. Acute treatment of myasthenia gravis with intranasal neostigmine: clinical and electromyographic evaluation. *J. Neurol. Neurosurg. Psychiatry* 54:1061-1062.
27. Sghirlanzoni et al., "Efficacy of intranasal administration of neostigmine in myasthenic patients." J Neurol. 239: 165-9 (1992).
28. Sharma, S. K., P. Bovier, N. Jha, E. Alirol, L. Loutan, and F. Chappuis. 2013. Effectiveness of Rapid Transport of Victims and Community Health Education on Snakebite Fatalities in Rural Nepal. *Am. J. Trop. Med. Hyg.* 00.
29. Sghirlanzoni, A., D. Pareyson, C. Benvenuti, G. Cei, V. Cosi, M. Lombardi, et al. 1992. Efficacy of intranasal administration of neostigmine in myasthenic patients. *J. Neural.* 239:165-169.
30. Sui y, Qu Z, (2007), Alternative statistical parameter for high-throughput screening assay quality assessment, *J Biomol Screen*, 12, 229-34.
31. "Varespladib" *American Journal of Cardiovascular Drugs.* 11 (2): 137-43. 2011.
32. Villalta-Romero et al. *ACS Med Chem Lett* 2012, 3, 540-543
33. Warrell et al., 1983, "Severe neurotoxic envenoming by the Malayan krait *Bungarus candidus* (Linnaeus): response to antivenom and anticholinesterase.," *Br Med J (Clin Res Ed)* 286(6366):678-80;
34. Warrell, D. A., S. Looareesuwan, N. J. White, R. D. Theakston, M. J. Warren, W. Kosakarn, et al. 1983. Severe neurotoxic envenoming by the Malayan krait *Bungarus candidus* (*Linnaeus*): response to antivenom and anticholinesterase. *BMJ* 286:678-680.
35. Warrell, D. A. 2012. Snakebite: a neglected problem in twenty-first century India. *Natl Med. J. India* 24:321-324.
36. WHO. 2010. *Guidelines for the Prevention and Clinical Management of Snakebite in Africa.* World Health Organization, Brazzaville, Congo, Pp. 87-88.
37. Watt, G., R. D. Theakston, C. G. Hayes, M. L. Yambao, R. Sangalang, C. P. Ranoa, et al. 1986. Positive response to edrophonium in patients with neurotoxic envenoming by cobras (*Naja naja philippinensis*). A placebo-controlled study. *N. Engl. J. Med.* 315:1444-1448
38. Watt et al., Positive response to edrophonium in patients with neurotoxic envenoming by cobras (*Naja naja philippinensis*). A placebo-controlled study" *N Engl J Med.* 1986 315(23):1444-8
39. (J-H Zhang, T D Y Chung, K R Oldenburg, (1999), A simple statistical parameter for use in evaluation and validation of high throughput screening assays, *J Biomol. Screen,* 4, 67-73).

What is claimed is:

1. A method of treating a patient or subject who suffers from an envenomation, wherein said envenomation occurs from a snake, the method comprising administering to the patient or subject a therapeutically effective amount of a PLA2 inhibitor selected from the group consisting of varespladib, methylvarespladib, a pharmaceutically acceptable salt thereof or a mixture thereof.

2. The method according to claim 1 wherein said snake is *Crotalus scutulatus scutulatus* (Mojave rattlesnake) or *Micrurus fulvius* (coral snake).

3. The method according to claim 1 wherein said PLA2 inhibitor is varespladib, methylvarespladib, or a pharmaceutically acceptable salt thereof.

4. The method according to claim 2 wherein said PLA2 inhibitor is varespladib, methylvarespladib, or a pharmaceutically acceptable salt thereof.

5. The method according to claim 1 wherein said PLA2 inhibitor is varespladib which is administered by injection or methylvarespladib which is administered orally, topically or intranasally to the subject (1) at a concentration of between 0.1, 1, 10, 100, 110, 120, 230, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 and 1250, 750 and 1250 or 801 and 1000 μM; and/or (2) in an amount of between 0.0001, 0.001, 0.01, 0.1, 1, 10 or 100 and 1,000 mg, or in an amount of between 1, 10, 20, 30, 40, 50, 60, 70, 80 or 90 and 100 g.

6. The method according to claim 1 wherein reversal or reduction of signs and/or symptoms of envenomation in said patient or subject is evident within 5 minutes to no more than 1440 minutes after initial administration of said PLA2 inhibitor.

7. The method of claim 1 wherein said PLA2 inhibitor is varespladib, methylvarespladib or a pharmaceutically acceptable salt thereof.

8. The method of claim 2 wherein said PLA2 inhibitor is varespladib, methylvarespladib or a pharmaceutically acceptable salt thereof.

9. The method of claim 1 wherein said snake is a rattlesnake of the genus *Crotalus*.

10. The method of claim 5 wherein PLA2 inhibitor is varespladib administered by injection or methylvarespladib administered orally or topically.

11. The method of claim 5 wherein said PLA2 inhibitor is varespladib.

12. The method of claim 5 wherein said PLA2 inhibitor is methylvarespladib administered orally.

13. The method according to claim 2 wherein said snake is a Mojave rattlesnake.

14. The method according to claim 3 wherein said snake is a Mojave rattlesnake.

15. The method according to claim 4 wherein said snake is a Mojave rattlesnake.

16. The method according to claim 5 wherein said snake is a Mojave rattlesnake.

17. The method according to claim 6 wherein said snake is a Mojave rattlesnake.

18. The method according to claim 7 wherein said snake is a Mojave rattlesnake.

19. The method according to claim 8 wherein said snake is a Mojave rattlesnake.

20. The method according to claim 9 wherein said snake is a Mojave rattlesnake.

21. The method according to claim 10 wherein said snake is a Mojave rattlesnake.

22. The method according to claim 11 wherein said snake is a Mojave rattlesnake.

23. The method according to claim 12 wherein said snake is a Mojave rattlesnake.

* * * * *